(12) United States Patent
Fagnou et al.

(10) Patent No.: US 6,784,210 B2
(45) Date of Patent: Aug. 31, 2004

(54) COMPOUND AND A NOVEL PROCESS FOR THEIR PREPARATION

(75) Inventors: Keith Fagnou, Toronto (CA); Mark Lautens, Etobicoke (CA)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/317,183

(22) Filed: Dec. 12, 2002

(65) Prior Publication Data

US 2003/0144275 A1 Jul. 31, 2003

Related U.S. Application Data

(62) Division of application No. 09/763,759, filed as application No. PCT/SE00/02090 on Oct. 26, 2000, now Pat. No. 6,525,068.

(30) Foreign Application Priority Data

Oct. 29, 1999 (SE) ................................................ 9903930

(51) Int. Cl.[7] .................... A61K 31/135; A61K 31/136; C07C 211/44
(52) U.S. Cl. ...................................... 514/657; 564/428
(58) Field of Search .......................... 514/657; 564/428

(56) References Cited

U.S. PATENT DOCUMENTS 6,569,652 B1   5/2003  Eguchi et al.   ..............  435/129

OTHER PUBLICATIONS

Derwent accession No. 1999–190628, Kyowa Hakko Kogyo KK: "Preparation of Optically Active Diol Compounds, e.g., Crixivan—Using Microorganism, e.g., Rodococcus, Bacillus, Brevibacterium or Gordona Species;" AU, A, 4031097, 19990304, DW199916.

Duan, et al., "Palladium–Catalyzed Reductive Couplings of Organic Halides with 7–Heteroatom Norornadienes. New Synthetic Methods for Substituted Aryls and cis–1, 2–Dihydro–1–Naphthyl Alcohols and Carbamates," *Organometallics* 14:1608–1618 (1985).

Dubey, et al., "Synthesis of Dihydro Diols and Diol Epoxides of Benzo[f] quinoline," *J. Org. Chem.* 51:3407–3412 (1986).

Funk, et al., "Development of Chiral Stationary Phases for the Enantiomeric Resolution of Dihydrodiols of Polycyclic Aromatic Hydrocarbons by π–Donor–Acceptor Interactions," *J. Chromotography A.* 659:57–68 (1994).

Hartwig, "Transition Metal Catalyzed Synthesis of Arylamines and Aryl Ethers fom Aryl Halides and Triflates: Scope and Mechanism," *Angewandte Chemie Int. Ed.* 37:2047–2067 (1968).

Kende, et al., "Novel Rearrangements during Dehydration of Nucleophile Adducts of Arene Oxides. A Reappraisal of Premercapture Acid Structures," *J. Am. Chem. Soc.* 97:4427–4428 (1975).

Lautens, et al., "Metal Catalyzed Hydrometalations and Their Applications in Synthesis," *Chemical Abstracts* 129:244669 (1998).

Lautens, et al., "Scope of the Nickel Catalyzed Asymmetric Reductive Ring Opening Reaction. Synthesis of Enantiomerically Enriched Cyclohexenols," *Tetrahedron* 54:1107–1116 (1998).

Lautens, et al., "Exploring the Reactivity of Dioxacyclic Compounds as a Route to Polysubstituted Decalins and Fused Polycycles," *J. Org. Chem.* 63:647–656 (1998).

Lautens, et al., "Base–Induced Ring Opening of Aza– and Thiaoxa[3.2.1] and –[3.3.1]Bicycles as an Enantioselective Approach to Azepines, Thiepines, and Thiocines," *J. Org. Chem.* 62:7080–7081 (1997).

Lautens, et al., "An Expedient Route for the Steroselective Construction of Bridged Polyheterocyclic Ring Systems Using the Tandem 'Pincer' Diels–Alder Reaction," *J. Org. Chem.* 62:4418–4427 (1997).

Moinet, et al., "Palladium–Catalyzed Asymmetric Hydrophenylation of 1,4–Dihydro–1,4–Epoxynaphthalene," *Tetrahedron Letters* 36:2051–2052 (1995).

Posner, et al., "Organic Reactions at Alumina Surfaces. Mild and Selective Opening of Arene and Related Oxides by Weak Oxygen and Nitrogen Nucleophiles," *J. Am Chem. Soc.* 00:8214–8218 (1977).

Von Tugeln, et al., "Stereoselective Metabolism of 9–Methyl–, 9–Hydroxymethyl– and 9,10–Dimethylanthracenes: Absolute Configuration and Optical Purities of Trans–Dihydrodiol Metabolites," *Carcinogenesis* 7:1135–1141 (1986).

Widenhoefer, et al., "Direct Observation of C—O Reductive Elimination from Palladium Aryl Alkoxide Complexes to Form Aryl Ethers," *J. Am. Chem. Soc.* 119:6787–6795 (1997).

*Primary Examiner*—Zinna Northington Davis
(74) *Attorney, Agent, or Firm*—Michael A. Sanzo; Fitch, Even, Tabin & Flannery

(57) ABSTRACT

The present invention is directed to a procedure for making an enantiomerically enriched compound containing a hydronaphthalene ring structure. The process involves reacting oxabenzonorbornadienes with nucleophiles using rhodium as a catalyst and in the presence of a phosphine ligand. The compounds synthesized may be used in pharmaceutical preparations for the treatment of a variety of diseases and conditions.

16 Claims, No Drawings

COMPOUND AND A NOVEL PROCESS FOR THEIR PREPARATION

CROSS REFERENCE TO RELATED APPLICATIONS

The present application is a division of U.S. application Ser. No. 09/763,759, filed on Feb. 27, 2001. Now U.S. Pat. No. 6,525,068 U.S. Ser. No. 09/763,759 represents U.S. national phase of international application PCT/SE00/02090 with an international filing date of Oct. 26, 2000 and which was published in English under Article 21(2) of the PCT on May 3, 2001. The international application claims priority to Swedish application 9903930-7, filed on Oct. 29, 1999.

FIELD OF THE INVENTION

The present invention is directed to methods for chemically synthesizing compounds containing a hydronaphthalene ring structure. It encompasses the compounds made by the methods, pharmaceutical preparations containing the compounds, and methods for treating patients using these pharmaceutical preparations.

BACKGROUND OF THE INVENTION

The hydronaphthalene structure can be found in many natural products and pharmaceutical agents. These include homochelidonine (structure 1 below; Slavik, J.; et al., *Collect. Czech. Chem. Commun.* 30:3697 (1965); Spath, E., et al., *Ber.*, 64:1123 (1931); Bersch, H. W., *Arch. Pharm.* (Weinheim, Ger.), 2914:91 (1958)) an alkaloid isolated from Chelidonium plants, dihydrexidine (structure 2 below; Snyder, S. E., *J. Med. Chem.*, 38:2395 (1995)) which shows antiparkinsonian character, etoposide (structure 3 below; Kamal, A., et al., *Tetrahedron Lett.* 37:3359 (1996)) which is used in the treatment of various cancers, and SF-2315B (structure 4 below; Kim, K., et al., *J. Org. Chem.* 60:6866 (1995)) which is a viral reverse transcriptase inhibitor. In addition, CNS agents, immunoregulatory agents and antibiotics contain variations on this framework (Perrone, R., et al., *J. Med. Chem.* 38:942 (1995)).

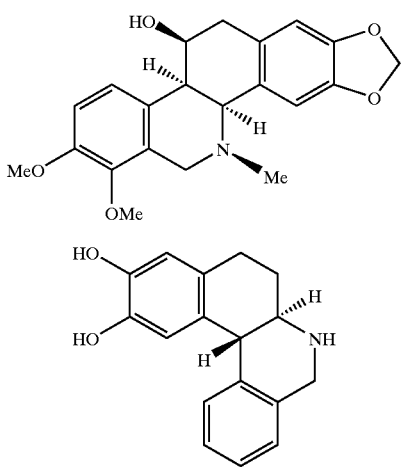

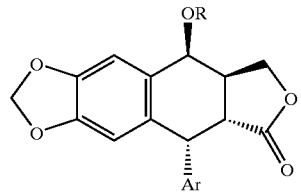

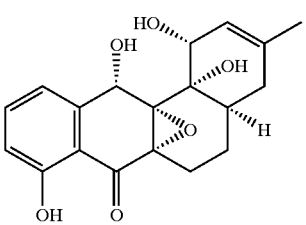

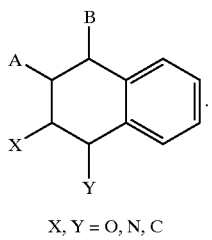

Given the large number of pharmaceutically useful compounds which contain this core skeleton, new methodology which produces functionalized hydronaphthalene skeletons (structure 1) would clearly be of value.

Structure 1

X, Y = O, N, C

Previous work on oxabicyclic ring opening reactions led to a catalytic enantioselective route to dihydronaphthol (Lautens, M., et al., *Tetrahedron* 54:1107 (1998)) which was a key step in the total synthesis of sertraline (Lautens, M., et al, *J. Org. Chem.* 63:5276 (1997)). However, little is known about the ring opening of oxabenzonorbornadiene or similar compounds with the incorporation of nucleophiles during the ring opening step. Duan and Chen developed a method of introducing aryl groups by using catalytic amounts of palladium (Duan, J.-P., et al., *Tetrahedron Lett.*, 34:4019 (1993); Duan, J.-P., et al., *Organometallics* 14:1608 (1995)). Moinet et al., later developed an enantioselective version of this reaction but the yields were low (*Tetrahedron Lett.*, 36:2051 (1995)).

Catalytic organometallic processes that form carbon-heteroatom bonds are far fewer in number than those which form carbon-carbon bonds. The Wacker Process (Henry, P. M., *Paladium Catalysed Oxidation of Hydrocarbons*, vol. 2, Reidel, Boston, (1980)), oxidative carbonylations of amines and alcohols (*Applied Homogeneous Catalysis with Organometallic Compounds: A Comprehensive Handbook in Two Volumes* (eds.: B. Cornils, W. A. Herrmann), VCH, New York, (1984)) and the formation of arylamines and aryl ethers (Hartwig, J. F., *Agnew. Chem. Int. Ed.* 37:2046 (1998); Widenhoefer, R. A., et al., *J. Am. Chem. Soc.* 119:6787 (1997)) are a few that have been described to date.

SUMMARY OF THE INVENTION

The present invention is based upon the discovery of a rhodium catalyzed ring opening reaction of oxabenzonorbornadienes or azabicyclic compounds to produce a new carbon-oxygen bond via an intermolecular reaction with various alcohols. This reaction occurs in good yields with complete regio and diastereoselectivity and excellent enantioselectivity (e.g., eq. 1).

Eq 1

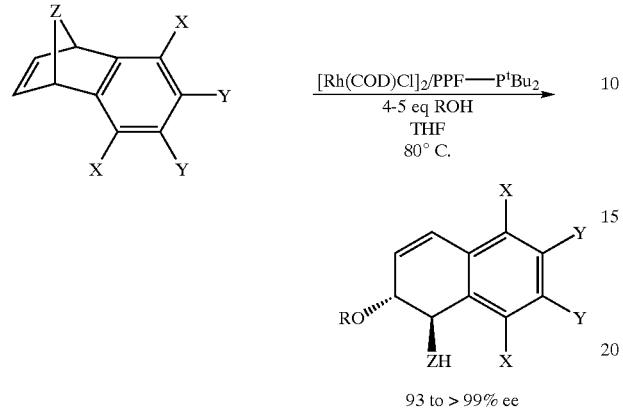

93 to > 99% ee

In the reaction above, Z is O or $NR_a$. This reaction will work when oxabenzonorbornadienes or azabicyclic compounds are reacted with nitrogen nucleophiles, carboxylate nucleophiles, carbon nucleophiles or phenol nucleophiles. The invention encompasses not only the chemical reactions but also the compounds made by the reactions and the use of such compounds in the treatment of a variety of diseases and conditions.

In its first aspect, the invention is directed to a compound according to formula I:

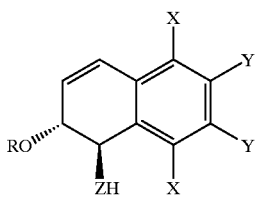

(I)

in which R is selected from the group consisting of:

(a) H;
(b) a $C_1$–$C_6$ straight or branched alkyl;
(c) a straight or branched $C_2$–$C_6$ alkenyl;
(d) —$(CH_2)_nR_1$, wherein $R_1$ is a $C_3$–$C_6$ aryl, optionally substituted at one or more positions with a group selected from: Cl; F; $NO_2$; I; Br; a $C_1$–$C_3$ alkyl; and a $C_1$–$C_3$ alkoxy wherein n=0–3;
(e) —$C(O)R_2$, wherein $R_2$ is selected from the group consisting of: H; —$(CH_2)_nR_1$, wherein $R_1$ is as described above and n=0–3; and —$(CH_2)_nC(O)R_3$, wherein $R_3$ is a $C_1$–$C_6$ straight or branched alkyl and n=0–3;
(f) —$C(O)(CH_2)_p$—$C(O)$—O—$R_4$, wherein $R_4$ is a straight or branched $C_1$–$C_6$ alkyl and wherein p=0–3;
(g) —$R_d(CF_3)_j$, wherein $R_d$ is a $C_1$–$C_3$ straight or branched alkyl and j=1–3;
(h) —$(CH_2)_j$-TMS, wherein TMS is trimethylsilyl, and j=1–3;

X and Y are independently selected from the group consisting, of H; $NH_2$; F; Cl; Br; a $C_1$–$C_3$ alkyl; and a $C_1$–$C_3$ alkoxy;

or wherein the combination XY or YY together form a $C_3$–$C_6$ carbocyclic ring or a $C_3$–$C_6$ heterocyclic ring containing one or more heteroatoms selected from the group consisting of: O; N; and S; and in which Z is selected from O or $NR_a$, wherein $R_a$ is selected from:

(i) phenyl;
(j) (O)C—O—$R_b$, wherein $R_b$ is a straight or branched $C_1$–$C_6$ alkyl;
(k) —$SO_2$—$R_c$, wherein $R_c$ is selected from the group consisting of:
  i) $C_1$–$C_6$ straight or branched alkyl;
  ii) —$(CH_2)_qR_e$, wherein q=0–3 and $R_e$ is a $C_3$–$C_6$ aryl, optionally substituted at one or more positions with a group selected from: Cl; F; $NO_2$; CN; I; Br; a straight or branched $C_1$–$C_3$ alkyl; a $C_1$–$C_3$ alkoxy; and —$C(O)R_f$, wherein $R_f$ is a $C_1$–$C_3$ alkyl; —$(CH_2)_rCF_3$, wherein r=0–3;
  iii) —$R_g(CF_3)_s$, wherein $R_g$ is a $C_1$–$C_3$ straight or branched alkyl and s=1–3;
  iv) —$(CH_2)_s$-TMS, wherein TMS=trimethylsilyl and s=1–3;
(l) —$SO_2$—$(CH_2)_q$—$Si(CH_3)_3$ wherein q is 1–3.

Preferably, R in formula I is —$(CH_2)_nR_1$ and $R_1$ is a $C_3$–$C_6$ aryl optionally substituted at one or more positions with a group selected from: Cl; F; $NO_2$; I; Br; a $C_1$–$C_3$ alkyl; and a $C_1$–$C_3$ alkoxy and wherein n=0–3. When Z is $NR_a$, $R_a$ is preferably phenyl; (O)C—O—C—$(CH_3)_3$; —$SO_2$—$(CH_2)_2$—$Si(CH_3)_3$; or —$SO_2$—$R_c$, wherein $R_c$ is —$(CH_2)_q$$R_e$, wherein q=0–3 and $R_e$ is a $C_3$–$C_6$ aryl, optionally substituted at one or more positions with a group selected from: Cl; F; $NO_2$; CN; I; Br; a straight or branched $C_1$–$C_3$ alkyl; a $C_1$–$C_3$ alkoxy; and —$C(O)R_f$, wherein $R_f$ is a $C_1$–$C_3$ alkyl; —$(CH_2)_sCF_3$, wherein r=0–3.

The compounds of formula I described above may be prepared by reacting a compound of formula ROH with a compound of formula V:

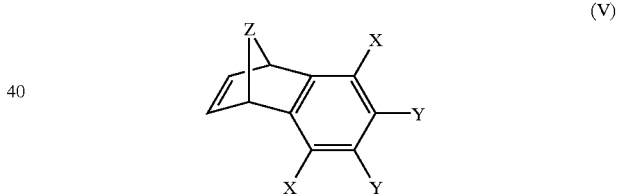

(V)

in which R, X, Y, and Z are as defined above. The reaction is catalyzed by [Rh(COD)Cl]$_2$ in the presence of a phosphine ligand, preferably selected from the group consisting of: DPPF; (R)-(S)-BPPFA; and (R)-(S)-PPF-P$^t$Bu$_2$. In prefered reactions: (a) the compound made is (1R*,2R*)-acetic acid 1-hydroxy-1,2-dihydro-naphthalen-2-yl ester and ROH is acetic acid; (b) the compound made is (1R*,2R*)-propionic acid 1-hydroxy-1,2-dihydro-naphthalen-2-yl ester and ROH is propionic acid; (c) the compound made is (1R,2R)-benzoic acid 1-hydroxy-1,2-dihydro-naphthalen-2-yl-ester and ROH is benzoic acid; (d) the compound made is (1R*,2R*)-formic acid 1-hydroxy-1,2-dihydro-naphthalen-2-yl-ester and ROH is formic acid; (e) the compound made is (1R*,2R*)-2-methyl acrylic acid 1-hydroxy-1,2-dihydro-naphthalen-2-yl-ester and ROH is methacrylic acid; (f) the compound made is (1R*,2R*)-malonic acid ethyl-ester (1-hydroxy-1,2-dihydro-naphthalen-2-yl) ester and ROH is ethyl malonic acid; and (g) the compound made is (1R,2R)-2-(4-bromo-phenoxy)-1,2-dihydro-naphthalen-1-ol and ROH is p-bromophenol; (h) the compound made is N-[(1R,2S)-2-methoxy-1,2-dihydrohydro-1-naphthalenyl]-4-methylbenzene-sulfonamide and ROH is MeOH; (i) the compound made is 4-methyl-N-[(1R,2S)-2-phenoxy-1,2-dihydrohydro-1-naphthalenyl]benzenesulfonamide and the ROH is phenol; (j) the compound made is (1R,2S)-1-{[(4-methylphenyl)sulfonyl]amino}-1,2-dihydrohydro-2-naphthalenyl acetate and the ROH is acetic acid; (k) the compound made is (1R,2S)-1-{[(4-methylphenyl)-sulfonyl]amino}-1,2-dihydro-2-naphthalenyl benzoate and the ROH is benzoic acid; (1) the compound made is (1R,2S)-1-{[(4-methylphenyl)sulfonyl]amino}-1,2-dihydro-2-naphthalenyl pivalate and the ROH is pivalic acid; (m) the compound made is N-[(1R,2S)-2-methoxy-1,2-dihydro-1-naphthalenyl]-2-(trimethylsilyl)ethanesulfonamide and ROH is methanol.

In a second aspect the invention is directed to a compound according to formula II:

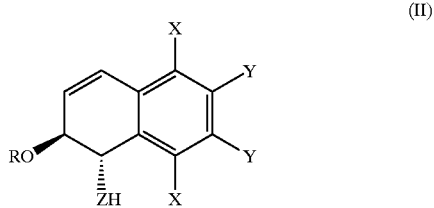

(II)

in which R is selected from the group consisting of:

(a) a $C_1$–$C_6$ straight or branched alkyl;
(b) —$(CH_2)_qR_5$, wherein q=0–3 and $R_5$ is a $C_3$–$C_6$ aryl optionally substituted at one or more positions with a group selected from: a straight or branched $C_1$–$C_3$ alkyl; a $C_1$–$C_3$ alkoxy; Br; I; Cl; CN; F; $NO_2$; —$(CH_2)_rCF_3$, wherein r=0–3; and —$C(O)R_6$, wherein $R_6$ is a $C_1$–$C_3$ alkyl;
(c) —$R_7(CF_3)_s$, wherein $R_7$ is a $C_1$–$C_3$ straight or branched alkyl and s=1–3;
(d) —$(CH_2)_s$-TMS, wherein TMS=trimethylsilyl and s=1–3; X and Y are independently selected from the group consisting of: H; $NH_2$; F; Cl; Br; a $C_1$–$C_3$ alkyl; and a $C_1$–$C_3$ alkoxy;
or wherein the combination XY or YY together form a $C_3$–$C_6$ carbocyclic ring or a $C_3$–$C_6$ heterocyclic ring containing one or more heteroatoms selected from the group consisting of: O; N; and S; and
in which Z is selected from O or $NR_a$, wherein $R_a$ is selected from:
(e) phenyl;
(f). (O)C—O—$R_b$, wherein $R_b$ is a straight or branched $C_1$–$C_6$ alkyl;
(g) —$SO_2$—$R_c$, wherein $R_c$ is selected from the group consisting of:
  i) $C_1$–$C_6$ straight or branched alkyl;
  ii) —$(CH_2)_qR_e$, wherein q=0–3 and $R_e$ is a $C_3$–$C_6$ aryl, optionally substituted at one or more positions with a group selected from: Cl; F; $NO_2$; CN; I; Br; a straight or branched $C_1$–$C_3$ alkyl; a $C_1$–$C_3$ alkoxy; and —$C(O)R_f$, wherein $R_f$ is a $C_1$–$C_3$ alkyl; —$(CH_2)_rCF_3$, wherein r=0–3;
  iii) —$R_g(CF_3)_s$, wherein $R_g$ is a $C_1$–$C_3$ straight or branched alkyl and s=1–3;
  iv) —$(CH_2)_s$-TMS, wherein TMS=trimethylsilyl and s=1–3;
(h) —$SO_2$—$(CH_2)_q$—$Si(CH_3)_3$ wherein q is 1–3.

Preferably, R in formula II is —$(CH_2)_qR_5$ wherein q=0–3 and $R_5$ is a $C_3$–$C_6$ aryl optionally substituted at one or more positions with a group selected from: a straight or branched $C_1$–$C_3$ alkyl; a $C_1$–$C_3$ alkoxy; I; Cl; CN; F; $NO_2$; —$(CH_2)_rCF_3$, wherein r=0–3; and —$C(O)R_6$, wherein $R_6$ is a $C_1$–$C_3$ alkyl.

The compounds of formula II described above may be prepared by reacting a compound of formula ROH with a compound of formula V:

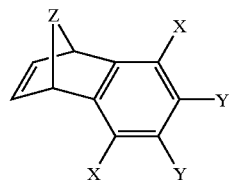

(V)

wherein R, X, Y, and Z are as defined above in connection with formula II and in which the reaction is catalyzed by [Rh(COD)Cl]$_2$ in the presence of a phosphine ligand, preferably (S)-(R)-PPF-P$^t$Bu$_2$. In preferred reactions: (a) the compound made is (1S,2S)-2-methoxy-1,2-dihydro-naphthalen-1-ol, and ROH is methanol; (b) the compound made is (1S,2S)-2-(ethoxy)-1,2-dihydro-naphthalen-1-ol, and ROH is ethanol; (c) the compound made is (1S,2S)-2-isopropoxy)-1,2-dihydro-naphthalen-1-ol and ROH is isopropanol; (d) the compound made is (1S,2S)-2-1-propenyloxy)-1,2-dihydro-naphthalen-1-ol, and ROH is allyl alcohol; (e) the compound made is (1S,2S)-2-(2-trimethylsilyl-ethoxy)-1,2-dihydro-naphthalen-1-ol, and ROH is trimethylsilyl-ethanol; (f) the compound made is (1S,2S)-2-benzyloxy)-1,2-dihydro-naphthalen-1-ol, and ROH is benzylalcohol; (g) the compound made is (1S,2S)-2-4-methoxybenzyloxy)-1,2-dihydro-naphthalen-1-ol, and ROH is anisylalcohol; (h) the compound made is (1S,2S)-2-(2,2,2-trifluoro-ethoxy)-1,2-dihydro-naphthalen-1-ol, and ROH is trifluoroethanol; (i) the compound made is (1S,2S)-2-(2,2,2-trifluoro-1-trifluoromethyl-ethoxy)-1,2-dihydro-naphthalen-1-ol and ROH is hexafluoro-isopropanol; (j) the compound made is (1S,2S)-6,7-difluoro-2-methoxy-1,2-dihydro-naphthalen-1-ol and ROH is methanol; (k) the compound made is (1S,2S)-6-methoxy-5,6-dihydro-naphtho[2,3-d][1,3]dioxol-5-ol and ROH is methanol; (l) the compound made is (1S,2S)-6,7-dibromo-2-methoxy-5,8-dimethyl-1,2-dihydro-naphthalen-1-ol and ROH is methanol; (m) the compound made is (1S,2S)-2-phenoxy-1,2-dihydro-naphthalen-1-ol and ROH is phenol; (n) the compound made is (1S,2S)-2-(4-nitrophenoxy)-1,2-dihydro-naphthalen-1-ol and ROH is 4-nitrophenol; (O) the compound made is (1S,2S)-2-(4-cyanophenoxy)-1,2-dihydro-naphthalen-1-ol and ROH is 4-cyanophenol; (p) the compound made is (1S,2S)-2-(4-acylphenoxy)-1,2,-dihydro-naphthalen-1-ol and ROH is 4-hydroxyacetophenone; (q) the compound made is (1S,2S)-2-(4-trifluoromethylphenoxy)-1,2,-dihydro-naphthalen-1-ol and ROH is 4-trifluoromethylphenyl; (r) the compound made is (1S,2S)-2-(4-fluorophenoxy)-1,2-dihydro-naphthalen-1-ol and ROH is 4-fluorophenol; (s) the compound made is (1S,2S)-2-(4-chlorophenoxy)-1,2-dihydro-naphthalen-1-ol and ROH is 4-chlorophenol; (t) the compound made is (1S,2S)-2-(4-iodophenoxy)-1,2-dihydro-naphthalen-1-ol and ROH is 4-iodophenol; (u) the compound made is (1S,2S)-2-(4-methylphenoxy)-1,2-dihydro-naphthalen-1-ol and ROH is p-cresol; (v) the compound made is (1S,2S)-2-(4-methoxyphenoxy)-1,2-dihydro-naphthalen-1-ol and ROH is 4-methoxyphenol; and (w) the compound made is (1S,2S)-2-(2-bromophenoxy)-1,2-dihydro-naphthalen-1-ol and ROH is 2-bromophenol. When Z is $NR_a$, $R_a$ is preferably phenyl; (O)C—O—C—$(CH_3)_3$;

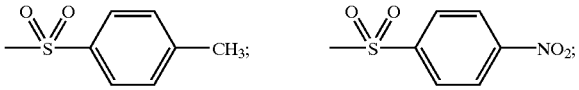

or (O)S(O)—$(CH_2)_2$—$Si(CH_3)_3$.

The invention is also directed to a compound according to formula III:

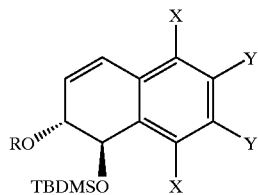

(III)

wherein TBDMSO is a tert-butyldimethylsiloxy group, and R, X, and Y are as defined in above in connection with formula I. These compounds may be made by preparing a compound of formula I according to the process described above and then reacting the compound formed with a salt of tert-butyldimethylsilylic acid. Preferably, the compound formed is (1R*,2R*)-malonic acid (1-tert-butyldimethylsiloxy-1,2-dihydro-naphthalen-2-yl) ester ethyl ester and ROH is tert-butyldimethylsilylic acid.

In another aspect, the invention is directed to a compound according to formula IV:

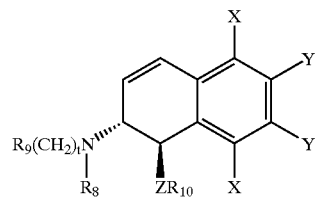

(IV)

a) in which $R_8$ is H or $CH_3$;
b) t=0–3
c) $R_9$ is a $C_3$–$C_6$ aryl optionally substituted at one or more positions with a group selected from: a $C_1$–$C_3$ alkyl; a $C_1$–$C_3$ alkoxy; Cl; F; $NO_2$; and $CF_3$;
   or $R_9$ together with N form a ring structure selected from: a phthalamide ring; a pyrrolidine ring; a piperidine ring; a tetrahydroquinoline ring; and an indole ring; said ring structure being optionally substituted at one or more positions with a group selected from: a $C_1$–$C_3$ alkyl; a $C_1$–$C_3$ alkoxy; Cl; F; $NO_2$; and $CF_3$;
d) X and Y are independently selected from the group consisting of H; $NH_2$; F; Cl; Br; a $C_1$–$C_3$ alkyl; and a $C_1$–$C_3$ alkoxy; or wherein the combination XY or YY together form a $C_3$–$C_6$ carbocyclic ring or a $C_3$–$C_6$ heterocyclic ring containing one or more heteroatoms selected from the group consisting of: O; N; and S;
e) Z is selected from O or $NR_a$, wherein $R_a$ is selected from:
   (i) a straight or branched $C_1$–$C_6$ alkyl;
   (ii) phenyl;
   (iii) (O)C—O—$R_b$, wherein $R_b$ is a straight or branched $C_1$–$C_6$ alkyl;
   (iv) —$SO_2$—$R_c$, wherein $R_c$ is an unsubstituted phenyl or a phenyl substituted with a $C_1$–$C_3$ alkyl or $NO_2$; and
   (v) —$SO_2$—$(CH_2)_q$—$Si(CH_3)_3$ wherein q is 1–3; and
f) when Z is O, $R_{10}$ is H; when Z is $NR_a$, $R_{10}$ is either H or $CH_3$.

Preferably, $R_8$ in formula IV is H and $R_9$ together with N form a ring selected from the group consisting of a phthalamide ring; a pyrrolidine ring; a piperidine ring; a tetrahydroquinoline ring; and an indole ring; the ring being optionally substituted at one or more positions with a group selected from: a $C_1$–$C_3$ alkyl; a $C_1$–$C_3$ alkoxy; Cl; F; $NO_2$; and $CF_3$. When Z is $NR_a$, $R_a$ is preferably methyl;

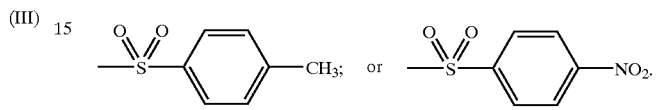

The compounds of formula IV described above may be prepared by reacting a compound of formula $R_9$—$(CH_2)_t$—$NHR_8$ with a compound of formula V

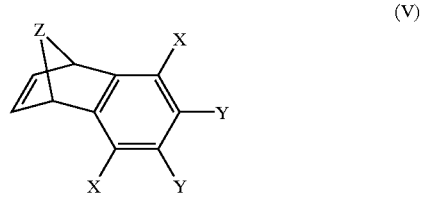

(V)

in which $R_8$, $R_9$, t, X, Y, and Z are as defined above in connection with compounds of formula IV and the reaction is catalyzed by $[Rh(COD)Cl]_2$ in the presence of a phosphine ligand; preferably selected from the group consisting of: DPPF; (R)-(S)-BPPFA; and (R)-(S)-PPF-P'$Bu_2$. When Z is $NR_a$, the reaction will produce a product in which $R_{10}$ is H. A subsequent reaction may be used to convert $R_{10}$ to a methyl as set forth in the Examples section below. Most typically, the process will be used to produce products in which $R_9$ together with N form a ring selected from the group consisting of: a phthalamide ring; a pyrrolidine ring; a piperidine ring; a tetrahydroquinoline ring; and an indole ring; said ring structures being optionally substituted at one or more positions with a group selected: a $C_1$–$C_3$ alkyl; a $C_1$–$C_3$ alkoxy; Cl; F; $NO_2$; and $CF_3$. In preferred reactions: (a) the compound made is (1R,2R)-2-(1-hydroxy-1,2-dihydro-naphthalen-2-yl) isoindole-1,3-dione and $R_9$—$(CH_2)_s NHR_8$ is phthalimide; (b) the compound made is (1R*,2R*)-2-pyrrolidin-1-yl-1,2-dihydro-naphthalen-1-ol and $R_9$—$(CH_2)_s NHR_8$ is pyrrolidine; (c) the compound made is (1 R*,2R*)-2-piperidin-1-yl-1,2-dihydro-naphthalen-1-ol and $R_9$—$(CH_2)_s NHR_8$ is piperidine; (d) the compound made is (1R,2R)-2-(3,4-dihydro-2H-quinolin-1-yl)-1,2-dihydro-naphthalen-1-ol and $R_9$—$(CH_2)_s NHR_8$ is tetrahydroisoquin-oline; (e) the compound made is (1R,2R)-2(methyl-phenyl-amino)-1,2-dihydro-naphthalen-1-ol and $R_9$—$(CH_2)_s NHR_8$ is N-methylaniline; (f) the compound made is (1R*,2R*)-2-benzylamino-1,2-dihydro-naphthalen-1-ol and $R_9$—$(CH_2)_s NHR_8$ is benzyl-amine; (g) the compound made is (1R*,2R*)-2-(4-methoxy-benzylamino)-1,2-dihydro-naphthalen-1-ol and $R_9$—$(CH_2)_s NHR_8$ is p-methoxybenzylamine; and (h) the compound made is (1R,2R)-2-indol-1-yl-1,2-dihydro-naphthalen-1-ol and $R_9$—$(CH_2)_s NHR_8$ is indole; (i) the compound made is N-[1R,2R)-2(1-pyrrolidinyl)-1,2-dihydronaphthalenyl]-4- methylbenzenesulfonamide and the R₉—(CH₂)ᵣNHR₈ is pyrrolidine; (j) the compound made is N-[(1R,2S)-2-(1H-indol-1-yl)-1,2-dihydro-1-naphthalenyl]-4-methylbenzenesulfonamide and the R₉—(CH₂)ᵣNHR₈ is indole; (k) the compound made is N-[(1R,2S)-2-(3,4-dihydro-2(1H)-isoquinolinyl)-1,2-dihydro-1-naphthalenyl]-4-methylbenzenesulfonamide and the R₉—(CH₂)ᵣNHR₈ is tetrahydroisoquinoline; (l) the compound made is N-[(1R,2S)-2-(3,4-dihydro-1(2H)-quinolinyl)-1,2-dihydro-1-naphthalenyl]-4-methylbenzenesulfonamide and the R₉—(CH₂)ᵣNHR₈ is tetrahydroquinoline; (m) the compound made is 4-methyl-N-[(1R,2S)-2-(1-piperidinyl)-1,2-dihydro-1-naphthalenyl]-benzenesulfonamide and the R₉—(CH₂)ᵣNHR₈ is piperidine.

The invention also encompasses seven other processes. In the first (1S,2S)-N-(1-hydroxy-1,2-dihydro-naphthalen-2-yl)-benzene sulfonamide is formed by reacting oxabenzonorbornadiene with benzenesulfonamide. In the second, (1S*,2R*)-2-(hydroxy-1,2-dihydro-naphthalen-2-yl) malonic acid dimethyl ester is formed by reacting oxabenzonorbornadiene with dimethyl malonate. Both reactions are catalyzed by [Rh(COD)Cl]₂ in the presence of a phosphine ligand. In the third, the compound of formula VI is formed by reacting a compound of formula IV, which is produced as described above in connection with formation of compounds of formula IV, with iodomethane. In preferred reactions, the compound made is N,4-dimethyl-N-[(1R,2S)-2-(1-pyrrolidinyl)-1,2-dihydro-1-naphthalenyl] benzenesulfonamide. In the fourth, the compound of formula VII is formed by reacting compound of formula VI with hydrogen in the presence of palladium catalyst. The compound made is N,4-dimethyl-N-[(1R,2S)-2-(1-pyrrolidinyl)-1,2,3,4-tetrahydro-1-naphthalenyl] benzenesulfonamide. In the fifth, the compound of formula VIII is formed by reacting the compound of formula VII with sodium borohydride. The compound made using this reaction is (1R,2S)-N-methyl-2-(1-pyrrolidinyl)-1,2,3,4-tetrahydro-1-naphthalenamine. In the sixth, the compound of formula IX is formed by reacting a compound of formula IV which is produced as described above in connection with formation of compounds of formula IV, with iodomethane. The compound made using this reaction is N-methyl-4-nitro-N-[(1R,2S)-2-(1-pyrrolidinyl)-1,2-dihydro-1-naphthalenyl]benzenesulfonamide. In the seventh, the compound of formula X is formed by reacting a compound of formula I which is produced as described above in connection with formation of compounds of formula I, with iodomethane. The compound made using this reaction is (1R,2S)-1-{methyl[(4-methylphenyl)sulfonyl]amino}-1,2-dihydro-2-naphthalenyl acetate.

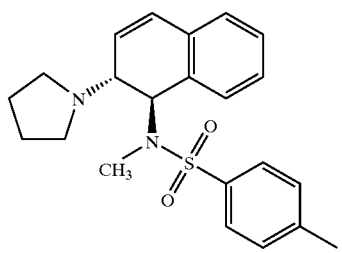

VI

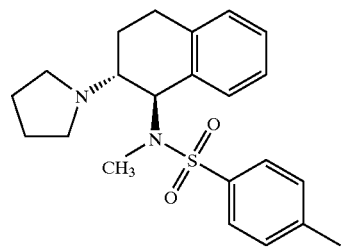

VII

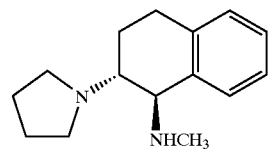

VIII

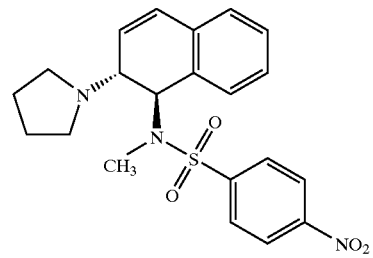

IX

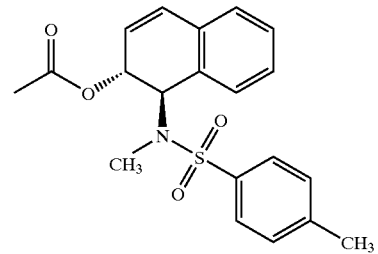

X

Overall, the most preferred compounds of the invention are:

a) (1S,2S)-2-methoxy-1,2-dihydro-naphthalen-1-ol;
b) (1S,2S)-2-(ethoxy)-1,2-dihydro-naphthalen-1-ol;
c) (1S,2S)-2-(isopropoxy)-1,2-dihydro-naphthalen-1-ol;
d) (1S,2S)-2-(1-propenyloxy)-1,2-dihydro-naphthalen-1-ol;
e) (1S,2S)-2-(2-trimethylsilyl-ethoxy) 1,2-dihydro-naphthalen-1-ol;
f) (1S,2S)-2-benzyloxy-1,2-dihydro-naphthalen-1-ol;
g) (1S,2S)-2-(4-methoxybenzyloxy)-1,2-dihydro-naphthalen-1-ol;
h) (1S,2S)-2-(2,2,2-trifluoro-ethoxy)-1,2-dihydro-naphthalen-1-ol;
i) (1S,2S)-2-(2,2,2-trifluoro-1-trifluoromethyl-ethoxy)-1,2-dihydro-naphthalen-1-ol;
j) (1S,2S)-6,7-difluoro-2-methoxy-1,2-dihydro-naphthalen-1-ol;
k) (1S,2S)-6-methoxy-5,6-dihydro-naphtho[2,3-d][1,3]dioxol-5-ol;
l) (1S,2S)-6,7-dibromo-2-methoxy-5,8-dimethyl-1,2-dihydro-naphthalen-1-ol;
m) (1R*,2R*)-acetic acid 1-hydroxy-1,2-dihydro-naphthalen-2-yl-ester;
n) (1R*,2R*)-propionic acid 1-hydroxy-1,2-dihydro-naphthalen-2-yl-ester;
o) (1R,2R)-benzoic acid 1-hydroxy-1,2-dihydro-naphthalen-2-yl-ester;

p) (1R*,2R*)-formic acid 1-hydroxy-1,2-dihydro-naphthalen-2-yl-ester;
q) (1R*,2R*)-2-methyl acrylic acid 1-hydroxy-1,2-dihydro-naphthalen-2-yl-ester;
r) (1R*,2R*)-malonic acid ethyl ester (1-hydroxy-1,2-dihydro-naphthalen-2-yl) ester;
s) (1R*,2R*)-malonic acid (1-tert-butylbimethylsiloxy-1,2-dihydro-naphthalen-2-yl) ethyl ester;
t) (1S*,2S*)$_4$-tert-butyldimethylsiloxy-1,4-dihydro-naphthalen-2-yl) acetic acid ethyl ester;
u) (1R,2R)-2-(1-hydroxy-1,2-dihydro-naphthalen-2-yl)-isoindole-1,3-dione;
v) (1S,2S)-N-(1-hydroxy-1,2-dihydro-naphthalen-2-yl)-benzene sulfonamide;
w) (1R*,2R*)-9-pyrrolidin-1-yl-1,2-dihydro-naphthalen-1-ol;
x) (1R*,2R*)-2-piperidin-1-yl-1,2-dihydro-naphthalen-1-ol;
y) (1R,2R)-2-(3,4-dihydro-2H-quinolin-1-yl)-1,2-dihydro-naphthalen-1-ol;
z) (1R,2R)-2-(methyl-phenyl-amino)-1,2-dihydro-naphthalen-1-ol;
aa) (1R*,2R*)-2-benzylamino-1,2-dihydro-naphthalen-1-ol;
bb) (1R*,2R*)-2-(4-methoxy-benzylamino)-1,2-dihydro-naphthalen-1-ol;
cc) (1R,2R)-2-indol-1-yl-1,2-dihydro-naphthalen-1-ol;
dd) (1S*,2R*)-2-(hydroxy-1,2-dihydro-naphthalen-2-yl) malonic acid dimethyl ester;
ee) (1S,2S)-2-phenoxy-1,2-dihydro-naphthalen-1-ol;
ff) (1S,2S)-2-(4-nitrophenoxy)-1,2-dihydro-naphthalen-1-ol;
gg) (1S,2S)-2-(4-cyanophenoxy)-1,2-dihydro-naphthalen-1-ol;
hh) (1S,2S)-2-(4-acylphenoxy)-1,2-dihydro-naphthalen-1-ol;
ii) (1S,2S)-2-(4-trifluoromethylphenoxy)-1,2-dihydro-naphthalen-1-ol;
jj) (1S,2S)-2-(4-fluorophenoxy)-1,2-dihydro-naphthalen-1-ol;
kk) (1S,2S)-2-(4-chlorophenoxy)-1,2-dihydro-naphthalen-1-ol;
ll) (1S,2S)-2-(4-iodophenoxy)-1,2-dihydro-naphthalen-1-ol;
mm) (1R,2R)-2-(4-bromo-phenoxy)-1,2-dihydro-naphthalen-1-ol;
nn) (1S,2S)-2-(4-methylphenoxy)-1,2-dihydro-naphthalen-1-ol;
oo) (1S,2S)-2-(4-methoxyphenoxy)-1,2-dihydro-naphthalen-1-ol;
pp) (1S,2S)-2-(2-bromophenoxy)-1,2-dihydro-naphthalen-1-ol;
qq) 4-methyl-N-[(1R,2S)-2-(1-piperidinyl)-1,2-dihydro-1-naphthalenyl]benzenesulfonamide;
rr) N-[(1R,2S)-2-(3,4-dihydro-1 (2H)-quinolinyl)-1,2-dihydro-1-naphthalenyl]-4-methylbenzenesulfonamide;
ss) N-[(1R,2S)-2-(3,4-dihydro-2(1 h)-isoquinolinyl)-1,2-dihydro-1-naphthalenyl]-4-methylbenzenesulfonamide;
tt) N-[(1R,2S)-2-(1H-indol-1-yl)-1,2-dihydro-1-naphthalenyl]-4-methylbenzenesulfonaminde;
uu) (1R,2S)-2-methoxy-N-phenyl-1,2-dihydro-1-naphthalenamine;
vv) tert-butyl (1R,2S)-2-methoxy-1,2-dihydro-1-naphthalenylcarbamate;
ww) N-[(1R,2S)-2-methoxy-1,2-dihydro-1-naphthalenyl]-2-(trimethylsilyl)ethanesulfonamide;
xx) N,4-dimethyl-N-[(1R,2S)-2-(1-pyrrolidinyl)-1,2,3,4-tetrahydro-1-naphthalenyl]-benzenesulfonamide;
yy) N,4-dimethyl-N-[(1R,2S)-2-(1-pyrrolidinyl)-1,2-dihydro-1-naphthalenyl]-benzenesulfonamide;
zz) N-hydroxy-4-({methyl[(1R,2S)-2-(1-pyrrolidinyl)-1,2-dihydro-1-naphthalenyl]amino}sulfonyl)-N-oxobenzenaminium;
aaa) N-methyl-4-nitro-N-[(1R,2S)-2-(1-pyrrolidinyl)-1,2-dihydro-1-naphthalenyl]-benzenesulfonamide;
bbb) (1R,2S)-N-methyl-2-(1-pyrrolidinyl)-1,2,3,4-tetrahydro-1-naphthalenamine;
ccc) N-[(1R,2S)-2-methoxy-1,2,3,4-tetrahydro-1-naphthalenyl]-4-methylbenzenesulfonamide;
ddd) N-[(1R,2S)-2-methoxy-1,2,3,4-tetrahydro-1-naphthalenyl]-4-methylbenzenesulfonamide;
eee) 4-methyl-N-[(1R,2S)-2-phenoxy-1,2,3,4-tetrahydro-1-naphthalenyl]benzenesulfonamide;
fff) (1R,2S)-1-{[(4-methylphenyl)sulfonyl]amino}-1,2,3,4-tetrahydro-2-naphthalenyl acetate;
ggg) (1R,2S)-1-{[(4-methylphenyl)sulfonyl]amino}-1,2-dihydro-2-naphthalenyl benzoate;
hhh) (1R,2S)-1-{[(4-methylphenyl)sulfonyl]amino}-1,2-dihydro-2-naphthalenyl pivalate;
iii) N-[(1R,2S)-2-methoxy-1,2-dihydro-1-naphthalenyl]-2-(trimethylsilyl)ethanesulfonamide;
jjj) tert-butyl (1R,2S)-2-methoxy-1,2-dihydro-1-naphthalenylcarbamate; and
kkk) 4-nitro-N-[(1R,2S)-2-(1-pyrrolidinyl)-1,2-dihydro-1-naphthalenyl]benzenesulfonamide.

Any of the compounds described above may be incorporated into a pharmaceutical preparation and administered to a patient in an amount effect for relieving one or more symptoms associated with a variety of diseases and conditions. Among the diseases that may be treated are Parkinson's disease, cancer and AIDS.

DETAILED DESCRIPTION OF THE INVENTION

The present invention is based upon the discovery of a new process for the formation of enantiomerically enriched compounds containing the hydronaphthalene ring structure. The process involves reacting an aza- or oxabenzonorbornadiene compound with a nucleophile in the presence of a rhodium catalyst and a phosphine ligand. Detailed procedures for the formation of precursor compounds and their use in reactions are set forth in the Examples section below. Preferred nucleophiles are alcohols, phenols, amines, and stabilized carbanions such as malonates and malonate equivalents. In cases where simple aliphatic amines are used, reactions should be performed in the presence of a tertiary amine hydrochloride. This is not necessary for other types of amines. When carboxylic acids are used, reactions should be carried out in the presence of a tertiary amine, e.g., triethylamine. Alternatively, the sodium or potassium salt of the carboxylic acid may be reacted in the presence of the hyrochloride of a tertiary amine, e.g. in the presence of triethylamine hydrochloride. It has been found that carboxylate ring-opened products can be made to undergo a subsequent transformation to produce 1,4-disubstituted dihyronaphthalenes. This is accomplished by an $S_N2'$ addition of nucleophiles under catalytic or non-catalytic conditions to the allyl acetate functionality. For an example of the conversion of (1R*,2R*)-Malonic acid (1-tert-butyldimethylsiloxy-1,2-dihydro-naphthalen-2-yl) ester ethyl ester to (1S*,2S*)-(4-Tert-butyldimethylsiloxy-1,4-dihydro-naphthalen-2-yl) acetic acid ethyl ester see the Examples section below.

The preferred catalyst is [Rh(COD)Cl]$_2$ and, depending upon the particular product desired, preferred ligands are DPPF or a chiral analogs of DPPF, (R)-(S)-BPPFA; (R)-(S)-

PPF-P'Bu₂ and (S)-(R)-PPF-P'Bu₂. The ligands may be prepared by any process described in the literature (see, e.g., Toni et al., *J. Am. Chem. Soc.* 116:4062 (1994)). Reactions may be carried out using trifluoroethanol (TEE) or tetrahydrofuran (THE) as solvents under an inert atmosphere, preferably of nitrogen. The reaction temperature should typically be at least 60° C. and preferably about 80° C.

The compounds formed may be incorporated into a pharmaceutical composition and used in the treatment of a variety of diseases and conditions. Specifically, the compounds may be used in the treatment of Parkinson's disease, cancers, and AIDS. The total daily dosage of compound administered to a patient should be at least the amount required to reduce or eliminate one or more symptoms associated with the condition being treated. For example, in the treatment of Parkinson's disease, sufficient agent should be administered to reduce the severity or frequency of tremors or other movement disorders associated with the disease. In treating cancers, agents should typically be given at a dosage sufficient to reduce tumor size or at a dosage sufficient to reduce the total number of cancerous cells in a patient. The actual dose selected for an individual patient will be determined by the attending physician based upon clinical conditions and using methods well known in the art. Agents may be provided in either a single or multiple dosage regimen, e.g., a patient may be administered compounds twice a day.

Any route of administration and dosage form is compatible with the present invention, and therapeutic agents may be administered as either the sole active ingredient or in combination with other therapeutically active drugs. Routes of delivery compatible with the invention include parenteral, per oral, internal, pulmonary, rectal, nasal, vaginal, lingual, transdermal, intravenous, intra arterial, intramuscular, intraperitoneal, intra cutaneous, and subcutaneous routes. Specific dosage forms that may be used include tablets, pills, capsules, powders, aerosols, suppositories, skin patches, parenteral, and oral liquids, including oil aqueous suspensions, solutions, and emulsions. Sustained release dosage forms may also be used. All dosage forms may be prepared using methods that are standard in the art (see, e.g., *Reaming's Pharmaceutical Sciences*, 16$^{the}$ ed., A. Oslo, editor, Easton Pa. (1980)).

Therapeutic agents may be used in conjunction with any of the vehicles and excipients nly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations designed for oral administration. Solutions can be prepared using water or physiologically compatible organic solvents such as ethanol, 1,2-propylene glycol, polyglycols, dimethyl sulfoxide, fatty alcohols, triglycerides, partial esters of glycerine, and the like. Parenteral compositions containing compounds may be prepared using conventional techniques and include sterile isotonic saline, water, 1,3-butane diol, ethanol, 1,2-propylene glycol, polyglycols mixed with water, Ringer's solution, etc.

If desired, a patient may be initially given a relatively low dose of therapeutic agent in order to determine whether any adverse side effects are experienced. This may be particularly important in cases where a patient is taking other medications or has clinical characteristics that suggest that they may not be able to tolerate high drug dosages. If adverse side effects are not experienced by a patient, dosage may be gradually increased until a satisfactory alleviation of symptoms is achieved. For example, the dosage given to a patient with AIDS may be increased until blood counts return to a normal or more normal level.

EXAMPLES

I. Compounds Made Using Oxabenzonorbornadienes

Example 1

Rhodium Catalysed Synthesis of Enatiomerically Enriched trans-2-Alkoxy-1,2-dihydro-naphthalen-1-ols In 1973, Hogeveen and Middelkoop reported a [Rh(CO)₂Cl]₂ catalyzed ring opening reaction of 5 by reaction with methanol giving 6. (Hogeveen, H., et al., *Tetrahedron Lett.* 190:1 (1973)) Subsequently, Ashworth and Berchtold reported the stereochemistry of this reaction to be cis as shown after the formation of a Diels-Alder adduct with 9 (scheme 1) (Ashworth, R. W., et al., *Tetrehedron Lett.* 339 (1977)). This stereochemistry is in keeping with the observation of exo attack by nucleophiles with other oxabicyclic starting materials (Lautens, M., *Synlett* 179 (1993)). Hogeveen and Middelkoop also reported that the reaction was regioselective when only one of the bridgehead positions was substituted, that is 11 gave only regioisomer 12.

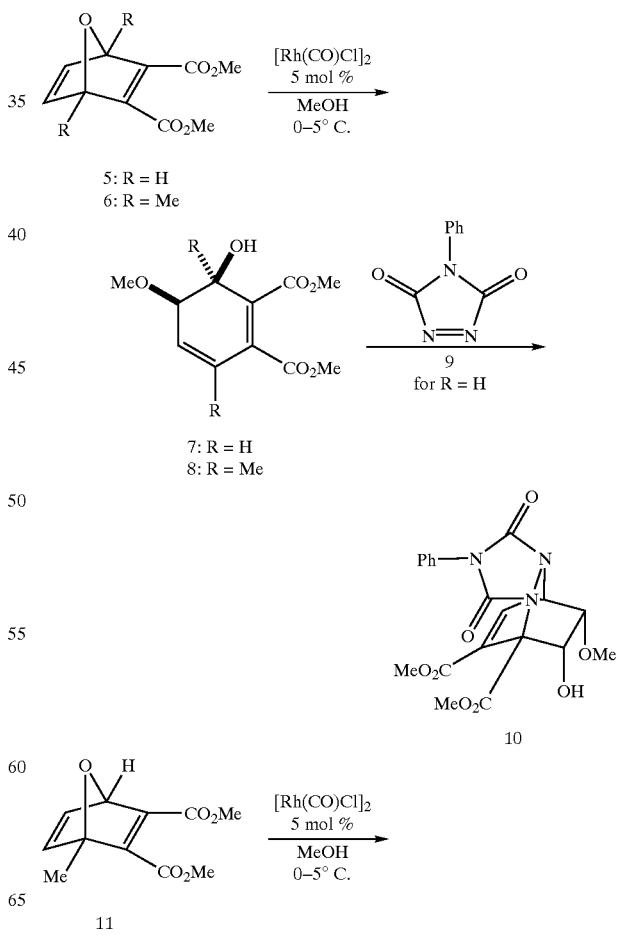

Scheme 1

-continued

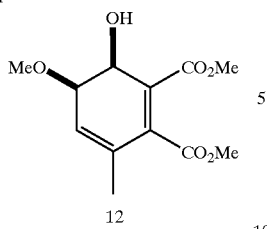

12

When 13 (Stiles, M., e al., *J. Am. Chem. Soc.* 82:3802 (1960)) was subjected to the Hogeveen and Middelkoop conditions, no reaction was observed. However, by changing the solvent system to a 1:1 mixture of trifluoroethanol (TFE):methanol and by increasing the temperature to 60° C., the desired product 14 was isolated in 70% yield. Remarkably, the stereochemistry of 14 was trans as proven by comparison with authentic samples of both stereoisomers of dimethoxytetrahydronaphthalene 15 (eq. 2) (The cis isomer of 15 was prepared by reaction of 1,2-dihydronaphthalene with $OSO_4$ followed by methylation with dimethylsulfate (DMS). The trans isomer was prepared by epoxidation of 1,2-dihydronaphthalene followed by ring opening with hyroxide and dimethylation with DMS).

Eq 2

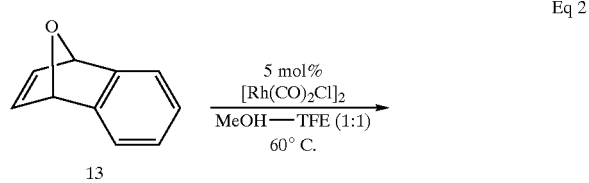

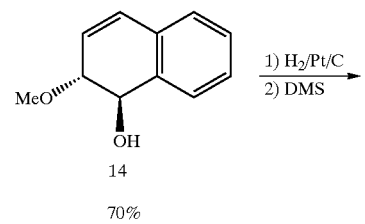

14
70%

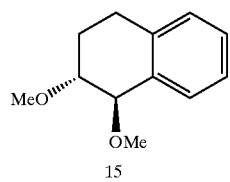

15

Given the ability of this reaction to set tip two stereocentres with complete regio and stereocontrol, the possibility of rendering it asymmetric was investigated. A serious drawback of the existing catalyst $[Ph(CO)_2Cl]_2$, however, was that the addition of phosphine ligands completely inhibited the reaction. By changing to a rhodium source possessing the more labile COD ligand, $[Rh(COD)Cl]_2$, it was possible to examine the catalytic ability of several chiral phosphine ligands. Not all rhodium-ligand combinations performed equally well. DPPE and BINAP did not produce the desired product, and phosphites resulted in poor yields. DPPF was very efficient, however, giving 14 in 88% yield. One advantage of DPPF is that a number of chiral analogues have been prepared and could be studied to determine enantioselectivity. JOSIPHOS ligands (Togni, A., et al., *J. Am. Chem. Soc.* 116:4062 (1994)) were among the chiral ligands examined which gave the most promising results. For example, PPF- P$^t$Bu$_2$ 16 gave 14 in 84% yield and 86% ee at 60° C. The ee could be significantly improved to 97% when the reaction temperature was increased by 20° C.

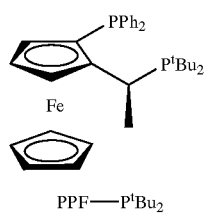

PPF——P$^t$Bu$_2$

18

These reactions were typically run as a 1:1 mixture of MeOH:TFE under a nitrogen atmosphere which gave 13 accompanied by small amounts of naphthol. In neat trifluoroethanol under a nitrogen atmosphere, naphthol is the major product with less than 5% conversion to the trifluoroethanol ring-opened product. Remarkably, this is not the case when the reaction is run under a carbon monoxide atmosphere. In the presence of CO, the reaction with neat TFE gives the TFE ring-opened product 17 in 70% yield after 3 hours. A colour change of the solution, from yellow to red was observed, suggesting that the CO was interacting with the rhodium metal. When the reaction was performed under asymmetric conditions using PPF-P$^t$Bu$_2$, 17 was obtained in 70% yield and 98% ee indicating that the ligand remains bound to the metal even if CO binding has occurred (table 1).

TABLE 1

Effects of Solvent and Atmosphere

12 →[0.25 mol % [Rh(COD)Cl]$_2$ / 18 / 0.5 mol % / CF$_3$CH$_2$OH / 80° C.] 19

| Atmosphere | Solvent/Equiv. TFE | Yield 19 | ee |
|---|---|---|---|
| N$_2$ | TFE/neat | 0%* | |
| CO | TFE/neat | 70% | 98% |
| N$_2$ | THF/5 eq. TFE | 70% | 98% |

*only product observed is naphthol

Reactions run in alcohols other that TFE proceeded at a much slower rate. When the solvent was changed to THF, the reaction worked equally well with a broad range of alcohols under racemic and enantioselective conditions, and only five equivalents of the alcohol were required. THF also allowed the use of very low catalyst loadings, typically in the range of 0.125 mmol % of $[Rh(COD)Cl]_2$ and 0.25 mol % of 16. While TFE would only add to give 17 when the reaction was run under a CO atmosphere in neat TFE, this was not the case in THF. When THF was used as the solvent, TFE added efficiently under an inert nitrogen atmosphere to give 17 in 70% yield and 98% ee. Even the very weakly nucleophilic hexafluoroisopropanol (HFI) added under these reaction conditions to give 23 in 90% yield and 93% ee (table 2).

TABLE 2

Rhodium Catalysed Ring Opening of 12 with Various Alcohols

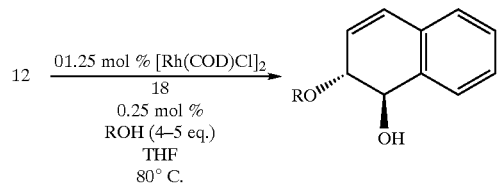

| ROH | Product | Yield(%) | ee(%)[b] |
|---|---|---|---|
| MeOH[a] | 14 | 96 | 97 |
| EtOH[a] | 16 | 84 | 97 |
| iPrOH[a] | 18 | 94 | 93 |
| Allyl Alcohol | 19 | 92 | >99 |
| TMS Ethanol[a] | 20 | 53 | 95 |
| Benzyl Alcohol | 21 | 66 | >98 |
| p-Methoxybenzyl Alcohol | 22 | 87 | 97 |
| TFE | 17 | 70 | 98 |
| HFI | 23 | 90 | 93 |

[a]These reactions were performed under unoptimised conditions using 10 eq ROH
[b]ee determined by formation of Moshers ester or by HPLC analysis with a Chiralcel OD Column In order to investigate the effects of substituents on the aromatic ring of 13, difluoro (24), methylenedioxy (25), and dimethyldibromo (26) substrates were prepared (Hart, H., *Tetrahedron* 43:5203 (1987)) and reacted them under the standard conditions. All gave the corresponding ring opened products in good yields and excellent ee's (chart 1) indicating that this reaction is not sensitive to remote substitution or electronic effects on the aromatic ring.

Chart 1

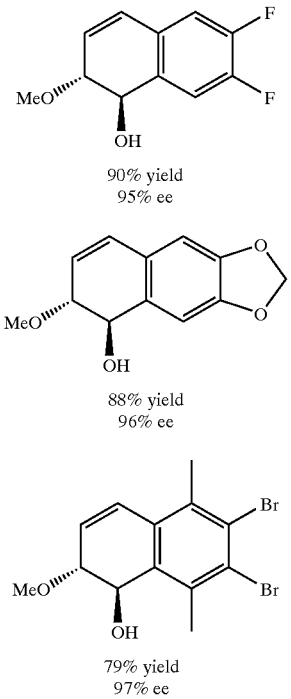

27
90% yield
95% ee 28
88% yield
96% ee 29
79% yield
97% ee

Example 2

Formation of 1,4-epoxy-1,4-dihydronaphthanlene (13)

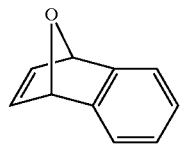

To furan (100 ml, 1.37 ml) in DME (100 ml) at 50° C. in a flame dried three neck flask with a reflux condenser and two addition funnels attached was added simultaneously over two hours a solution of anthranilic acid (27.5 g, 200 mmol) in DME (100 ml) and a separate solution of isoamylnitrite (40 mL, 298 mmol) in DME (50 mL). Upon completion of addition, the reaction was allowed to stir at 50° C. for 30 min until no further gas was evolved. The reaction mixture was then cooled to room temperature and portioned between Et$_2$O and saturated K$_2$CO$_3$ and the aqueous layer was extracted three times with Et$_2$O. The combined organic layer were washed with brine, dried over MgSO$_4$ and concentrated. Bulb to bulb distillation gave 13 (18.5 g, 64%) as a white solid. The spectral data correspond well with the literature data.[17]

Example 3

Compounds Formed by Reactions Involving Alcohols

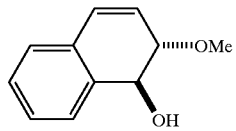

(1S,2S)-2-Methoxy-1,2-dihydro-naphthalen-1-ol (14) To a flame dried round bottom flask, [Rh(COD)Cl]$_2$ (0.5 mg, 0.0009 mmol), (R)-(S)-PPF-P$^t$Bu$_2$ (1.0 mg, 0.0018 mmol) and 13 (27 mg, 0.187 mmol) were added followed by addition of THF (0.5 mL) and methanol (0.5 mL). The mixture was heated for 15 hours and the solvents were removed in vacuo. The resulting solid was purified by flash chromatography (20% ethyl acetate in hexanes) to give 14 a white crystalline solid (31.7 mg, 96%). The ee was determined to be 97% using HPLC analysis on a CHIRALCEL OD column, λ=486 nm. Retention times in 4% isopropanol in hexanes were 10.1 min (major) and 11.1 min. $R_f$=0.29 on silica gel (10% ethyl acetate:hexanes); mp 86–87° (Et$_2$O); $[\alpha]^{25}_D$=−208° (c=10.1, CHCl$_3$); $R_f$=0.39 on silica (20% ethyl acetate:hexanes). IR (KBr, cm$^{-1}$) 3277 (br), 2971 (m), 1466(m), 1285(m), 1114(s), 1048(m), 979(m), 775(s); $^1$H NMR (400 MHz, acetone-d) δ 7.60–7.62 (1H, m), 7.30–7.21 (2H, m), 7.13–7.11 (1H, m), 6.50 (1H, dd, J=9.9, 1.8 Hz), 6.04 (1H, dd, J=9.9, 2.2 Hz), 4.85 (1H, dd, J=9.9, 6.2 Hz), 3.50 (3H, s), 2.89 (1H, d, J=12.8 Hz); $^{13}$C NMR (400 MHz, acetone-d) δ 138.5, 133.2, 129.1, 128.4, 128.3, 128.2, 126.8, 126.3, 83.1, 73.0, 57.1. HRMS calcd for C$_{11}$H$_{12}$O$_2$ (M$^+$): 176.0837. Found: 176.0835.

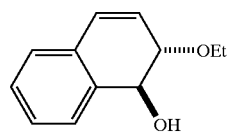

(1S,2S)-2-(Ethoxy)-1,2-dihydro-naphthalen-1-ol (16): To a flame dried round bottom flask, [Rh(COD)Cl]$_2$ (2.1 mg, 0.043 mmol), (S)-(R)-PPF-P$^t$Bu$_2$ (3.8 mg, 0.087 mmol) and 13 (500 mg, 3.47 mmol) were added followed by addition of ethanol (4 mL) and THF (4 mL). The mixture was heated to reflux for five hours and the solvent was removed in vacuo. The resulting solid was purified by flash chromatography (20% ethyl acetate in hexanes) to give 16 as a white crystalline solid (553 mg, 84%). The ee was determined to be 97% using HPLC analysis on a CHIRALCEL OD column, λ=254 nm. Retention times in 1.5% isopropanol in hexanes were 13.6 min and 14.2 min (major). $R_f$=0.26 on silica gel (20% ethyl acetate:hexanes); mp 33° (Et$_2$O); $[\alpha]^{25}_D$=185.9° (c=9.6, CHCl$_3$); IR (KBr, cm$^{-1}$) 3601 (br), 3040 (m), 2977 (s), 1454 (s), 1396 (m), 1185 (s), 1104 (s); $^1$H NMR (400 MHz, CDCl$_3$) δ 7.59–7.57 (1H, m), 7.27–7.20 (2H, m), 7.07–7.05 (1H, m), 6.43 (1H, dd, J=9.9, 2.2 Hz), 6.01 (1H, dd, J=9.9, 2.2 Hz), 4.90 (1H, d, J=10.6 Hz), 4.18 (1H, ddd, J=10.6, 2.2, 2.2 Hz), 3.79 (1H, AB, dq, J=9.4, 6.9 Hz),), 3.58 (1H, AB, dq, J=9.4, 6.9 Hz), 2.65 (1H, s), 1.27 (3H, t, J=6.9 Hz),; $^{13}$C NMR (400 MHz, CDCl$_3$) δ 135.9, 131.9, 128.0, 127.8, 127.8, 126.1, 124.9, 80.7, 72.5, 64.6, 15.5. HRMS calcd for C$_{12}$H$_{14}$O$_2$ (M$^+$): 190.0994. Found: 190.0993.

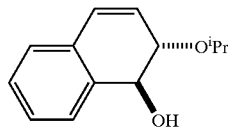

(1S,2S)-2-(Isopropoxy)-1,2-dihydro-naphthalen-1-ol (18): To a flame dried round bottom flask, [Rh(COD)Cl]$_2$ (3.5 mg, 0.007 mmol), (S)-(R)-PPF-P$^t$Bu$_2$ (7.5 mg, 0.014 mmol) and 13 (100 mg, 0.694 mmol) were added followed by addition of THF (1.5 mL) and isopropanol (1.5 mL). The mixture was heated to 80° C. for two hours and the solvent was removed in vacuo. The resulting oil was purified by flash chromatography (10% ethyl acetate in hexanes) to give 18 as a colourless oil (133.7 mg, 94%). The ee was determined to be 92% using HPLC analysis on a CHIRALCEL OD column, λ=486 nm. Retention times in 1.5% isopropanol in hexanes were 9.7 min (major) and 10.7 min. $R_f$=0.42 on silica gel (10% ethyl acetate:hexanes); $[\alpha]^{25}_D$=+154.0° (c=12.6, CHCl$_3$); IR (KBr, cm$^{-1}$) 3435(br), 3038(w), 2952(s), 1454(m), 1249(s), 1087(s); $^1$H NMR (400 MHz, CDCl$_3$) δ 7.61–7.58 (1H, m), 7.27–7.19 (2H, m), 7.06–7.04 (1H, m), 6.40 (1H, dd, J=9.9, 2.0 Hz), 5.95 (1H, dd, J=9.9, 2.2 Hz), 4.87 (1H, d, J=10.8 Hz), 4.24 (1H, ddd, J=10.8, 2.2, 2.2 Hz), 3.85 (1H, h, J=6.2 Hz), 2.98 (1H, s), 1.25 (6H, dd, J=8.8, 6.2 Hz); $^{13}$C NMR (400 MHz, CDCl$_3$) δ136.2, 132.3, 129.6, 128.0, 127.9, 127.8, 126.3, 125.0, 78.9, 73.0, 71.1, 23.5, 22.4. HRMS calcd for C$_{13}$H$_{16}$O$_2$ (M$^+$): 204.1150. Found: 204.1150.

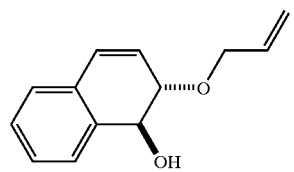

(1S,2S)-3-(1-propenyloxy)-1,2-dihydro-naphthalen-1-ol (19): To a flame dried round bottom flask, [Rh(COD)Cl]$_2$ (9.1 mg, 0.018 mmol), (S)-(R)-PPF-P$^t$Bu$_2$ (15 mg, 0.028 mmol) and 13 (1.06 g, 7.35 mmol) were added followed by addition of THF (1.5 mL) and allyl alcohol (2 mL, 29.4 mmol). The mixture was heated to 80° C. for two hours and the THF was removed in vacuo. The resulting oil was purified by flash chromatography (10% ethyl acetate in hexanes) to give 19 as a colourless oil (898 mg, 60%) which solidified on sitting. The ee was determined to be >99% using HPLC analysis on a CHIRALCEL OD column, λ=486 nm. Retention times in 1.5% isopropanol in hexanes were 15.2 min and 16.3 min (major). $R_f$=0.17 on silica gel (10% ethyl acetate:hexanes); mp 25–260 (Et$_2$O); $[\alpha]^{25}_D$=+195.1° (c=11.5, CHCl$_3$); IR (KBr, cm$^{-1}$) 3435(br), 3037(m), 2857 (s), 1454(s), 1165(s), 1083(s); $^1$H NMR (400 MHz, CDCl$_3$) δ 7.61–7.58 (1H, m), 7.27–7.20 (2H, m), 7.08–7.05 (1H, m), 6.44 (1H, dd, J=9.9, 2.0 Hz), 6.00 (1H, dd, J=9.9, 2.4 Hz), 6.00–5.92 (1H, m), 5.32 (1H, ddd, J=17.2, 3.3, 1.6 Hz), 5.21 (1H, ddd, J=10.4, 2.9, 1.3 Hz), 4.94 (1H, d, J=10.2 Hz), 4.27 (1H, ddd, J=10.3, 2.2, 2.2 Hz),), 4.23 (1H, dddd, J=12.8, 5.5, 1.5, 1.5 Hz), 4.12 (1H, dddd, J=12.8, 5.9, 1.5, 1.5 Hz), 3.09 (1H, s); $^{13}$C NMR (400 MHz, CDCl$_3$) δ135.8, 134.5, 131.8, 128.1, 127.7, 127.6, 127.4, 126.1, 125.0, 117.5, 80.1, 76.7, 72.4, 70.2. HRMS calcd for C$_{14}$H[$_4$O$_2$ (M$^+$):202.0994. Found: 202.0994.

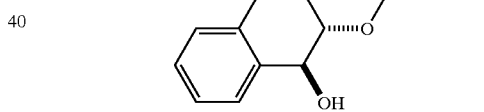

(1S,2S)-2-(2-Trimethylsilyl-ethoxy)-1,2-dihydro-naphthalen-1-ol (20): To a flame dried round bottom flask, [Rh(COD)Cl]$_2$ (4.3 mg, 0.0087 mmol), (S)-(R)-PPF-P$^t$Bu$_2$ (9.4 mg, 0.0174 mmol) and 13 (100 mg, 0.694 mmol) were added followed by addition of THF (1.25 mL) and trimethylsilylethanol (1.25 mL). The mixture was heated to reflux for two hours and the THF was removed in vacuo. The resulting oil was purified by flash chromatography (10% ethyl acetate in hexanes) to give 20 as a colourless oil (84.7 mg, 53%). The ee was determined to be 95% using HPLC analysis on a CHIRALCEL OD column, λ=486 nm. Retention times in 0.5% isopropanol in hexanes were 17.9 min and 18.5 min (major). $R_f$=0.25 on silica gel (10% ethyl acetate:hexanes); $[\alpha]^{25}_D$=+119.2° (c=13.0, CHCl$_3$); IR (KBr, cm$^{-1}$) 3447(br), 3037(m), 2972(s), 1454(m), 1381(m), 1118(s), 1078(s); $^1$H NMR (400 MHz, CDCl$_3$) δ 7.59–7.57 (1H, m), 7.28–7.21 (2H, m), 7.08–7.06 (1H, m), 6.43 (1H, dd, J=9.9, 2.0 Hz), 6.03 (1H, dd, J=9.9, 2.2 Hz), 4.89 (1H, d, J=10.6 Hz), 4.18 (1H, ddd, J=10.6, 2.2, 2.2 Hz), 3.85–3.78 (2H, m), 3.63–3.56 (2H, m), 2.79 (1H, s), 1.05–0.97 (2H, m), 0.36 (9H, m); $^{13}$C NMR (400 MHz, CDCl$_3$) δ. 135.9, 132.0, 127.9, 127.9, 127.8, 127.6, 126.1, 124.9, 80.4, 72.6, 66.5, 18.6, −1.4. HRMS calcd for $C_{15}H_{22}O_2Si$ (M+): 262.1389. Found: 262.1388.

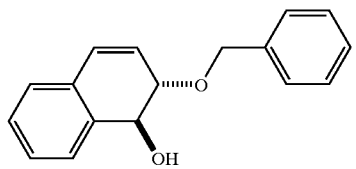

(1S,2S)-2-Benzyloxy-1,2-dihydro-naphthalen-1-ol (21): To a flame dried round bottom flask, [Rh(COD)Cl]$_2$ (9.0 mg, 0.018 mmol), (S),(R)-PPF-P$^t$Bu$_2$ (19.0 mg, 0.035 mmol), and 13 (1.00 g, 6.94 mmol) were added followed by addition of THF (1.8 mL) and benzylalcohol (3.6 mL, 34.7 mmol) and heating to 80° C. for 24 hours. The THF was then removed in vacuo and the resulting oil was purified by flash chromatography (10% ethyl acetate in hexanes) to give 21 as a crystalline solid (1.22 g, 70%). The ee was determined to be >98% using HPLC analysis on a CHIRALCEL OD column, λ=486 rim. Retention times in 1.5% isopropanol in hexanes were 29.0 min and 32.5 min (major). R$_f$=0.34 on silica gel (20% ethyl acetate:hexanes); mp 52–54° (Et$_2$O); [α]$^{25}_D$=+167.3° (c=10.0, CHCl$_3$); IR (KBr, cm$^{-1}$) 3305 (br), 3020 (w), 2876 (w), 1496 (m), 1352 (m), 1281 (m), 1169 (m), 1050 (s), 777 (s); $^1$H NMR (400 MHz, CDCl$_3$) δ 7.58–7.56 (1H, m), 7.41–7.22 (7H, m), 7.22–7.07 (1H, m), 6.46 (1H, dd, J=9.9, 2.1 Hz), 6.05 (1H, dd, J=9.9, 2.1 Hz), 4.98 (1H, d, J=10.4 Hz), 4.78 (1H, d, J=11.7 Hz), 4.63 (1H, d, J=11.7 Hz), 4.33 (1H, ddd, J=10.4, 2.2, 2.2 Hz), 2.61 (1H, s); $^{13}$C NMR (400 MHz, CDCl$_3$) δ 138.0, 135.9, 131.9, 128.5, 128.3, 128.1, 127.9, 127.9, 127.8, 127.4, 126.2, 125.1, 80.4, 72.6, 71.3. HRMS calcd for $C_{17}H_{16}O_2$ (M+): 252.1150. Found: 252.1148.

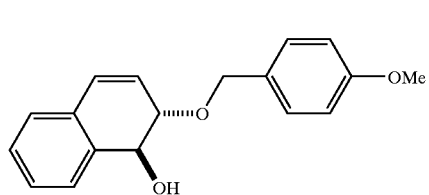

(1S,2S)-2-(4-Methoxybenzyloxy-1,2-dihydro-naphthalen-1-ol (22): To a flame dried round bottom flask, [Rh(COD)Cl]$_2$ (6.0 mg, 0.012 mmol), (S),(R)-PPF-P$^t$Bu$_2$ (13.0 mg, 0.024 mmol), and 13 (693 mg, 4.81 mmol) were added followed by addition of THF (1.5 mL) and anisyl alcohol (3.0 mL, 24.1 mmol) and heating to 80° C. for 24 hours. The THF was then removed in vacuo and the resulting oil was purified by flash chromatography (20% ethyl acetate in hexanes) to give 22 as a crystalline solid (1.18 g, 87%). The ee was determined to be 97% using HPLC analysis on a CHIRALCEL OD column, λ=486 mm. Retention times in 1.5% isopropanol in hexanes were 37.1 min and 42.1 min (major). R$_f$=0.53 on silica gel (30% ethyl acetate:hexanes); mp 63–64° (Et$_2$O); [α]$^{25}_D$=+138.5° (c=10.5, CHCl$_3$); IR (KBr, cm$^{-1}$) 3435(br), 3035(m), 2836(s), 1612(s), 1513(s), 1454(m), 1249(s), 1082(s); $^1$H NMR (400 MHz, CDCl$_3$) δ 7.59–7.57 (1H, m), 7.32 (2H, ddd, J=8.7, 2.8, 1.9 Hz), 7.28–7.22 (1H, m), ), 6.90 (2H, ddd, J=8.7, 2.8, 1.9 Hz), 6.46 (1H, dd, J=9.9, 2.1 Hz), 6.04 (1H, dd, J=9.9, 2.4 Hz), 4.96 (1H, d, J=10.1 Hz), 4.64 (1H, dd, J=57.1, 11.4 Hz), 4.32 (1H, ddd, J=10.2, 2.2, 2.2 Hz), 3.80 (1H, s), 2.96 (1H, s); $^{13}$CNMR (400 MHz, CDCl$_3$) δ 159.2, 135.9, 131.9, 129.9, 129.5, 128.1, 127.8, 127.6, 127.5, 126.1, 125.0, 113.8, 80.0, 72.5, 70.9, 55.1. HRMS calcd for $C_{17}H_{16}O_2$ (M+): 252.1150. Found: 252.1148.

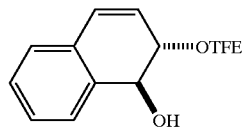

(1S,2S)-2-(2,2,2-Trifluoro-ethoxy)-1,2-dihydro-naphthalen-1-ol (17): To a flame dried round bottom flask, [Rh(COD)Cl]$_2$ (2.1 mg, 0.043 mmol), (S)-(R)-PPF-P$^t$Bu$_2$ (3.8 mg, 0.087 mmol) and 13 (500 mg, 3.47 mmol) were added followed by addition of trifluoroethanol (4 mL) and THF (4 mL). The mixture was heated to reflux for three hours and the solvent was removed in vacuo. The resulting solid was purified by flash chromatography (10% ethyl acetate in hexanes) to give 17 as a white crystalline solid (594 mg, 70%). The ee was determined to be 98% using HPLC analysis on a CHIRALCEL OD column, λ=254 nm. Retention times in 4% isopropanol in hexanes were 11.3 min (major) and 13.3 min. R$_f$=0.41 on silica gel (20% ethyl acetate:hexanes); mp 79–80° (Et$_2$O); [α]$^{25}_D$=145.4° (c=12.6, CHCl$_3$); IR (KBr, cm$^{-1}$) 3354 (br), 3036 (w), 2939 (w), 1455 (w), 1275 (s), 1169 (s), 1050(m), 977 (m); $^1$H NMR (400 MHz, CDCl$_3$) δ 7.57–7.55 (1H, m), 7.30–7.23 (2H, m), 7.10–7.08 (1H, m), 6.48 (1H, dd, J=9.9, 2.0 Hz), 5.94 (1H, dd, J=9.9, 2.4 Hz), 4.96 (1 H, d, J=2.2 Hz), 4.38 (1H, ddd, J=9.9, 2.4, 2.2 Hz), 4.03 (2H, q, $J^{H-F}$=8.6 Hz), 2.55 (1H, s); $^{13}$C NMR (400 MHz, CDCl$_3$) δ 135.5, 131.7, 129.2, 128.3, 128.1, 126.6, 125.9, 125.2, 122.4, 83.0, 72.8, 67.0 (q, $J^{C-F}$=34.4 Hz). HRMS calcd for $C_{12}H_{11}O_2F_3$ (M+): 244.0711. Found: 244.0720.

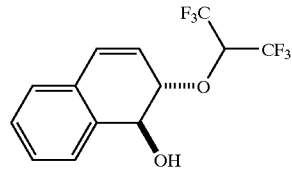

(1S,2S)-2-(2,2,2-Trifluoro-1-trifluoromethyl-ethoxy)-1,2-dihydro-naphthalen-1-ol (23): To a flame dried round bottom flask, [Rh(COD)Cl]$_2$ (1.7 mg, 0.003 mmol),(S)-(R)-PPF-P$^t$Bu$_2$ (3.8 mg, 0.007 mmol) and 13 (55 mg, 0.382 mmol) were added followed by addition of THF (2.0 mL) and hexafluoroisopropanol (240 mg, 1.74 mmol). The mixture was heated to reflux for two hours and the solvent was removed in vacuo. The resulting solid was purified by flash chromatography (10% ethyl acetate in hexanes) to give 23 as a white solid (107.1 mg, 90%). The ee was determined to be 93% using HPLC analysis on a CHIRALCEL OD column, λ=486 nm. Retention times in 1.5% isopropanol in hexanes were 11.3 min and 17.6 min (major); R$_f$=0.28 on silica gel (10% ethyl acetate:hexanes); mp 88.5–90° (Et$_2$O); [α]$^{25}_D$=+101.8° (c=10.9, CHCl$_3$); IR (KBr, cm$^{-1}$) 3191 (br), 2937 (m), 1379 (s), 1280 (s), 1247 (s), 1194 (s), 1100 (s), 954 (s), 753 (m); $^1$H NMR (400 MHz, CDCl$_3$) δ 7.55–7.53 (1H, m), 7.31–7.26 (2H, m), 7.11–7.09 (1H, m), 6.49 (1H, dd, J=9.9, 2.1 Hz), 5.92 (1H, dd, J=9.9, 2.4 Hz), 5.07 (1H, dd, J=9.7, 5.0 Hz), 4.63 (1H, ddd, J=9.9, 1.5, 1.5 Hz), 4.58 (1H, h, $J^{H-F}$=6.1 Hz), 2.50 (1H, d, J=4.2 Hz); $^{13}$C NMR (400 MHz, CDCl$_3$) δ 135.2, 131.5, 129.7, 128.5, 128.3, 126.7, 125.2, 122.9, 120.1, 85.4, 75.4 (h, $J^{C-F}$=32.2 Hz), 73.5. HRMS calcd for $C_{13}H_{10}O_2F_6$ (M+): 312.0585 Found: 312.0574.

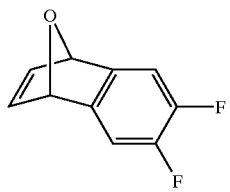

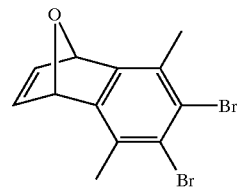

6,7-Difluoro-1,4-epoxy-1,4-dihydronaphthalene (24). To 3,4-difluoro-1,2-dibromo-benzene (0.75 g, 2.78 mmol) and furan (1 mL, 14.7 mmol) in Et$_2$O (15 mL) at −78° C. was added BuLi (1.1 mL, 2.5M in hexanes, 2.75 mmol) dropwise. The reaction was stirred for two hours at −78° C. and then was allowed to warm to room temperature. After 2 hours, the reaction mixture was quenched with water dropwise and then was poured into water. The organic layer was separated and the aqueous layer was extracted three times with Et$_2$O. The combined organic layers were washed with brine, dried over MgSO$_4$, concentrated and chromatographed (25% ethyl acetate:hexanes) on silica gel to give 24 (350 mg, 70%) as a colourless oil. R$_f$=0.21 on silica gel (20% ethyl acetate:hexanes); bp 40° C. @ 0.5 mmHg]; IR (neat, cm$^{-1}$), 3017 (M), 1624 (s), 1465 (s), 1365 (s), 1253 (s), 1190 (m), 1040 (s), 857 (s). $^1$H NMR (400 MHz, CDCl$_3$) δ 7.06 (2H, dd, $J^{H-F}$=7.7, 7.7 Hz), 7.01 (2H, s), 5.67 (2H, s); $^{13}$C NMR (400 MHz, CDCl$_3$) δ 147.2 (dd, $J^{C-F}$=247.9, 14.5 Hz), 145.1 (dd, $J^{C-F}$=4.3, 4.3 Hz), 143.1, 110.8 (m), 82.1. HRMS calcd for C$_{10}$H$_6$O (M$^+$): 180.0387. Found: 180.0394.

5,6-Dibromo-4,7-dimethyl-1,4-epoxy-1,4-dihydronaphthalene (26): To tetrabromo para-xylene (2.1 g, 5.0 mmol) and furan (4 g, 58.8 mmol) in PhMe (55 mL) at −78° C. was added BuLi (2.2 mL, 2.5M in hexanes, 5.5 mmol) dropwise. The reaction was stirred for two hours at −78° C. and the allowed to warm to rt. After 3 hours, MeOH (2 mL) was added and the reaction mixture was poured into water. The organic layer was separated and the aqueous layer was extracted three times with Et$_2$O. The combined organic layers were washed with brine, dried over MgSO$_4$, and concentrated. Flash chromatography on silca gel gave 26 (185 mg, 50%) as a white solid. The spectral data correlates well with the literature values.[22]

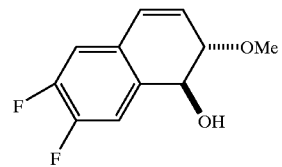

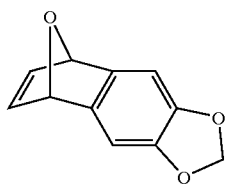

5,8-epoxy-5,8-dihydronaphtho[2,3-d][1,3]dioxole (25): To 3,4-dibromobenzo-1,3-dioxolane (1.54 g, 5.50 mmol) and furan (4 g, 58.8 mmol) in PhMe (55 mL) at −78° C. was added BuLi (2.2 mL, 2.5M in hexanes, 5.5 mmol) dropwise. The reaction was stirred for two hours at −78° C. and the allowed to warm to rt. After 3 hours, MeOH (2 mL) was added and the reaction mixture was poured into water. The organic layer was separated and the aqueous layer was extracted three times with Et$_2$O. The combined organic layers were washed with brine, dried over MgSO$_4$, and concentrated. Recrystallization from hexanes gave 25 (560 mg, 54%) as white crystals). R$_f$=0.47 on silica gel (30% ethyl acetate:hexanes); mp 111–112° C. (Et$_2$O); IR (KBr, cm$^{-1}$) 2895, 1455, 1292, 1138, 1038, 1014, 848; $^1$H NMR (400 MHz, CDCl$_3$) δ 7.02 (2H, dd, J=0.9, 0.9 Hz), 6.82 (2H, s), 5.92 (1H, d, J=1.5 Hz), 5.87 (1H, d, J=1.5 Hz), 5.62 (2H, s); $^{13}$C NMR (400 MHz, CDCl$_3$) δ 144.3, 143.3, 103.9, 101.1, 82.4. HRMS calcd for C$_{11}$H$_8$O$_2$ (M$^+$): 188.0473. Found: 188.0463.

(1S,2S)-6,7-Difluoro-2-methoxy-1,2-dihydro-naphthalen-1-ol (27): To a flame dried round bottom flask, [Rh(COD)Cl]$_2$ (2.5 mg, 0.005 mmol), (S)-(R)-PPF-P$^t$Bu$_2$ (5.4 mg, 0.010 mmol) and 24 (72 mg, 0.40 mmol) were added followed by addition of THF (1.0 mL) and methanol (1.0 mL). The mixture was heated to reflux for 1 hour. The solvents were then removed in vacuo. The resulting solid was purified by flash chromatography (20% ethyl acetate in hexanes) to give 27 as a white crystalline solid (74.9 mg, 88%). The ee was determined to be 96.4% using HPLC analysis on a CHIRALCEL OD column, λ=486 nm. Retention times in 4% isopropanol in hexanes were 8.9 min and 10.1 min (major). R$_f$=0.27 on silica gel (30% ethyl acetate:hexanes); mp 129–131° (Et$_2$O); [α]$^{25}_D$=+134.4° (c=9.3, CHCl$_3$); IR (KBr, cm$^{-1}$) 3269 (br), 2937 (w), 1597 (m),1503 (s), 1306 (s), 1103 (s), 893 (s); $^1$H NMR (400 MHz, CDCl$_3$) δ 7.40 (1H, ddd, $J^{H-F}$=10.8, 7.8 Hz, $J^{H-H}$=0.6 Hz), 6.85 (1H, dd, $J^{H-F}$=10.9, 7.8 Hz), 6.31 (1H, dd, J=10.0, 2.0 Hz), 6.05 (1H, dd. J=10.0, 2.0 Hz), 4.79 (1H, d, J=1.0 Hz), 4.05 (1H, ddd, J=11.0, 2.0, 2.0 Hz), 3.49 (3H, s), 2.94 (1H, d, J=2.2 Hz); $^{13}$C NMR (400 MHz, CDCl$_3$) δ 151.0 (d, $J^{H-F}$=12.5 Hz), 148.5 (dd, $J^{H-F}$=12.5, 2.9 Hz), 133.2 (dd, $J^{H-F}$=5.2, 3.6 Hz), 128.9 (dd, $J^{H-F}$=6.6, 4.4 Hz), 128.0 (d, $J^{H-F}$=2.2 Hz), 126.5 (dd, $J^{H-F}$=2.2, 1.5 Hz), 115.1 (d, $J^{H-F}$=18.3 Hz), 114.8 (d, $J^{H-F}$=19.8 Hz), 82.3, 72.0, 57.0. HRMS calcd for Cl H$_{10}$O$_2$F$_2$ (M$^+$): 212.0649. Found: 212.0658.

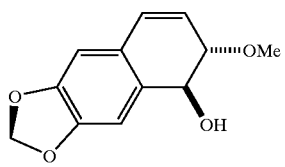

(1S,2S)-6-Methoxy-5,6-dihydro-naphtho[2,3-d][1,3] dioxol-5-ol (28): To a flame dried round bottom flask, [Rh(COD)Cl]$_2$ (1.7 mg, 0.0035 mmol), (S)-(R)-PPF-P$^t$Bu$_2$ (3.8 mg, 0.0069 mmol) and 25 (100 mg, 0.694 mmol) were added followed by addition of THF (1.0 mL) and methanol (1.0 mL) and heating to reflux for 30 minutes. The solvents were then removed in vacuo. The resulting solid was purified by flash chromatography (30% ethyl acetate in hexanes) to give 28 as a white crystalline solid (127.5 mg, 90%). The ee was determined to be 95% using HPLC analysis on a CHIRALCEL OD column, λ=486 nm. Retention times in 4% isopropanol in hexanes were 19.2 min (major) and 22.6 min. $R_f$=0.24 on silica (30% ethyl acetate:hexanes); mp 117–119° (Et$_2$O); $[\alpha]^{25}_D$=+298.70 (c=11.1, CHCl$_3$); IR (KBr, cm$^{-1}$) 3248 (br),2926 (s), 1600 (m), 1483 (s), 1260 (s), 1113 (s), 941 (s), 876 (s); $^1$H NMR (400 MHz, acetone-d) δ 7.06 (1H, s), 6.65 (1H, s), 6.35 (1H, dd, J=10.0, 2.0 Hz), 5.94 (2H, dd, J=9.8, 1.0 Hz), 5.91 (1H, dd, J=10.0, 2.5 Hz), 4.72 (1H, dt, J=9.9 Hz), 4.02 (1H, dt, J=10.3, 2.2 Hz), 3.48 (3H, s), 2.87 (1H, d, J=13.2 Hz); $^{13}$C NMR (400 MHz. acetone-d) δ 147.8, 147.6, 133.0, 128.1, 127.2, 127.2, 107.5, 107.5, 101.9, 82.1, 73.0, 57.0. HRMS calcd for C$_{12}$H$_{12}$O$_4$ (M$^+$): 220.0736. Found: 220.0684.

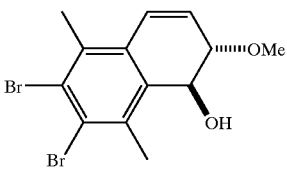

(1S,2S)-6,7-Dibromo-2-methoxy-5,8-dimethyl-1,2-dihydro-naphthalen-1-ol (29): To a flame dried round bottom flask, [Rh(COD)Cl]$_2$ (1.5 mg, 0.0029 mmol), (R)-(S)-PPF-P$^t$Bu$_2$ (3.2 mg, 0.0059 mmol) and 26 (195 mg, 0.59 mmol) were added followed by addition of trifluoroethanol (1.0 mL) and methanol (1.0 mL). The mixture was heated to reflux for 20 hours. The solvents were then removed in vacuo. The resulting solid was purified by flash chromatography (50% ethyl acetate in hexanes) to give 29 as a white crystalline solid (171.6 mg, 79%). The ee was determined to be 97% using HPLC analysis on a CHIRALCEL OD column, λ=486 nm. Retention times in 4% isopropanol in hexanes were 16.8 min (major) and 19.3 min. $R_f$=0.39 on silica gel (50% ethyl acetate:hexanes); mp 114–116° (Et$_2$O); $[\alpha]^{25}_D$=−197.1° (c=10.0, CHCl$_3$); IR (KBr, cm$^{-1}$) 3349(s), 2901 (m), 1700(w), 1532 (w), 1404(m), 1258 (m), 1081 (s), 936 (s); $^1$H NMR (400 MHz, CDCl$_3$) δ 6.96–6.93 (1H, m), 6.23–6.19 (1H, m), 4.89 (1H, s), 3.96–3.90 (1H, m), 3.38–3.35 (3H, m), 2.61–2.57 (3H, m), 2.54 (3H, s), 1.82–1.54 (1H, m); $^{13}$C NMR (400 MHz, CDCl$_3$) δ 137.3, 134.4, 133.2, 129.7, 129.5, 129.0, 128.1, 125.3, 75.3, 66.6, 56.6, 21.0, 20.6. HRMS calcd for C$_{13}$H$_{16}$O$_2$Br$_2$ (M$^+$): 361.9518. Found: 361.9335.

Example 4

Compounds Formed From Reactions Involving Carboxylate Nucleophiles

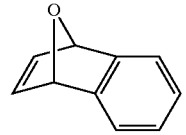

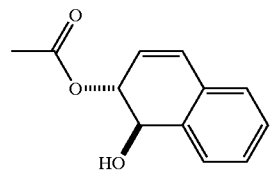

(1R*,2R*)-Acetic acid 1-hydroxy-1,2-dihydro-naphthalen-2-yl-ester (2): To a flame dried round bottom flask, [Rh(COD)Cl]$_2$ (4.3 mg, 0.008 mmol DPPF (9.6 mg, 0.017 mmol), 1 (50 mg, 1.39 mmol), and sodium acetate (142 mg, 1.74 mmol) were added followed by addition of THF (2 mL) and triethylamine hydrochloride (239 mg, 1.74 mmol). The mixture was heated at reflux for 3 hours and the solvents were removed in vacuo. The resulting mixture was purified by flash chromatography (30% ethyl acetate in hexanes) to give 2 as a crystalline solid (41 mg, 63%). $R_f$=0.26 on silica gel (20% ethyl acetate:hexanes); mp 67–68° (Et$_2$O); IR (KBr, cm$^{-1}$) $^1$H NMR (400 MHz, CDCl$_3$) δ 7.54–7.53 (1H, m), 7.29–7.24 (2H, m), 7.10–7.08 (1H, m), 6.50 (1H, dd, J=3.9, 1.3 Hz), 5.85 (1H, dd, J=9.9, 3.1 Hz), 5.59 (1H, ddd, J=9.0, 2.8, 1.9 Hz), 4.92 (1H, d, J=9.0 Hz), 2.64 (1H, s), 2.12 (3H, s); $^{13}$C NMR (400 MHz, CDCl$_3$) δ 171.3, 135.2, 131.5, 129.5, 128.3, 126.7, 126.0, 125.4, 75.3, 71.7, 21.2. HRMS calcd for C$_{12}$H$_{12}$O$_3$ (M): 204.0786. Found: 204.0791.

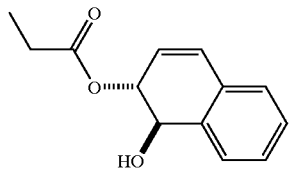

(1R*,2R*)-Propionic acid 1-hydroxy-1,2-dihydro-naphthalen-2-yl-ester (3): To a flame dried round bottom flask, [Rh(COD)Cl]$_2$ (4.3 mg, 0.0087 mmol), DPPF (9.6 mg, 0.017 mmol) and 1 (50 mg, 0.347 mmol) were added followed by addition of THF (2.5 mL), triethylamine (242 μL, 1.735 mmol) and propionic acid (130 μL, 1.735 mmol). The mixture was heated at reflux for 3 hours and the solvents were removed in vacuo. The resulting mixture was purified by flash chromatography (20% ethyl acetate in hexanes) to give 3 a white crystalline solid (50 mg, 66%). $R_f$=0.24 on silica gel (% 20 ethyl acetate:hexanes); mp 55–56° (Et$_2$O); IR (KBr, cm$^{-1}$) 3491 (br), 3048 (w), 2984 (w), 1739 (s), 1454 (m), 1363 (w), 1182 (s), 1083 (m). $^1$H NMR (400 MHz, CDCl$_3$) δ 7.55–7.52 (1H, m), 7.29–7.24 (2H, m), 7.11–7.08 (1H, m), 6.50 (1H, dd, J=10.0, 2.0 Hz), 5.85 (1H, dd, J=12.8, 2.8 Hz), 5.61 (1H, ddd, J=9.2, 2.8, 2.0 Hz), 4.93 (1H, d, J=9.2 Hz), 2.40 (2H, qd, J=7.6, 1.2 Hz), 1.16 (3H, t, J=7.6 Hz); $^{13}$C NMR (400 MHz, CDCl$_3$) δ 174.8, 135.3, 131.5, 129.4, 128.3, 128.3, 126.7, 125.9, 125.5, 75.2, 71.9, 27.7, 9.0. HRMS calcd $C_{13}H_{14}O_3$ (M$^+$): 218.0943. Found: 218.0938

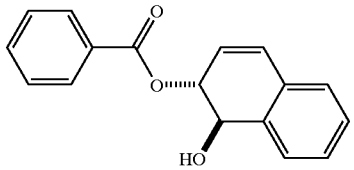

4

(1R,2R)-Benzoic acid 1-hydroxy-1,2-dihydro-naphthalen-2-yl-ester (4): To a flame dried round bottom flask, [Rh(COD)Cl]$_2$ (4.3 mg, 0.0087 mmol), (R)—(S)-BPPFA (9.6 mg, 0.017 mmol) and 1 (100 mg, 0.694 mmol) were added followed by addition of THF (4 mL), triethylamine (483 μL, 3.47 mmol) and benzoic acid (424 mg, 3.47 mmol). The mixture was heated at reflux for 6 hours and the solvents were removed in vacuo. The resulting mixture was purified by flash chromatography (20% ethyl acetate in hexanes) to give 4 a white crystalline solid (129 mg, 70%). The ee was determined to be 76% using HPLC analysis on a CHIRALCEL OD column, 10% isopropanol in hexanes, λ=254 nm. Retention times were 10.0 min (major) and 12.9 min. R$_f$=0.3 on silica gel (10% ethyl acetate:hexanes); mp 107–109° (Et$_2$O); [α]$^{25}_D$=−298.4° (c=11.3, CHCl$_3$); IR (KBr, cm$^{-1}$) 3619 (br), 3071 (w), 2977 (w), 1724 (s), 1451 (m), 1324 (m), 1265 (s), 1110 (s). $^1$H NMR (400 MHz, CDCl$_3$) δ 8.10 (2H, d, J=7.6 Hz), 7.64–7.59 (2H, m), 7.48–7.45 (2H, m), 7.34–7.32 (2H, m), 7.13–7.11 (1H, m), 6.55 (1H, d, J=10.0 Hz), 5.97 (1H, dd, J=9.8, 2.9 Hz), 5.86 (1H, ddd, J=9.8, 2.0, 2.0 Hz), 5.11 (1H, d, J=9.0 Hz), 2.84 (1H, s); $^{13}$C NMR(400 MHz, CDCl$_3$) δ 166.9, 135.3, 133.3, 131.6, 129.9, 129.8, 129.7, 128.4, 128.4, 128.4, 126.8, 126.1, 125.5, 76.1, 71.9. HRMS calcd for $C_{17}H_{14}O_3$ (M$^+$): 266.0943. Found: 266.0938.

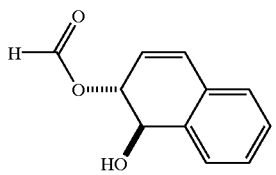

5

(1R*,2R*)-Formic acid 1-hydroxy-1,2-dihydro-naphthalen-2-yl-ester (5): To a flame dried round bottom flask, [Rh(COD)Cl]$_2$ (4.3 mg, 0.0087 mmol), DPPF (9.6 mg, 0.017 mmol), 1 (100 mg, 0.694 mmol), and ammonium formate (219 mg, 3.47 mmol), were added followed by addition of THF (5 mL). The mixture was heated at reflux for 3 hours and the solvents were removed in vacuo. The resulting mixture was purified by flash chromatography (30% ethyl acetate in hexanes) to give 5 a white crystalline solid (84 mg, 64%). R$_f$=0.25 on silica gel (30% ethyl acetate:hexanes); mp 133–1350 (Et$_2$O); IR (KBr, cm$^{-1}$) 3146 (br), 2935 (w), 1720 (s), 1482 (w), 1186 (s), 1049 (m), 968 (m); $^1$H NMR (400 MHz, CDCl$_3$) δ 8.17 (1H, d, J=0.8 Hz), 7.52–7.50 (1H, m), 7.29–7.27 (2H, m), 7.13–7.11 (1H, m), 6.54 (1H, d, J=9.6, 1.6 Hz), 5.88 (1H, dd, J=9.6, 2.8 Hz), 5.71–5.68 (1H, m), 4.96 (1H, d, J=8.8 Hz), 2.8 (1H, s); $^{13}$C NMR (400 MHz, CDCl$_3$) δ 160.9, 134.8, 131.4, 130.0, 128.5, 126.9, 126.1, 124.6, 74.8, 71.4. HRMS calcd for $C_{11}H_{10}O_3$ (M$^+$): 190.0630. Found: 190.0625.

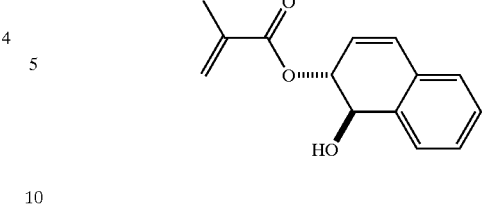

6

(1R*,2R*)-2-Methyl acrylic acid 1-hydroxy-1,2-dihydro-naphthalen-2-yl-ester (6): To a flame dried round bottom flask, [Rh(COD)Cl]$_2$ (4.3 mg, 0.0087 mmol), DPPF (9.6 mg, 0.017 mmol) and 1 (50 mg, 0.347 mmol) were added followed by addition of THF (2.5 mL), triethylamine (242 μL, 1.735 mmol) and methacrylic acid (147 μL, 1.735 mmol). The mixture was heated at reflux for 3 hours and the solvents were removed in vacuo. The resulting mixture was purified by flash chromatography (30% ethyl acetate in hexanes) to give 6 a white crystalline solid (50 mg, 63%). R$_f$=0.32 on silica gel (20% ethyl acetate:hexanes); mp 80–82° (Et$_2$O); IR (KBr, cm$^{-1}$) 3450 (br), 3030 (w), 2928 (w), 1722 (s), 1637 (m), 1454 (m), 1289 (m), 1163 (s); $^1$H NMR (400 MHz, CDCl$_3$) δ 7.56–7.55 (1H, m), 7.29–7.24 (2H, m), 7.10–7.09 (1H, m), 6.51 (1H, dd, J=9.9, 1.9 Hz), 6.15 (1H, s), 5.87 (1H, dd, J=9.9, 3.0 Hz), 5.67 (1H, ddd, J=9.3, 2.1, 2.1 Hz), 5.61 (1H, s), 5.01 (1H, dd, J=9.0, 5.7 Hz), 2.74 (1H, d, J=6.1 Hz), 1.96 (3H, s); $^{13}$C NMR (400 MHz, CDCl$_3$) δ 167.6, 135.9, 135.3, 131.5, 129.4, 128.3, 128.2, 126.6, 126.4, 125.8, 125.5, 75.9, 71.9, 18.3. HRMS calcd $C_{14}H_{12}O_2$ (M$^+$-H$_2$O): 212.0837. Found: 212.0831

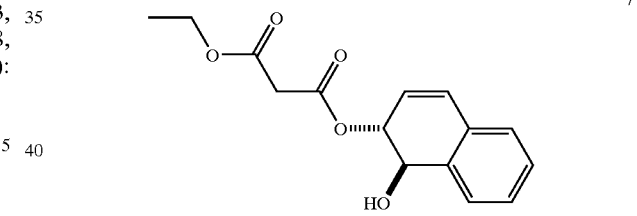

7

(1R*,2R*)-Malonic acid ethyl ester (1-hydroxy-1,2-dihydro-naphthalen-2-yl) ester (7): To a flame dried round bottom flask, [Rh(COD)Cl]$_2$ (8.6 mg, 0.017 mmol DPPF (19.2 mg, 0.035 mmol), 1 (200 mg, 1.39 mmol), ethyl malonate potassium salt (590 mg, 3.47 mmol), and triethylamine hydrochloride (478 mg, 3.47 mmol) were added followed by addition of THF (8 mL). The mixture was heated at reflux for 3 hours and the solvents were removed in vacuo. The resulting mixture was purified by flash chromatography (30% ethyl acetate in hexanes) to give 7 a colourless oil (300 mg), 79%). R$_f$=0.29 on silica gel (30% ethyl acetate:hexanes); IR (KBr, cm$^{-1}$) 3470 (br), 2983 (w), 1731 (s), 1453 (w), 1370 (m), 1150 (s), 1031 (m); $^1$H NMR (400 MHz, CDCl$_3$) δ 7.56–7.54 (1H, m), 7.27–7.21 (2H, m), 7.08–7.06 (1H, m), 6.48 (1H, dd, J=9.9, 2.1 Hz), 5.83 (1H, dd, J=9.7, 2.8 Hz), 5.70 (1H, ddd, J=9.7, 2.5, 2.2 Hz), 4.97 (1H, d, J=9.5 Hz), 4.18 (2H, q, J=7.2 Hz), 3.43 (2H, dd, J=23.6, 15.9 Hz), 3.21 (1H, s), 1.25 (3H, t, J=7.1 Hz); $^{13}$C NMR (400 MHz, CDCl$_3$) δ 167.1, 166.5, 135.0, 131.5, 129.6, 128.3, 128.1, 126.6, 125.6, 125.1, 77.0, 71.6, 61.9, 41.6, 14.0. HRMS calcd for $C_{15}H_{14}O_4$ (M$^{30}$ -H$_2$O): 258.0892. Found: 258.0899.

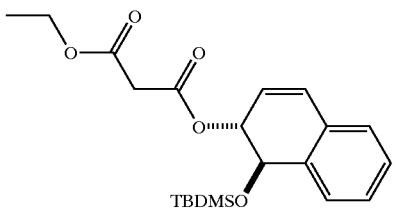

8

(1R*,2R*)-Malonic acid (1-tert-butyldimethylsiloxy-1,2-dihydro-naphthalen-2-yl) ester ethyl ester (8): To a dried round bottom flask, 7 (270 mg, 0.98 mmol), imidazole (134 mg, 1.96 mmol), dimethylaminopyridine (6 mg, 0.05 mmol) were dissolved in dichloromethane (4 mL). Tert-butyldimethylsilyl chloride (222 mg, 1.47 mmol) was then added portionwise and allowed to react for 24 hours. The reaction was then quenched with water, extracted with dichloromethane, dried over $Na_2SO_4$ and concentrated in vacuo. Flash chromatography (10% ethyl acetate in hexanes) gave a colourless oil 8 (343 mg, 90%). $R_f$=0.48 on silica gel (10% ethyl acetate:hexanes. IR(KBr, cm$^{-1}$) 2983 (w), 1731 (s), 1453 (w), 1370(m), 1150(s), 1031 (m); $^1$H NMR (400 MHz, CDCl$_3$) δ 7.41–7.39 (1H, m), 7.24–7.22 (2H, m), 7.07–7.05 (1H, m), 6.47 (1H, dd, J=9.9, 1.8 Hz), 5.83 (1H, dd, J=9.7, 2.7 Hz), 5.60 (1H, ddd, J=9.3, 2.9, 2.0 Hz), 5.00 (1H, dd, J=9.3, 0.5 Hz), 4.22–4.15 (2H, m), 3.40 (2H, dd, J=19.6, 16.0 Hz), 1.57 (1H, s), 1.25 (3H, t, J=7.1 Hz), 0.92 (9H, s), 0.13 (3H, s), 0.09 (3H, s); $^{13}$C NMR (400 MHz, CDCl$_3$) δ 166.3, 166.2, 136.2, 132.1, 129.4, 128.0, 127.9, 126.5, 125.9, 125.7, 76.4, 71.6, 61.6, 41.7, 25.8, 18.1, 14.0, −4.3, −4.5. HRMS calcd for $C_{17}H_{21}O_5Si$ (M$^+$–C$_4$H$_9$): 333.1158. Found: 333.1149.

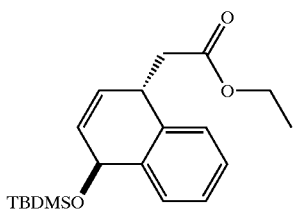

9

(1S*,2S*)-(4-Tert-butyldimethylsiloxy-1,4-dihydro-naphthalen-2-yl) acetic acid ethyl ester (9): To a dried round bottom flask, 8 (100 mg, 0.256 mmol) was dissolved in THF (4 mL). Potassium hydride (11.3 mg, 0.28 mmol) was then added portionwise and allowed to react for five minutes at room temperature. Triphenylphosphine (34.1 mg, 0.13 mmol) was then added followed by Pd(PPh$_3$)$_4$ (14.8 mg, 0.013 mmol). The reaction was then heated to reflux for two hours. The solvent was then removed in vacuo and the resulting oil purified by flash chromatography (5% ethyl acetate in hexanes) giving 9 a colourless oil (54 mg, 61%). $R_f$=0.27 on silica gel (5% ethyl acetate:hexanes); IR (KBr, cm$^{-1}$) 3036(w), 2956(s), 1735(s), 1472 (m), 1257(s), 1077 (s); $^1$H NMR (400 MHz, CDCl$_3$) δ 7.54–7.52 (1H, m), 7.30–7.23 (3H, m), 6.09 (1H, ddd, J=2.4, 4.6, 10.2 Hz), 6.02 (1H, ddd, J=10.2, 2.0, 0.5 Hz), 5.22–5.21 (1H, m), 4.15 (2H, q, J=7.2 Hz), 3.92–3.87 (1H, m), 2.62 (1H, dd, J=15.7, 5.7 Hz), 2.39 (1H, dd, J=15.2, 9.0 Hz), 1.25 (3H, t, J=7.2 Hz), 0.98 (9H, s), 0.21 (3H, s), 0.15 (3H, s); $^{13}$C NMR (400 MHz, CDCl$_3$) δ 171.7, 138.3, 136.1, 131.8, 128.2, 127.2, 127.0, 126.9, 126.6, 65.3, 60.5, 42.7, 36.5, 25.9, 18.2, 14.2, −4.2, −4.5. HRMS calcd $C_{17}H_{21}O_5Si$ (M$^+$–C$_4$H$_9$): 289.1260. Found: 289.1257

Example 5

Compounds Formed in Reactions Involving Nitrogen Nucleophiles

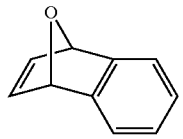

1

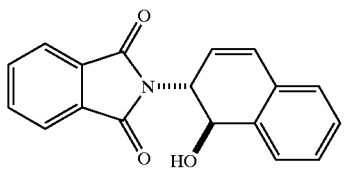

2

(1R,2R)-2-(1-hydroxy-1,2-dihydro-naphthalen-2-yl)-isoindole-1,3-dione (2): To a flame dried round bottom flask, [Rh(COD)Cl]$_2$ (5.4 mg, 0.011 mmol), (R)-(S)-BPPFA (12.2 mg, 0.022 mmol), phthalimide (510 mg, 3.47 mmol) and 1 (100 mg, 0.69 mmol) were added. THF (4 mL) was then added, followed by heating to 80° C. for 3 days. The reaction mixture was then poured in to water and extracted three times with ethyl acetate. The organic layers were combined, washed with brine dried over $Na_2SO_4$, and concentrated in vacuo. The resulting solid was purified by flash chromatography (30% ethyl acetate in hexanes) to give 2 as a white crystalline solid (103.5 mg, 52%). The ee was determined to be 74% using HPLC analysis on a CHIRALCEL OD column, λ=486 nm. Retention times in 10% isopropanol in hexanes were 21.1 min (major) and 29.1 min. $R_f$=0.36 on silica gel (30% ethyl acetate:hexanes); mp 175–176° (dec); [α]$^{25}_D$=−6.1° (c=12.9, CHCl$_3$); IR (KBr, cm$^{-1}$) 3536 (br), 3067 (w), 2921 (w), 1772 (m), 1693 (s), 1388 (s), 1084 (m), 955 (m), 719 (s); $^1$H NMR (400 MHz, CDCl$_3$) δ 7.78–7.75 (2H, m), 7.68–7.64 (2H, m), 7.57–7.55 (1H, m), 7.26–7.22 (2H, m), 7.09–7.07 (1H, m), 6.51 (1H, dd, J=9.7, 2.7 Hz), 5.84 (1H, ddd, J=9.7.2.7, 2.2 Hz), 5.48 (1H, d, J=12.8 Hz), 5.12 (1H, ddd, J=12.8, 2.5, 2.4 Hz), 2.82 (1H, s); $^{13}$C NMR (400 MHz, CDCl$_3$) δ 168.6, 137.3, 134.2, 132.6, 132.1, 128.7, 128.2, 128.1, 126.9, 126.5, 124.4, 123.5, 70.9, 55.3. HRMS calcd for $C_{18}H_{11}NO_2$ (M$^-$-H$_2$O): 273.2939. Found: 273.0793.

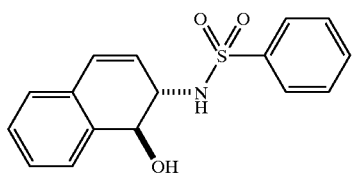

3

(1S,2S)-N-(1-Hydroxy-1,2-dihydro-naphthalen-2-yl)-benzene sulfonamide (3): To a flame dried round bottom flask, [Rh(COD)Cl]$_2$ (4.3 mg, 0.0087 mmol), (S)-(R)-PPF-P$^t$Bu$_2$ (9.4 mg, 0.0173 mmol), benzenesulfonamide (545 mg, 3.47 mmol) and 1 (100 mg, 0.69 mmol) were added. THF (2 mL) was then added, followed by heating to 80° C. for 12 hours. The reaction mixture was then poured into water and extracted three times with ethyl acetate. The organic layers were combined, washed with brine dried over $Na_2SO_4$, and concentrated in vacuo. The resulting solid was purified by flash chromatography (30% ethyl acetate in hexanes) to give 3 a white crystalline solid (223 mg, 96%). The ee was determined to be 95% by Mosher's ester formation and HPLC analysis on a CHIRALCEL OD column, λ=486 nm. Retention times in 10% isopropanol in hexanes were 26.6 min (major) and 39.4 min. $R_f$=0.22 on silica gel (30% ethyl acetate:hexanes); mp 128–130° (dec); $[\alpha]^{25}_D$=70° (c=8.3, CHCl$_3$); IR (KBr, cm$^{-1}$) 3462 (br), 3200 (m), 2957 (w), 1447 (m), 1329 (m), 1329 (m), 1164 (s), 1093 (m). $^1$H NMR (400 MHz, CDCl$_3$) δ 7.91–7.90 (2H, m), 7.62–7.58 (1H, m), 7.54–7.50 (2H, m), 7.47–7.45 (1H, m), 7.27–7.23 (2H, m), 6.40 (1H, dd, J=9.7, 1.7 Hz), 5.55 (1H, dd, J=9.7, 3.1 Hz), 5.26 (1H, s), 4.77 (1H, d, J=8.8 Hz), 4.13–4.07 (1H, m), 2.91 (1H, s); $^{13}$C NMR (400 MHz, CDCl$_3$) δ 140.2, 134.9, 132.9, 131.3, 129.5, 129.2, 128.4, 128.4, 127.1, 126.4, 126.0, 72.0, 56.3. HRMS calcd for C$_{16}$H$_{15}$NO$_3$S (M$^+$): 301.0773. Found: 301.0769.

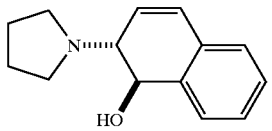

4

(1R*,7R*)-2-Pyrrolidin-1-yl-1,2-dihydro-naplthalen-1-ol (4): To a flame dried round bottom flask, [Rh(COD)Cl]$_2$ (4.3 mg, 0.009 mmol), DPPF (9.6 mg, 0.017 mmol), pyrrolidine (146 mg, 3.47 mmol), triethylamine hydrochloride (478 mg, 3.47 mmol) and 1 (125 mg, 0.865 mmol) followed by addition of THF (3 mL) and heating to reflux for 8 hours. The solvent was then removed in vacuo and the resulting mixture purified by flash chromatography (10% methanol in acetone) to give 4 a white crystalline solid (119 mg, 80° h). $R_f$=0.14 on silica gel (10% methanol in acetone); mp 97–98° (Et$_2$O); IR (KBr, cm$^{-1}$) 3496 (br), 3035 (m), 2967 (s), 1454 (m), 1193 (s), 1117 (m), 1048 (s). $^1$H NMR (400 MHz, CDCl$_3$) δ 7.56 (1H, d, J=7.1 Hz), 7.29–7.21 (2H, m), 7.08–7.06 (1H, m), 6.57 (1H, dd, J=9.9, 2.4 Hz), 6.05 (1H, dd, J=9.9, 2.4 Hz), 4.83 (1H, d, J=11.3 Hz), 3.66 (1H, ddd, J=11.3, 2.4, 2.4 Hz), 3.57 (1H, s), 2.81–2.79 (2H, m), 2.73–2.71 (2H, m), 1.84–1.80 (4H, m); $^{13}$C NMR (400 MHz, CDCl$_3$) δ 136.9, 131.8, 129.6, 127.7, 127.3, 126.1, 125.4, 124.7, 69.8, 63.3, 48.7, 23.8. HRMS calcd for C$_{14}$H$_{17}$NO (M$^+$): 215.1310. Found: 215.1314.

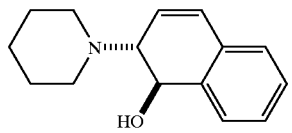

5

(1R*,2R*)-2-Piperidin-1-yl-1,2-dihydro-napbthalen-1-ol: To a flame dried round bottom flask, [Rh(COD)Cl]$_2$ (4.3 mg, 0.0087 mmol), DPPF (9.6 mg, 0.0173 mmol), piperidine hydrochloride (422 mg, 3.47 mmol), triethylamine (350 μL, 2.51 mmol) and 1 (100 mg, 0.69 mmol) were added followed by THF (3 mL) and heating to 80° C. for 12 hours. The reaction mixture was then concentrated in vacuo and purified by flash chromatography (50% ethyl acetate, 48% hexanes, 2% methanol) to give 5 a white crystalline solid (130 mg, 82%). $R_f$=0.24 on silica gel (50% ethyl acetate, 48% hexanes, 2% methanol); mp 62–640 (Et$_2$O); IR (KBr, cm$^{-1}$) 3482 (br), 3036 (w), 2937 (s), 2853 (m), 1453 (s), 1193 (s), 1109 (s), 1046 (s). $^1$H NMR (400 MHz, CDCl$_3$) δ 7.57 (1H, d, J=7.1 Hz), 7.27–7.18 (2H, m), 7.05 (1H, dd, J=6.9, 0.9 Hz), 6.49 (1H, dd, J=9.9, 2.6 Hz), 6.12 (1H, dd, J=9.9, 2.4 Hz), 4.87 (1H, d, J=12.2 Hz), 3.58 (1H, s), 3.37 (1H, ddd, J=12.2, 2.4, 2.4 Hz), 2.79–2.73 (2H, m), 2.48 (2H, m), 1.67–1.57 (4H, m), 1.56–1.46 (2H, m); $^{13}$C NMR(400 MHz, CDCl$_3$) δ 137.4, 131.8, 128.8, 127.1, 125.9, 125.2, 124.4, 68.2, 67.6, 50.4, 26.5, 24.6. HRMS calcd for C$_{15}$H$_{18}$NO (M$^+$-H): 228.1388. Found: 228.1318.

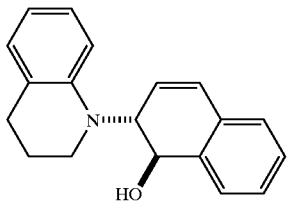

6

(1R,2R)-2-(3,4-Dihydro-2H-quinolin-1-yl)-1,2-dihydronaphthalen-1-ol: To a flame dried round bottom flask, [Rh(COD)Cl]$_2$ (4.3 mg, 0.0087 mmol), (R)-(S)-BPPFA (9.6 mg, 0.0173 mmol), tetrahydroisoquinoline (231 mg, 1.735 mmol), 1 (60 mg, 0.416 mmol) and THF (2.5 mL) were added followed by heating to reflux for 3 hours. The solvent was then removed in vacuo and the resulting oil purified by flash chromatography (5% ethyl acetate in hexanes) to give 6 a colourless oil (114.1 mg, 98%). The ee was determined to be 65% using HPLC analysis on a CHIRALCEL OD column, λ=254 nm. Retention times in 10% isopropanol in hexanes were 10.3 min (major) and 11.2 min. $R_f$=0.30 on silica gel (10% ethyl acetate:hexanes); $[\alpha]^{25}_D$=−30.0° (c=13.8, CHCl$_3$); IR (KBr, cm$^{-1}$) 3588 (br), 3037 (w), 2932 (w), 1601 (s), 1495 (m), 1190 (m). $^1$H NMR (400 MHz, CDCl$_3$) δ 7.54–7.52 (1H, m), 7.31–7.29 (2H, m), 7.17–7.14 (1H, m), 7.10–7.09 (1H, m), 7.06–7.04 (1H, m), 6.94–6.93 (1H, m), 6.68–6–67 (1H, m), 6.65 (1H, dd, J=9.4, 2.2 Hz), 5.96 (1H, dd, J=9.9, 3.3 Hz), 5.13 (1H, d, J=8.8 Hz), 4.78 (1H, ddd, J=8.8, 2.5, 2.5 Hz);3.31–3.26 (1H, m), 3.14–3.08 (1H, m), 2.81–2.80 (2H, m), 2.30 (1H, s), 1.95–1.89 (2H, m); $^{13}$C NMR (400 MHz, CDCl$_3$) δ 145.1, 136.5, 131.9, 129.7, 129.5, 128.0, 128.0, 128.0, 127.9, 127.0, 126.5, 125.9, 124.0, 116.8, 112.2, 69.5, 60.9, 44.1, 28.1, 22.5. HRMS calcd for C$_{19}$H$_{19}$NO (M$^+$): 277.1467. Found: 277.1463.

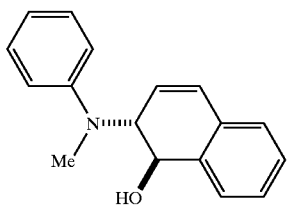

7

(1R,2R)-2-(Methyl-phenyl-amino)-1,2-dihydro-naphthalen-1-ol (7): To a flame dried round bottom flask, [Rh(COD)Cl]$_2$ (3.5 mg, 0.007 mmol), (R)-(S)-BPPFA (7.7 mg, 0.014 mmol), N-methylaniline (372 mg, 3.47 mmol), 1 (105 mg, 0.728 mmol) and THF (3 mL) were added followed by heating to reflux for 3 hours. The solvent was then removed in vacuo and the resulting oil purified by flash chromatography (5% ethyl acetate in hexanes) to give 7 a white crystalline solid (176.3 mg, 96%). The ee was determined to be 74% using HPLC analysis on a CHIRALCEL OD column, λ=254 nm. Retention times in 10% isopropanol in hexanes were 11.1 min (major) and 13.3 min. $R_f$=0.41 on silica gel (20% ethyl acetate:hexanes); mp 55–56° (Et$_2$O); $[\alpha]^{25}_D$=50.4° (c=11.8, CHCl$_3$); IR (KBr, cm$^{-1}$) 3594 (br), 3037 (m), 2884 (m), 1596 (s), 1503 (s), 1463 (m), 1186 (m), 935 (m). $^1$H NMR (400 MHz, CDCl$_3$) δ 7.57–7.55 (1H, m), 7.31–7.26 (4H, m), 7.15–7.13 (1H, m), 6.99–6.97 (2H, m), 6.84–6.81 (1H, m), 6.61 (1H, dd, J=9.8, 2.6 Hz), 5.94 (1H, dd, J=9.7, 2.9 Hz), 5.11 (1H, d, J=9.8 Hz), 4.76 (1H, ddd, J=9.7, 2.6, 2.6 Hz), 2.85 (3H, s), 2.50 (1H, s); $^{13}$C NMR (400 MHz, CDCl$_3$) δ 150.1, 136.4, 131.9, 129.6, 129.2, 128.0, 127.8, 127.7, 126.4, 125.5, 118.0, 114.5, 70.0, 63.3, 33.3. HRMS calcd for C$_{17}$H$_{17}$NO (M$^+$): 251.1310. Found: 251.1307.

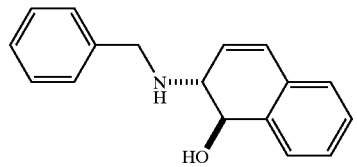

8

(1R*,2R*)-2-Benzylamino-1,2-dihydro-naphthalen-1-ol (8): To a flame dried round bottom flask, [Rh(COD)Cl]$_2$ (4.3 mg, 0.009 mmol), DPPF (9.6 mg, 0.017 mmol), benzylamine hydrochloride (279 mg, 1.74 mmol), triethylamine (242 μL, 1.74 mmol) and 1 (50 mg, 0.347 mmol) followed by addition of THF (3 mL) and heating to reflux for 3 days. The solvent was then removed in vacuo and the resulting mixture purified by flash chromatography (50% ethyl acetate in hexanes) to give 8 a white crystalline solid (26.9 mg, 31%). R$_f$=0.44 on silica gel (50% ethyl acetate, 48% hexanes, 2% methanol); mp 115–117° (dec) (Et$_2$O); IR (KBr, cm$^{-1}$) 3528 (br), 3030 (w), 2849 (w), 1455 (s), 1190 (m), 1112 (m), 1048 (m). $^1$H NMR (400 MHz, CDCl$_3$) δ 7.47–7.45 (1H, m), 7.29–7.24 (4H, m), 7.24–7.17 (3H, m), 7.02–7.01 (1H, m), 6.41 (1H, dd, J=9.7, 2.0 Hz), 6.00 (1H, dd, J=9.7, 2.5 Hz), 4.64 (1H, d, J=9.0 Hz), 3.94 (1H, AB, J=13.0 Hz), 3.75 (1H, AB, J=13.0 Hz), 3.42 (1H, ddd, J=11.0, 2.4, 2.4 Hz), 2.44 (1H, s); $^{13}$C NMR (400 MHz, CDCl$_3$) δ 139.8, 136.6, 132.1, 128.8, 128.5, 128.2, 127.9, 127.8, 127.6, 127.2, 126.1, 124.9, 72.1, 59.7, 50.7. HRMS calcd for C$_{17}$H$_{17}$NO(M$^+$): 251.1310. Found: 251.1316.

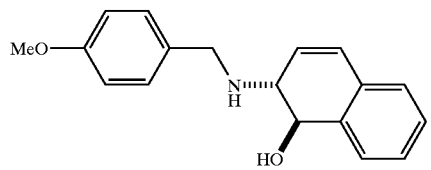

9

(1R*,2R*)-2-(4-Methoxy-benzylamino)-1,2-dihydro-naphthalen-1-ol (9): To a flame dried round bottom flask, [Rh(COD)Cl]$_2$ (4.3 mg, 0.009 mmol), DPPF (9.6 mg, 0.017 mmol), p-methoxybenzylamine (238 mg, 1.74 mmol), triethylamine hydrochloride (239 mg, 1.74 mmol) and 1 (50 mg, 0.728 mmol) followed by addition of THF (3 mL) and heating to reflux for 3 days. The solvent was then removed in vacuo and the resulting mixture purified by flash chromatography (50% ethyl acetate in hexanes) to give 9 a white crystalline solid (43 mg, 44%). R$_f$=0.27 on silica gel (50% ethyl acetate, 48% hexanes, 2% methanol); mp 96–98° (dec) (Et$_2$O); IR (KBr, cm$^{-1}$) 3528 (br), 3033 (w), 2835 (m), 1612 (m), 1512 (s), 1455 (m), 1248 (s), 1040 (m). $^1$H NMR (400 MHz, CDCl$_3$) δ 7.52–7.50 (1H, m), 7.26–7.22 (4H, m), 7.08–7.06 (1H, m), 6.85 (2H, d, J=9.0 Hz), 6.47 (1H, dd, J=9.7, 2.0 Hz), 6.05 (1H, dd, J=9.9, 2.6 Hz), 4.68 (1H, d, J=11.0 Hz), 3.95 (1H, d, J=12.9 Hz), 3.79 (3H, s), 3.75 (1H, d, J=2.9 Hz), 3.46 (1H, ddd, J=11.0, 2.4, 2.4 Hz), 3.0–2.0 (2H, s (br)); $^{13}$C NMR (400 MHz, CDCl$_3$) δ 158.7, 136.7, 132.1, 131.9, 129.4, 128.9, 127.9, 127.7, 127.5, 126.0, 124.9, 113.9, 72.1, 59.6, 55.2, 50.1. HRMS calcd for C$_{18}$H$_{19}$NO$_2$ (M$^+$): 281.1416. Found: 281.1403.

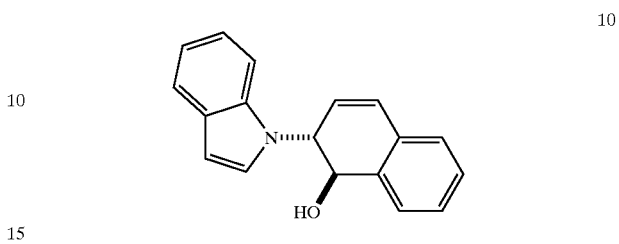

10

(1R,2R)-2-Indol-1-yl-1,2-dihydro-naphthalen-1-ol (10): To a flame dried round bottom flask, [Rh(COD)Cl]$_2$ (4.3 mg, 0.009 mmol), (R)-(S)-BPPFA (9.6 mg, 0.017 mmol), indole (407 mg, 3.47 mmol) and 1 (100 ng, 0.69 mmol) were added. THF (4 mL) was then added, followed by heating to 80° C. for 3 days. The reaction mixture was then concentrated in vacuo. The resulting oil was purified by flash chromatography (30% ethyl acetate in hexanes) to give 10 a colourless oil (147 mg, 81%). The ee was determined to be 79% using HPLC analysis on a CHIRALCEL OD column, λ=254 nm. Retention times in 10% isopropanol in hexanes were 28.5 min (major) and 30.1 min. R$_f$=0.26 on silica gel (30% ethyl acetate:hexanes); [α]$^D_{25}$=−46.7° (c=11.3, CHCl$_3$); IR (KBr, cm$^{-1}$) 3485 (br), 3059 (mn), 1592 (mn), 1455 (s), 1414 (s), 1245 (mn), 1091 (m), 908 (m); $^1$H NMR (400 MHz, CDCl$_3$) δ 8.13 (1H, s), 7.79 (1H, d, J=7.8 Hz), 7.42 (1H, d, J=7.3 Hz), 7.34–7.19 (6H, m), 6.85 (1H, d, J=2.2 Hz), 6.69 (1H, dd, J=9.5, 2.0 Hz), 6.20 (1H, dd, J=9.5, 3.8 Hz), 5.06 (1H, d, J=7.9 Hz), 4.12–4.08 (1H, m), 2.35 (1H, s); $^{13}$C NMR (400 MHz, CDCl$_3$) δ 136.5, 135.9, 132.5, 130.1, 128.0, 127.7, 126.9, 126.5, 126.4, 126.2, 122.6, 122.0, 119.3, 119.2, 113.9, 111.4, 72.7, 41.0. HRMS calcd for C$_{18}$H$_{15}$NO (M$^+$): 261.1154. Found: 261.1141.

Example 6

Compounds Formed in Reactions Involving Carbon Nucleophiles

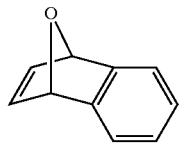

1

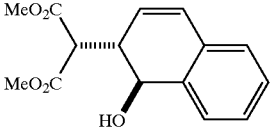

2

(1S*,2R*)-2-(Hydroxy-1,2-dihydro-naphthalen-2-yl) malonic acid dimethyl ester (2): To a flame dried round bottom flask, [Rh(COD)Cl]$_2$ (8.6 mg, 0.0174 mmol), DPPF (19.2 mg, 0.0347 mmol), dimethyl malonate (137 mg, 1.041 mmol) and 1 (100 mg, 0.694 mmol) were added followed by addition of THF (1.5 mL) and heating to 80° C. for 24 hours. The reaction mixture was then poured in to water and extracted three times with ethyl acetate. The organic layers were combined, washed with brine dried over Na$_2$SO$_4$, and concentrated in vacuo. The resulting oil was purified by flash chromatography (20% ethyl acetate in hexanes then increasing to 50% ethyl acetate in hexanes) to give 2 a colourless oil which crystallized on sitting (124.3 mg, 65%). R$_f$=0.27 on silica gel (50% ethyl acetate:hexanes); mp 65–67° (Et$_2$O); IR (neat, cm$^{-1}$) 3490 (br), 3024 (m), 2954 (s), 1744 (s), 1436 (s), 1159 (s), 1026 (s), 913 (m), 783 (s); $^1$H NMR (400 MHz, CDCl$_3$) δ 7.40–7.38 (1H, m), 7.30–7.24 (2H, m), 7.13–7.11 (1H, m), 6.57 (1H, dd, J=9.7, 1.5 Hz), 5.97 (1H, dd, J=9.7, 4.2 Hz), 4.70 (1H, dd, J=6.2, 6.2 Hz), 3.73 (3H, s), 3.70 (3H, s), 3.52 (1H, d, J=7.6 Hz), 3.37–3.35 (1H, m), 2.09 (1H, d, J=6.2 Hz); $^3$C NMR (400 MHz, CDCl$_3$) δ 168.6, 168.3, 135.4, 131.9, 128.3, 128.1, 126.8, 126.7, 70.3, 52.6, 52.6, 52.5, 42.31 . HRMS calcd for C$_{15}$H$_{16}$O$_5$ (M$^+$): 276.0998. Found: 276.0104.

Example 7

Compounds Formed in Reactions Involving Phenol Nucleophiles

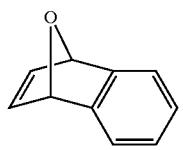

1

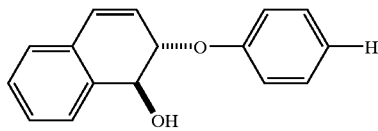

2

(1S,2S)-2-Phenoxy-1,2-dihydro-naphthalen-1-ol (2): To a flame dried round bottom flask, [Ph(COD)Cl]$_2$ (1.7 mg, 0.0035 mmol), (S)-(R)-PPF-P$^t$Bu$_2$ (3.8 mg, 0.0069 mmol, and 1 (100 m, 0.694 mmol) were added. THF (2 mL) and phenol (327 mg, 3.47 mmol) were then added followed by heating to 80° C. for 1.5 hours. The reaction mixture was then poured in to ether and washed three times with 5% aqueous Noah. The aqueous layers were combined and back extracted three times with ether. The organic layers were combined, washed with brine, dried over Na$_2$SO$_4$, and concentrated in vacuo. The resulting solid was purified by flash chromatography (20% ethyl acetate in hexanes) to give 2 as a white crystalline solid (130.7 mg, 83%). The ee was determined to be 99.2% using HPLC analysis on a CHIRALCEL OD column, λ=486 nm. Retention times in 4% isopropanol in hexanes were 15.2 min (major) and 17.8 min. F$_r$=0.26 on silica gel (10% ethyl acetate:hexanes); mp 109–110° C. (Et$_2$O); [α]$^{25}_D$=+204.7° (c=10.1, CHCl$_3$); IR (KBr, cm$^{-1}$) 3337 (br), 3029 (w), 2866 (w), 1600 (m), 1496 (s), 1249 (s), 1062 (s); $^1$H NMR (400 MHz, CDCl$_3$) δ 7.65–7.63 (1H, m), 7.33–7.25 (4H, m), 7.13–7.11 (1H, m), 7.01–6.95 (3H, m), 6.51 (1H, dd, J=9.9, 1.6 Hz), 6.02 (1H, dd, J=9.9, 2.2 Hz), 5.19 (1H, d, J=10.4 Hz), 5.11 (1H, ddd, J=10.4, 2.0, 2.0 Hz), 2.66 (1H, s); $^{13}$C NMR (400 MHz, CDCl$_3$) δ 157.4, 135.5, 131.9, 129.7, 129.0, 128.2, 128.0, 126.4, 126.1, 125.2, 121.5, 115.9, 79.1, −72.4. HRMS calcd for C$_{16}$H$_{14}$O$_2$ (M$^+$): 238.0994. Found: 238.0984.

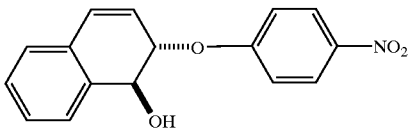

3

(1S,2S)-2-(4-nitrophenoxy)-1,2,-dihydro-naphthalen-1-ol (3): To a flame dried round-bottomed flask, [Rh(COD)Cl]$_2$ (1.7 mg, 0.0035 mmol), (S)-(R)-PPF-P$^t$Bu$_2$ (3.8 mg, 0.0069 mmol) and 1 (100 mg, 0.694 mmol) were added followed by addition of THF (2.5 mL) and 4-nitrophenol (483 mg, 3.47 mmol). The mixture was heated at 80° C. for 45 minutes, then poured into diethyl ether and extracted 3 times with 10% aqueous sodium hydroxide solution. The aqueous extracts were combined and back-extracted three times with diethyl ether. The combined ether extracts were washed with brine and dried with anhydrous sodium sulfate. The solvents were removed in vacuo, yielding a solid which was purified by flash chromatography on silica gel (30% ethyl acetate in hexanes) giving a white crystalline solid 3 (184 mg, 94%). The ee was determined to be 97% by formation of Mosher's ester. F$_r$=0.43 on silica (30% ethyl acetate:hexanes); mp 123–125° C. (dec.); [α]$^{25}_D$=+169.9° (c=10.3, CHCl$_3$); IR (KBr, cm$^{-1}$) 3351 (br), 3113 (w), 3071 (w), 2884 (w), 2843 (w), 1591 (s), 1503 (s), 1342 (s), 1295 (m), 1110 (m), 896 (w); $^1$H NMR (400 MHz, CDCl$_3$): δ 8.18 (2H, d, J=9.2 Hz), 7.62–7.60 (1H, m), 7.31–7.29 (2H, m), 7.15–7.13 (1H, m), 6.99 (2H, d, J=9.2 Hz), 6.57 (1H, d, J=9.9 Hz), 5.94 (1H, d, J=9.9 Hz), 5.20 (2H, s), 2.61 (1H, s); $^{13}$C NMR(400 MHz, CDCl$_3$): δ 162.6, 141.8, 135.0, 131.5, 130.2, 128.5, 128.4, 126.8, 126.0, 125.5, 124.1, 115.4, 79.6, 72.0.

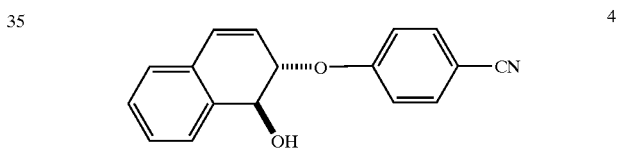

4

(1S,2S)-2-(4-Cyanophenoxy)-1,2,-dihydro-naphthalen-1-ol (4): To a flame dried round-bottomed flask, [Rh(COD) Cl]$_2$ (1.7 mg, 0.0035 mmol), (S)-(R)-PPF-P$^t$Bu$_2$ (3.8 mg, 0.0069 mmol) and 1 (100 mg, 0.694 mmol) were added followed by addition of THF (2.5 mL) and 4-cyanophenol (413 mg, 3.47 mmol). The mixture was heated at 80° C. for 5 hours, then poured into diethyl ether and extracted 3 times with 10% aqueous sodium hydroxide solution. The aqueous extracts were combined and back-extracted three times with diethyl ether. The combined ether extracts were washed with brine and dried with anhydrous sodium sulfate. The solvents were removed in vacuo, yielding a solid which was purified by flash chromatography on silica gel (30% ethyl acetate in hexanes) giving a white crystalline solid 4 (160 mg, 88%). The ee was determined to be 97% by HPLC analysis on a CHIRALCEL OD column, λ=256 nm. Retention times in 3% isopropanol in hexanes were 35.3 min and 37.7 min (major). F$_r$=0.40 on silica (30% ethyl acetate in hexanes); mp 140–141° C. (Et$_2$O); [α]$^{25}_D$=+182.3° (c=11.2, CHCl$_3$) IR (KBr, cm$^{-1}$) 3303 (b) 3050 (w) 2210 (m) 1598 (s) 1503 (s) 1238 (s) 1025 (m) 859 (m) 778 (m); $^1$H NMR (400 MHz, CDCl$_3$): δ 7.62–7.57 (3H, m), 7.33–7.27 (3H, m), 7.14–7.12 (1H, m), 6.56 (1H, dd, J=1.4, 9.7 Hz), 5.93 (1H, dd, J=1.4, 9.7 Hz), 5.20–5.13 (2H, m), 2.25 (1H, s). $^{13}$C NMR (400 MHz, CDCl$_3$): δ 160.8, 135.0, 134.2, 131.5, 130.0, 128.5, 128.3, 126.7, 125.4, 124.4, 119.0, 116.2, 104.6, 79.2, 72.0.

HRMS calcd for (M-H$_2$O)$^+$ (C$_{17}$H$_{11}$ON): 245.0841. Found: 245.0845.

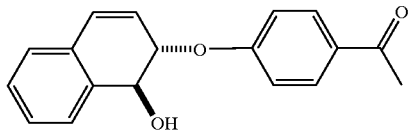

(1S,2S)-2-(4-acylphenoxy)-1,2,-dihydro-naphthalen-1-ol (5): To a flame dried round-bottomed flask, [Rh(COD)Cl]$_2$ (1.7 mg, 0.0035 mmol), (S)-(R)-PPF-P$^t$Bu$_2$ (3.8 mg, 0.0069 mmol) and 1 (100 mg, 0.694 mmol) were added followed by addition of THF (2.5 mL) and 4-hydroxyacetophenone (472 mg, 3.47 mmol). The mixture was heated at 80° C. for 2.5 hours, then poured into diethyl ether and extracted 3 times with 10% aqueous sodium hydroxide solution. The aqueous extracts were combined and back-extracted three times with diethyl ether. The combined ether extracts were washed with brine and dried with anhydrous sodium sulfate. The solvents were removed in vacuo, yielding a solid which was purified by flash chromatography on silica gel (30% ethyl acetate in hexanes) giving a white crystalline solid 5 (177 mg, 91%). The ee was determined to be >99% by formation of Mosher's ester; R$_f$=0.28 on silica (30% ethyl acetate in hexanes); mp 124–126° C. (Et$_2$O); [α]$^{25}_D$=+153° (c=9.8, CHCl$_3$). IR (KBr, cm$^{-1}$) 3367 (b), 3069 (w), 2916 (w), 1668 (s), 1601 (s), 1265 (s), 1053 (m), 835 (m), 779 (m); $^1$H NMR (400 MHz, CDCl$_3$): δ 7.94 (2H, d, J=8.8 Hz), 7.66–7.64 (1H, m), 7.34–7.27 (2H, m), 7.16–7.14 (1H, m), 6.98 (2H, d, J=8.8 Hz), 6.57 (1H, d, J=9.9 Hz), 5.99 (1H, d, J=9.9 Hz), 5.21 (2H, s), 2.85 (1H, s), 2.56 (3H, s); $^{13}$C NMR (400 MHz, CDCl$_3$): δ 196.8, 161.4, 135.3, 131.7, 130.7, 130.6, 129.6, 128.3, 128.1, 126.6, 125.4, 125.0, 115.2, 79.0, 72.0, 26.3. HRMS calcd for (M-H$_2$O)$^+$ (C$_{18}$H$_{14}$O$_2$): 262.0994. Found: 262.0989.

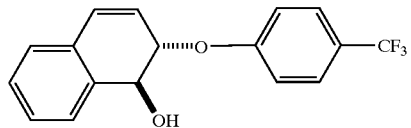

(1S,2S)-2-(4-Trifluoromethylphenoxy)-1,2,-dihydro-naphthalen-1-ol (6): To a flame dried round-bottomed flask, [Rh(COD)Cl]$_2$ (1.7 mg, 0.0035 mmol), (S)-(R)-PPF-P$^t$Bu$_2$ (3.8 mg, 0.0069 mmol) and 1 (100 mg, 0.694 mmol) were added followed by addition of THF (2.5 mL) and 4-trifluoromethylphenyl (563 mg, 3.47 mmol). The mixture was heated at 80° C. for 8 hours, then poured into diethyl ether and extracted 3 times with 10% aqueous sodium hydroxide solution. The aqueous extracts were combined and back-extracted three times with diethyl ether. The combined ether extracts were washed with brine and dried with anhydrous sodium sulfate. The solvents were removed in vacuo, yielding a solid which was purified by flash chromatography on silica gel (10% ethyl acetate in hexanes) to give a white crystalline solid 6 (184 mg, 87%). The ee was determined to be 95% by HPLC analysis on a CHIRALCEL OD column, λ=486 nm. Retention times in 4% isopropanol in hexanes were 14.8 min and 17.3 min (major). R$_f$=0.46 on silica (20% ethyl acetate in hexanes); mp 118–119° C. (Et$_2$O); [α]$^{25}_D$=+1780 (c=9.6, CHCl$_3$). IR (KBr, cm$^{-1}$) 3360 (br), 3061 (w), 2874 (w), 1617 (m), 1518 (m), 1326 (s), 1103 (s), 1051 (m), 839 (m), 782 (m), 745 (w); $^1$H NMR (400 MHz, CDCl$_3$): δ 7.63–7.54 (1H; m), 7.55 (2H, d, J=8.6 Hz), 7.33–7.24 (2H, m), 7.14–7.12 (1H, m), 7.01 (2H, d, J=8.6 Hz), 6.55 (1H, dd, J=1.6, 9.9 Hz), 5.97 (1H, dd, J=2.0, 9.9 Hz), 5.21–5.13 (2H, m), 2.47 (1H, d, J=3.6 Hz); $^{13}$C NMR (400 MHz, CDCl$_3$): δ 159.9, 135.2, 131.7, 129.6, 128.4, 128.2, 127.1 (q, J$^{C-F}$=3.6 Hz), 126.6, 125.4, 124.9, 123.4 (d, J$^{C-F}$=33.0 Hz), 122.9 (d, J$^{C-F}$=271.6 Hz), 115.6, 79.1, 72.1; HRMS calcd for (M$^+$) (C$_{17}$H$_{13}$O$_2$F$_3$): 306.0868. Found: 306.0852.

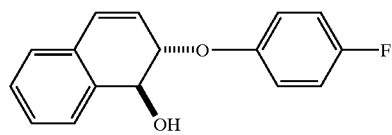

(1S,2S)-2-(4-Fluorophenoxy)-1,2,-dihydro-naphthalen-1-ol (7): To a flame dried round-bottomed flask, [Rh(COD) Cl]$_2$ (1.7 mg, 0.0035 mmol), (S)-(R)-PPF-P$^t$Bu$_2$ (3.8 mg, 0.0069 mmol) and 1 (100 mg, 0.694 mmol) were added followed by addition of THF (2.5 mL) and 4-fluorophenol (389 mg, 3.47 mmol). The mixture was heated at 80° C. for 5 hours, then poured into diethyl ether and extracted 3 times with 10% aqueous sodium hydroxide solution. The aqueous extracts were combined and back-extracted three times with diethyl ether. The combined ether extracts were washed with brine and dried with anhydrous sodium sulfate. The solvents were removed in vacuo, yielding a solid which was purified by flash chromatography on silica gel (10% ethyl acetate in hexanes) giving a white crystalline solid 7 (163 mg, 92%). The ee was determined to be 97% by HPLC analysis on a CHIRALCEL OD column, λ=486 nm). Retention times in 1.5% isopropanol in hexanes were 28.1 min (major) and 29.5 min. R$_f$=0.39 on silica (20% ethyl acetate in hexanes); mp 127–129° C. (Et$_2$O); [α]$^{25}_D$=+216° (c=9.5, CHCl$_3$). IR (KBr, cm$^{-1}$) 3309 (b), 3071 (w), 2864 (w), 1504 (s), 1284 (m), 1052 (s), 781 (s), 692 (m); $^1$H NMR (400 MHz, CDCl$_3$): δ 7.63–7.61 (1H, m), 7.31–7.26 (2H, m), 7.12–7.10 (1H, m), 7.00–6.95 (2H, m), 6.92–6.88 (2H, m), 6.51 (1H, dd, J=2.1, 9.9 Hz), 5.98 (1H, dd, J=2.2, 9.9 Hz), 5.15 (1H, dd, J=3.6, 10.0 Hz), 5.01 (1H, ddd, J=2.1, 2.1, 10.1 Hz), 2.54 (1H, d, J=3.8 Hz); $^{13}$C NMR (400 MHz, CDCl$_3$): δ 157.6 (d, J$^{C-F}$=239 Hz), 156.4, 153.4, 135.4, 131.8, 129.1, 128.2, 126.5, 125.7, 125.2, 117.5 (d, J$^{C-F}$=8 Hz), 116.1 (d, J$^{C-F}$=23.5 Hz);. HRMS calcd for (M$^+$) (C$_{16}$H$_{13}$O$_2$F): 256.0810. Found: 256.0911.

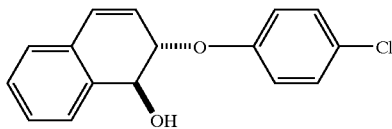

(1S,2S)-2-(4-Chlorophenoxy)-1,2,-dihydro-naphthalen-1-ol (8): To a flame dried round-bottomed flask, [Rh(COD) Cl]$_2$ (1.7 mg, 0.0035 mmol), (S)-(R)-PPF-P$^t$Bu$_2$ (3.8 mg, 0.0069 mmol) and 1 (100 mg, 0.694 mmol) were added followed by addition of THF (2.5 mL) and 4-chlorophenol (446 mg, 3.47 mmol). The mixture was heated at 80° C. for 6 hours, then poured into diethyl ether and extracted 3 times with 10% aqueous sodium hydroxide solution. The aqueous extracts were combined and back-extracted three times with diethyl ether. The combined ether extracts were washed with brine and dried with anhydrous sodium sulfate. The solvents were removed in vacuo, yielding a solid which was purified by flash chromatography on silica gel (5% ethyl acetate in hexanes) giving a white crystalline solid 8 (169 mg, 89%). The ee was determined to be 92% by formation of Mosher's ester. $R_f$=0.47 on silica (20% ethyl acetate in hexanes); mp 125–125.5° C. (Et$_2$O); $[\alpha]^{25}_D$=+150° (c=10.6, CHCl$_3$). IR (KBr, cm$^{-1}$) 3302 (br), 3064 (w), 2874 (w), 1590 (m), 1489 (s), 1362 (w), 1230 (s), 1052 (m), 890 (w), 846 (m), 778 (s), 663 (m); $^1$H NMR (400 MHz, CDCl$_3$): δ 7.65–7.64 (1H, m), 7.33–7.26 (4H, m), 7.16–7.13 (1H, m), 6.91(1H, ddd, J=2.0, 2.0, 8.9 Hz), 6.55 (1H, dd, J=1.8, 9.9 Hz), 5.99 (1H, dd, J=2.2, 9.9 Hz), 5.19 (1H, dd, J=3.8, 10.0 Hz), 5.07 (1H, ddd, J=2.0, 2.0, 10.1 Hz), 2.56 (1H, d, J=4.0 Hz); $^{13}$C NMR (400 MHz, CDCl$_3$): δ 155.8, 135.2, 131.7, 129.5, 129.3, 128.2, 128.1, 126.5, 126.2, 125.3, 125.2, 116.9, 79.2, 72.1. HRMS calcd for (M-H$_2$O)$^+$ (C$_{16}$H$_{11}$OCl): 254.0498. Found: 254.0499.

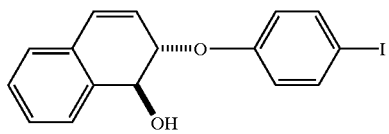

(1S,2S)-2-(4-Iodophenoxy)-1,2,-dihydro-naphthalen-1-ol (9): To a flame dried round-bottomed flask, [Rh(COD)Cl]$_2$ (1.7 mg, 0.0035 mmol), (S)-(R)-PPF-P$^t$Bu$_2$ (3.8 mg, 0.0669 mmol) and 1 (100 mg, 0.694 mmol) were added followed by addition of THF (2.5 mL) and 4-iodophenol (763 mg, 3.47 mmol). The mixture was heated at 80° C. for 12 hours, then poured into diethyl ether and extracted 3 times with 10% aqueous sodium hydroxide solution. The aqueous extracts were combined and back-extracted three times with diethyl ether. The combined ether extracts were washed with brine and dried with anhydrous sodium sulfate. The solvents were removed in vacuo, yielding a solid which was purified by flash chromatography on silica gel (10% ethyl acetate in hexanes) as a white crystalline solid 9 (193 mg, 73%). The ee was determined by deiodinating 9 (40 m; 0.11 mmol) by reaction with t-BuLi (0.32 mL, 1.7M) in diethyl ether (2 mL) at −78° C. followed by quenching with isopropanol. Extraction with ether from water, washing with brine, drying over anhydrous sodium sulfate and removal of the solvents in vacuo gave a white crystalline solid (24 mg, 92%). The ee was determined to be 98% by HPLC analysis on a CHIRALCEL OD column, λ=256 nm. Retention times in 4% isopropanol in hexanes were 15.2 min (major) and 17.9 min; $R_f$=0.44 on silica (20% ethyl acetate in hexanes); mp 160–162° C. (Et$_2$O); $[\alpha]^{25}_D$=+107° (c=9.7, CHCl$_3$). IR (KBr, cm$^{-1}$) 3264 (br), 3050 (w), 2926 (w), 2843 (w), 1581 (m), 1485 (s), 1388 (w), 1279 (m), 1246 (s), 1046 (m), 824 (m), 780 (m), 571 (w); $^1$H NMR (400 MHz, CDCl$_3$): δ 7.63–7.61 (1H, m). 7.58–7.55 (2H, m), 7.30–7.27 (2H, m), 7.13–7.11 (1H, m), 6.73 (2H, ddd, J=2.2, 2.2, 9.0 Hz), 6.52 (1H, dd, J=1.8, 9.8 Hz), 5.96 (1H, dd, J=2.2, 9.8 Hz), 5.16 (1H, d, J=10.0 Hz), 5.05 (1H, ddd, J=2.0, 2.0, 10.0 Hz), 2.54 (1H, s); $^{13}$C NMR (400 MHz, CDCl$_3$): δ 157.3, 138.5, 135.3, 131.7, 129.4, 128.3, 128.1, 126.6, 125.3, 125.3, 118.1, 83.6, 79.2, 72.2. HRMS calcd for (M-H$_2$O)$^+$ (C$_{16}$H$_{11}$OI): 345.9855. Found: 345.9849.

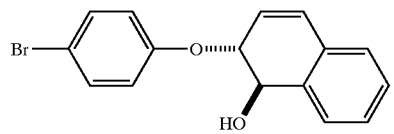

(1R,2R)-2-(4-Bromo-phenoxy)-1,2-dihydro-naphthalen-1-ol: To a flame dried round bottom flask, [Rh(COD)Cl]$_2$ (2.1 mg, 0.0043 mmol), (R)-(S)-PPF-P$^t$Bu$_2$ (4.6 mg, 0.0085 mmol, and 1 (122 mg, 0.85 mmol) were added.). THF (2 mL) and p-bromophenol (734 mg, 4.245 mmol) were then added followed by heating to 80° C. for 1.5 hours. The reaction mixture was then poured in to ether and washed three times with 5% aqueous NaOH. The aqueous layers were combined and back extracted three times with ether. The organic layers were combined, washed with brine, dried over Na$_2$SO$_4$, and concentrated in vacuo. The resulting solid was purified by flash chromatography (20% ethyl acetate in hexanes) to give 10 a white crystalline solid (239.7 mg, 90%). The ee was determined by debrominating 10 (44 mg, 0.139 mmol) by reaction with t-BuLi (0.2 mL, 1.7M) in ether (2 mL) at −78° C. followed by quenching with isopropanol. Extraction with ether from water, washing with brine, drying over Na$_2$SO$_4$ and concentration gave a white crystalline solid 2 (31.5 mg, 95%). The ee was determined to be 96.8% by HPLC analysis on a CHIRALCEL OD column, λ=486 nm. Retention times in 4% isopropanol in hexanes were 15.2 min and 17.5 min (major). $R_f$=0.26 on silica gel (10% ethyl acetate:hexanes); mp 145–146° (Et$_2$O); $[\alpha]^{25}_D$=−135.70 (c=10.2, CHCl$_3$); IR (KBr, cm$^{-1}$) 3290 (br), 3060 (m), 2870 (w), 1583 (m), 1484 (s), 1227 (s), 1052 (m), 980 (s), 776 (s); $^1$H NMR (400 MHz, CDCl$_3$) δ 7.70–7.65 (1H, m), 7.44–7.42 (2H, m), 7.35–7.32 (2H, m), 7.18–7.16 (1H, m), 6.88–6.86 (2H, m), 6.56 (1H, dd, J=10.0, 2.0 Hz), 6.00 (1H, dd, J=9.7, 2.2 Hz), 5.20 (1H, dd, J=9.7, 3.6 Hz), 5.09 (1H, ddd, J=10.0, 2.0, 2.0 Hz), 2.70 (1H, d, J=3.9 Hz); $^{13}$C NMR (400 MHz, CDCl$_3$) δ 156.5, 135.3, 132.5, 131.7, 129.3, 128.3, 128.1, 126.5, 125.3, 117.6, 113.7, 79.4, 72.2. HRMS calcd for C$_{16}$H$_{11}$OBr (M-H$_2$O)$^+$ 297.9994. Found: 297.9995.

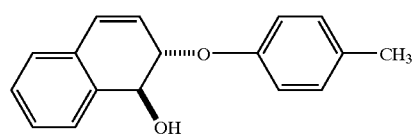

(1S,2S)-2-(4-Methylphenoxy)-1,2,-dihydro-naphthalen-1-ol (11): To a flame dried round-bottomed flask, [Rh(COD)Cl]$_2$ (1.7 mg, 0.0035 mmol), (S)-(R)-PPF-P$^t$Bu$_2$ (3.8 mg, 0.0069 mmol) and 1 (50 mg, 0.347 mmol) were added followed by addition of THF (2.5 mL) and p-cresol (188 mg, 1.74 mmol). The mixture was heated at 80° C. for 24 hours, then poured into diethyl ether and extracted 3 times with 10% aqueous sodium hydroxide solution. The aqueous extracts were combined and back-extracted three times with diethyl ether. The combined ether extracts were washed with brine and dried with anhydrous sodium sulfate. The solvents were removed in vacuo, yielding a solid which was purified by flash chromatography on silica gel (5% ethyl acetate in hexanes) giving a white crystalline solid 11 (57 mg, 65%). The ee was determined to be 91% by HPLC analysis on a CHIRALCEL OD column, λ=256 nm. Retention times in 1% isopropanol in hexanes were 33.8 min (major) and 37.1 min. $R_f$=0.49 on silica (20% ethyl acetate in hexanes); mp 80–81° C. (Et$_2$O); [α]$^{25}_D$=+145° (c=12.1, CHCl$_3$). IR (KBr, cm$^{-1}$) 3303 (br), 3050 (w), 2210 (m), 1598 (s), 1503 (s), 1238 (s), 1025 (m), 859 (m), 778 (m); $^1$H NMR (400 MHz, CDCl$_3$): δ 7.67–7.65 (1H, m), 7.33–7.28 (2H, m), 7.14–7.11 (3H, m), 6.88 (2H, d, J=8.4 Hz), 6.51 (1H, dd, J=1.8, 9.9 Hz), 6.04 (1H, dd, J=2.0, 9.9 Hz), 5.20 (1H, dd, J=1.6, 10.2 Hz), 5.09 (1H, ddd, J=1.8, 1.8, 10.2 Hz), 2.87 (1H, d, J=2.7 Hz), 2.33 (3H, s). $^{13}$C NMR (400 MHz, CDCl$_3$): δ 155.0, 135.4, 131.8, 130.7, 130.1, 128.8, 128.1, 127.9, 126.4, 126.2, 125.1, 115.6, 79.0, 72.3, 20.5. HRMS calcd for (M$^+$) (C$_{17}$H$_{16}$O$_2$): 252.1150. Found: 252.1140.

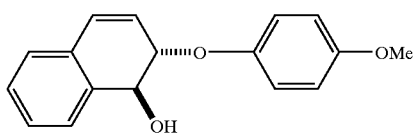

12

(1S,2S)-2-(4-Methoxyphenoxy)-1,2,-dihydro-naphthalen-1-ol (12): To a flame dried round-bottomed flask, [Rh(COD)Cl]$_2$ (1.7 mg, 0.0035 mmol), (S)-(R)-PPF-P$^t$Bu$_2$ (3.8 mg, 0.0069 mmol) and 1 (100 mg, 0.694 mmol) were added followed by addition of THF (2.5 mL) and 4-methoxyphenol (431 mg, 3.47 mmol). The mixture was heated at 80° C. for 6 hours, then poured into diethyl ether and extracted 3 times with 10% aqueous sodium hydroxide solution. The aqueous extracts were combined and back-extracted three times with diethyl ether. The combined ether extracts were washed with brine and dried with anhydrous sodium sulfate. The solvents were removed in vacuo, yielding a solid which was purified by flash chromatography on silica gel (10% ethyl acetate in hexanes) as a white crystalline solid 12 (159 mg, 85%). The ee was determined to be 95% by HPLC analysis on a CHIRALCEL OD column, λ=256 nm. Retention times in 4% isopropanol in hexanes were 22.1 min (major) and 25.9 min. $R_f$=0.33 on silica (20% ethyl acetate in hexanes); mp 91–92° C. (Et$_2$O); [α]$^{25}_D$=+129° (c=9.9, CHCl$_3$); IR (KBr, cm$^{-1}$) 3349 (br), 3050 (w), 2822 (w), 1508 (s), 1233 (s), 1046 (m), 825 (m), 751 (m), 695 (w); $^1$H NMR (400 MHz, CDCl$_3$): δ 7.66–7.64 (1H, m), 7.30–7.27 (2H, m), 7.12–7.10 (1H, m), 6.91 (2H, ddd, J=2.3, 2.3, 9.1 Hz), 6.84 (2H, ddd, J=2.4, 2.4, 9.2 Hz), 6.49 (1H, dd, J=2.0, 9.9 Hz), 6.02 (1H, dd, J=2.4, 9.9 Hz), 5.17 (1H, dd, J=3.3, 10.1 Hz), 5.02 (1H, ddd, J=2.0, 2.0, 10.3 Hz), 3.77 (3H, s), 3.12 (1H, d, J=3.4 Hz). $^{13}$C NMR (400 MHz, CDCl$_3$): δ 154.3, 151.2, 135.5, 131.9, 128.7, 128.1, 127.9, 126.4, 126.3, 125.2, 117.2, 114.8, 80.0, 72.4, 55.7. HRMS calcd for (M$^+$) (C$_{17}$H$_{14}$O$_2$): 250.0994. Found: 250.1006.

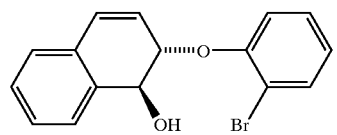

13

(1S,2S)-2-(2-Bromophenoxy)-1,2,-dihydro-naphthalen-1-ol (13): To a flame dried round-bottomed flask, [Rh(COD)Cl]$_2$ (1.7 mg, 0.0035 mmol), (S)-(R)-PPF-P$^t$Bu$_2$ (38 mg, 0.0069 mmol) and 1 (100 mg, 0.694 mmol) were added followed by addition of THF (2.5 mL) and 2-bromophenol (0.40 mL, 3.47 mmol). The mixture was heated at 80° C. for 24 hours, then poured into diethyl ether and extracted 3 times with 10% aqueous sodium hydroxide solution. The aqueous extracts were combined and back-extracted three times with diethyl ether. The combined ether extracts were washed with brine and dried with anhydrous sodium sulfate. The solvents were removed in vacuo, yielding a solid which was purified by flash chromatography on silica gel (5% ethyl acetate in hexanes) as a white crystalline solid 13 (75 mg, 37%). The ee was determined to be 81% by HPLC analysis on a CHIRALCEL OD column, λ=486 nm. Retention times in 1.5% isopropanol in hexanes were 22.8 min and 32.1 min (major). $R_f$=0.44 on silica (20% ethyl acetate in hexanes); mp 120–122° C. (Et$_2$O); [α]$^{25}_D$=+2540 (c=9.2, CHCl$_3$). IR (KBr, cm$^{-1}$) 3341 (br), 3071 (w), 2884 (w), 1581 (m), 1472 (s), 1358 (m), 1237 (s), 1028 (s), 987 (s), 780 (s), 689 (m), 569 (m); $^1$H NMR (400 MHz, CDCl$_3$): δ 7.67 (1H, d J=6.8 Hz), 7.58 (1H, dd, J=1.5, 7.9 Hz), 7.33–7.23 (3H, m), 7.14–7.12 (1H, m), 6.95(1H, dd, J=1.1, 8.2 Hz), 6.92–6.87 (1H, m), 6.52 (1H, dd, J=2.0, 9.9 Hz), 6.06 (1H, dd, J=1.8, 9.9 Hz), 5.32 (1H, d, J=11.0 Hz), 5.10 (1H, ddd, J=2.0, 2.0, 11.0 Hz), 2.85 (1H, d, J=3.2 Hz). $^{13}$C NMR (400 MHz, CDCl$_3$): δ 154.3, 135.4, 133.6, 131.8, 129.1, 128.6, 128.3, 128.0, 126.4, 126.0, 124.9, 122.9, 115.6, 113.5, 82.2, 72.5. HRMS calculated for (M-H$_2$O)$^+$ (C$_{16}$H$_{11}$OBr): 297.9993. Found: 297.9976.

II. Compounds Made Using Azabicyclics

Example 8

Azabicyclic Starting Materials

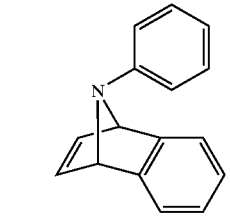

1

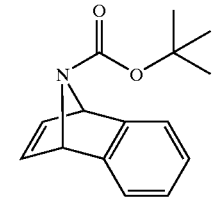

2

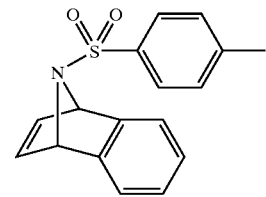

3

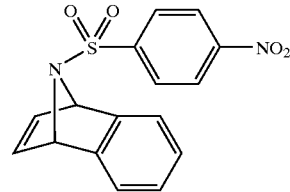

4

-continued

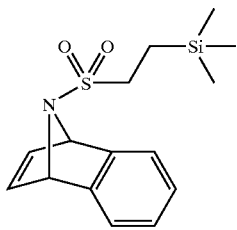
5

Example 9

Compounds Formed in Reactions Involving Alcohols

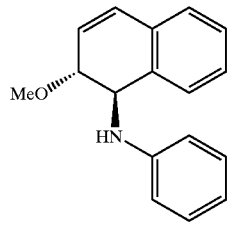
6

To a round bottomed flask was added 1 (44 mg, 0.2 mmol), [Rh(COD)Cl]$_2$ (2.5 mg, 0.005 mmol), and DPPF (5.5 mg, 0.01 mmol). THF (1 ml) and MeOH (1 ml) were then added and the solution heated to reflux for 6 hours. The reaction mixture was then concentrated and chromatographed to give 6 (28 mg, 56%) a colourless oil. $^1$H NMR (400 MHz, CDCl$_3$) δ 7.35 (1H, d, J=7.2 Hz), 7.28–7.13 (4H, m), 6.76–6.68 (4H, m), 6.64 (1H, d, J=9.9 Hz), 6.11 (1H, dd, J=4.0, 9.7 Hz), 5.73 (1H, d, J=6.0 Hz), 4.21 (1H, dd, J=4.3, 4.3 Hz), 3.82 (1H, s), 3.42 (3H, s); $^{13}$C NMR (400 MHz, CDCl$_3$) δ 147.1, 135.2, 132.0, 129.9, 129.4, 129.3, 128.4, 128.3, 128.1, 127.0, 126.5, 126.5, 75.8, 56.1, 55.8. HRMS calcd for C$_{17}$H$_{17}$NO (M$^+$): 251.1310. Found: 251.1315.

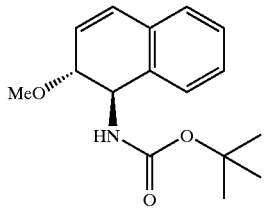
7

To a round bottomed flask was added 2 (49 mg, 0.2 mmol), [Rh(COD)Cl]$_2$ (2.5 mg, 0.005 mmol), and DPPF (5.5 mg, 0.01 mmol). THF (1 ml) and MeOH (1 ml) were then added and the solution heated to reflux for 48 hours. The reaction mixture was then concentrated and chromatographed (10% ethyl acetate:hexanes) to give 7 (41 mg, 74%) a white solid. The regiochemistry and relative stereochemistry was proven by X-ray crystal diffraction. R$_f$=0.25 on silica gel (10% ethyl acetate:hexanes); $^1$H NMR (400 MHz, CDCl$_3$) δ 7.35–7.34 (1H, m), 7.25–7.20 (2H, m), 7.10–7.08 (1H, m), 6.58 (2H, d, J=9.7 Hz), 6.07 (1H, dd, J=4.3, 9.7 Hz), 4.98 (1H, dd, J=5.5, 8.0 Hz), 4.61 (1H, d, J=7.7 Hz), 4.00 (1H, dd, J=4.6, 4.6 Hz), 3.45 (3H, s), 1.44 (9H, s); $^{13}$C NMR (400 MHz, CDCl$_3$) δ 155.3, 134.1, 131.9, 130.0, 130.0, 128.3, 128.3, 127.0, 125.9, 79.6, 56.3, 51.3, 28.4. HRMS calcd for C$_{16}$H$_{21}$NO$_3$ (M$^+$): 275.1521. Found: 275.1518.

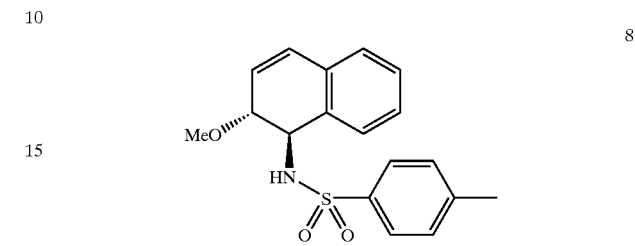
8

To a round bottomed flask was added 3 (60 mg, 0.2 mmol), [Rh(COD)Cl]$_2$ (2.5 mg, 0.005 mmol), and DPPF (5.5 mg, 0.01 mmol). THF (1 ml) and MeOH (1 ml) were then added and the solution heated to reflux for 9 hours (Note: 3 and 8 nearly co-spot by TLC but 8 stains red with permanganate whereas 3 stains white). The reaction mixture was then concentrated and chromatographed to give 8 (60 mg, 91%) a crystalline solid. mp 128–129° C.; $^1$H NMR (400 MHz, CDCl$_3$) δ 7.78 (2H, d, J=8.0 Hz), 7.33 (2H, d, J=7.9 Hz), 7.25–7.18 (1H, m), 7.11–7.04 (2H, m), 6.80 (2H, d, J=7.5 Hz), 6.60 (1H, d, J=9.7 Hz), 6.06 (1H, dd, J=5.1, 9.2 Hz), 4.50 (2H, s (br)), 3.98 (1H, s), 2.29 (3H, s), 2.47 (3H, s); $^{13}$C NMR (400 MHz, CDCl$_3$) δ 144.9, 137.2.132.4, 131.7, 130.3, 129.6, 128.8, 128.4, 127.3, 124.9, 77.2, 56.5, 54.1, 21.6. Anal. Calcd for C$_{18}$H$_{19}$NO$_3$S: C, 65.63; H, 5.81; N, 4.25. Found: C, 65.74; H, 5.89; N, 4.19.

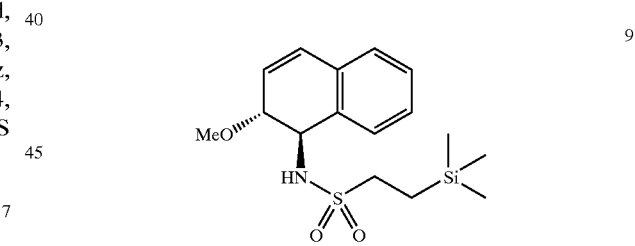
9

To a round bottomed flask was added 5 (61 mg, 0.2 mmol), [Rh(COD)Cl]$_2$ (2.5 mg, 0.005 mmol), and DPPF (5.5 mg, 0.01 mmol). THF (1 ml) and MeOH (1 ml) were then added and the solution heated to reflux for 6 hours. The reaction mixture was then concentrated and chromatographed to give 9 (53 mg, 78%) a colourless oil. $^1$H NMR (400 MHz, CDCl$_3$) δ 7.51–7.47 (1H, m), 7.30–7.24 (2H, m), 7.14–7.10 (1H, m), 6.59 (1H, d, J=9.9 Hz), 6.10 (1H, dd, J=3.7, 9.9 Hz), 5.41(1H, dd, J=8.8, 8.8 Hz), 4.55 (1H, d, J=8.8 Hz), 4.06 (1H, dd, J=3.6, 6.9 Hz), 3.45 (3H, s), 3.04–2.95 (2H, m), 1.07–0.85 (2H, m), 0.03 (6H, s); $^{13}$C NMR (400 MHz, CDCl$_3$) δ 133.7, 131.9, 129.9, 128.7, 128.4, 127.7, 127.2, 125.5, 77.3, 56.5, 55.5, 50.2, 10.5, −2.0. HRMS calcd for C$_{16}$H$_{25}$NO$_3$SSi (M$^+$): 339.1324. Found: 339.1327.

Example 10

Compounds Formed in Reactions Involving Phenol Nucleophiles

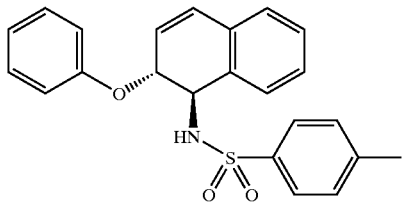

10

To a round bottomed flask was added 3 (60 mg, 0.2 mmol), [Rh(COD)Cl]$_2$ (2.5 mg, 0.005 mmol), and DPPF (5.5 mg, 0.01 mmol). THF (2 ml) and PhOH (94 mg, 1.0 mmol) were added and the solution heated to reflux for 12 hours. The reaction mixture was then concentrated and chromatographed to give 10 (63 mg, 81%) a crystalline solid. $^1$H NMR (400 MHz, CDCl$_3$) δ 7.72 (2H, d, J=8.2 Hz), 7.30–7.20 (5H, m), 7.14–7.09 (2H, m), 6.98–6.92 (1H, m), 6.87 (1H, d, J=7.4 Hz), 6.77 (2H, d, J=8.4 Hz), 6.64 (1H, d, J=10.2 Hz), 6.06 (1H, dd, J=4.6, 9.2 Hz), 5.00 (1H, dd, J=4.7, 4.7 Hz), 4.71–4.64 (2H, m), 2.44 (3H, s); $^{13}$C NMR (400 MHz, CDCl$_3$) δ 156.8, 143.6, 137.5, 132.5, 131.7, 130.9, 129.7, 129.5, 128.9, 128.6, 128.2, 127.4, 127.4, 124.2, 121.4, 115.9, 73.2, 54.4, 21.5. Anal. Calcd for C$_{23}$H$_{21}$NO$_3$S: C, 70.56; H, 5.41; N, 3.58. Found: C, 70.58; H, 5.43; N, 4.18.

Example 11

Compounds Formed in Reactions Involving Nitrogen or Carbon Nucleophiles

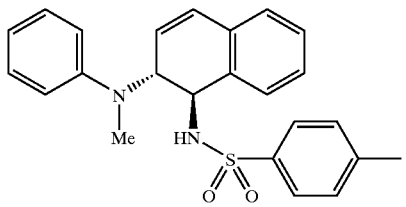

11

To a round bottomed flask was added 3 (60 mg, 0.2 mmol), [Rh(COD)Cl]$_2$ (2.5 mg, 0.005 mmol), and DPPF (5.5 mg, 0.01 mmol). THF (2 ml) and N-methylaniline (107 mg, 1.0 mmol) were added and the solution heated to reflux for 8 hours. The reaction mixture was then concentrated and chromatographed to give 11 (72 mg, 89%) a crystalline solid. mp 136–142° C.; $^1$H NMR (400 MHz, CDCl$_3$) δ 7.62 (2H, d, J=8.1 Hz), 7.26–7.18 (4H, m), 7.14–7.08 (2H, m), 6.90 (1H, d, J=7.3 Hz), 6.80–6.68 (4H, m), 5.86 (1H, dd, J=4.6, 9.9 Hz), 4.73–4.53 (2H, m), 2.42 (3H, s), 2.34 (3H, s); $^{13}$C NMR (400 MHz, CDCl$_3$) δ 148.9, 143.4, 137.5, 133.7, 132.2, 130.4, 129.6, 129.2, 128.7, 128.4, 127.7, 127.3, 127.0, 126.0, 117.6, 113.8, 58.9, 54.6, 32.3, 21.5. Anal. Calcd for C$_{24}$H$_{24}$N$_2$O$_2$S: C, 71.26; H, 5.98; N, 6.93. Found: C, 71.32; H, 6.01; N, 4.16.

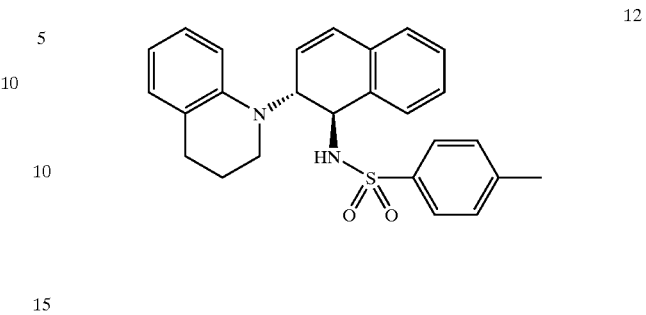

12

To a round bottomed flask was added 3 (60 mg, 0.2 mmol), [Rh(COD)Cl]$_2$ (2.5 mg, 0.005 mmol), and DPPF (5.5 mg, 0.01 mmol). THF (2 ml) and tetrahydroquinoline (133 mg, 1.0 mmol) were added and the solution heated to reflux for 9 hours. The reaction mixture was then concentrated and chromatographed to give 12 (63 mg, 73%) a crystalline solid. mp 135–137° C.; $^1$H NMR (400 MHz, CDCl$_3$) δ 7.63 (2H, d, J=8.2 Hz), 7.25–7.20 (1H, m), 7.18 (2H, d, J=8.2 Hz), 7.11–7.00 (3H, m), 6.90 (1H, d, J=6.4 Hz), 6.83 (2H, d, J=7.9 Hz), 6.71 (1H, d, J=9.7 Hz), 6.64–6.58 (1H, m), 5.84 (1H, dd, J=5.0, 9.7 Hz), 4.83 (1H, d, J=8.1 Hz), 4.66 (1H, dd, J=4.6, 4.6 Hz), 4.58 (1H, dd, J=4.7, 7.8 Hz), 3.00–2.94 (1H, m), 2.62–2.40 (3H, m), 2.41 (3H, s), 1.60–1.52 (2H, m); $^{13}$C NMR (400 MHz, CDCl$_3$) δ 144.3, 143.2, 137.7, 133.8, 132.2, 130.7, 129.5, 129.5, 128.6, 128.2, 127.8, 127.1, 127.1, 127.0, 125.8, 123.3, 116.4, 111.7, 57.1, 53.9, 43.0, 25.0, 22.2, 21.5. Anal. Calcd for C$_{26}$H$_{26}$N$_2$O$_2$S: C, 72.53; H, 6.09; N, 6.51. Found: C, 72.55; H, 6.11; N, 6.50.

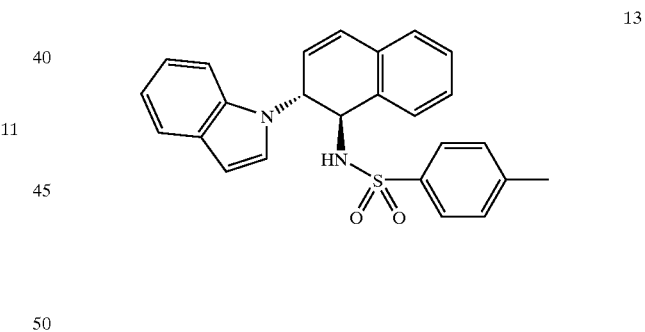

13

To a round bottomed flask was added 3 (60 mg, 0.2 mmol), [Rh(COD)Cl]$_2$ (2.5 mg, 0.005 mmol), and DPPF (5.5 mg, 0.01 mmol). THF (2 ml) and indole (117 mg, 1.0 mmol) were added and the solution heated to reflux for 11 hours. The reaction mixture was then concentrated and chromatographed to give 13 (75 mg, 91%) a white-solid. mp 132–135° C.; $^1$H NMR (400 MHz, CDCl$_3$) δ 7.84 (1H, s), 7.70–7.64 (3H, m), 7.24–7.07 (7H, m), 6.95–6.89 (1H, m), 6.65 (1H, d, J=9.7 Hz), 6.57 (1H, d, J=2.4 Hz), 6.50 (1H, d, J=7.5 Hz), 6.09 (1H, dd, J=5.1, 9.5 Hz), 4.99 (1H, d, J=7.7 Hz), 4.54 (1H, dd, J=2.9, 7.7 Hz), 4.26–4.22 (1H, m), 2.38 (3H, s); $^{13}$C NMR (4001 MHz, CDCl$_3$) δ 143.2, 136.5, 132.4, 132.2, 132.2, 129.5, 128.9, 128.7, 128.6, 127.7, 127.1, 127.0, 126.4, 126.3, 122.5, 122.0, 119.5, 119.0, 112.2, 111.2, 56.0, 38.8, 21.5. HRMS calcd for C$_{25}$H$_{22}$N$_2$O$_2$S (M$^+$): 414.1402. Found: 414.1407.

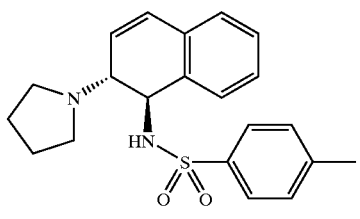

14

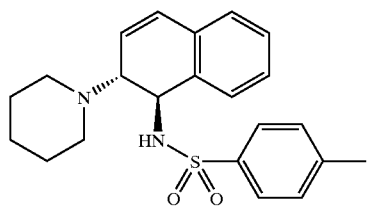

16

To a round bottomed flask was added 3 (60 mg, 0.2 mmol), [Rh(COD)Cl]₂ (2.5 mg, 0.005 mmol), and DPPF (5.5 mg, 0.01 mmol). THF (2 ml) was then added followed by triethylamine hydrochloride (138 mg, 1.0 mmol) and pyrrolidine (83 μl, 1.0 mmol). The resulting heterogeneous mixture was heated to reflux for 14 hours. Upon completion, the reaction mixture was concentrated and chromatographed to give 14 (70 mg, 96%) a white solid. The regiochemistry and relative stereochemistry was proven by X-ray diffraction. $^1$H NMR (400 MHz, CDCl₃) δ 7.74 (2H, d, J=8.3 Hz), 7.30 (2H, d, J=8.2 Hz), 7.22–7.17 (1H, m), 7.08–7.02 (2H, m), 6.84 (1H, d, J=7.5 Hz), 6.61 (1H, d, J=9.7 Hz), 5.93 (1H, dd, J=4.9, 9.7 Hz), 4.70 (1H, br s), 4.45 (1H, d, J=3.7 Hz), 3.89 (1H, dd, J=4.2, 4.2 Hz), 2.58–2.49 (2H, m), 2.45 (3H, s), 2.36–2.29 (2H, m), 1.63–1.58 (4H, m); Anal. Calcd for $C_{21}H_{24}N_2O_2S$: C, 68.45; H, 6.56; N, 7.60. Found: C, 68.51; H, 6.62; N, 7.55.

To a round bottomed flask was added 3 (60 mg, 0.2 mmol), [Rh(COD)Cl]₂ (2.5 mg, 0.005 mmol), and DPPF (5.5 mg, 0.01 mmol). THF (2 ml) was then added followed by triethylamine (140 μl, 1.0 mmol) and piperidine hydrochloride (121 mg, 1.0 mmol). The resulting heterogeneous mixture was heated to reflux for 14 hours. Upon completion, the reaction mixture was concentrated and chromatographed to give 16 (72 mg, 94%) a white solid. mp 116–117° C.; $^1$H NMR (400 MHz, CDCl₃) δ 7.75 (2H, d, J=8.2 Hz), 7.30 (2H, d, J=7.8 Hz), 7.21–7.18 (1H, m), 7.10–7.05 (1H, m), 7.04 (1H, d, J=7.5 Hz), 6.94 (1H, d, J=7.5 Hz), 6.61 (1H, dd, J=1.0, 9.7 Hz), 5.91 (1H, dd, J=4.8, 9.7 Hz), 4.82 (1H, s (br)), 4.53 (1H, d, J=4.4 Hz), 3.38–3.35 (1H, m), 2.44 (3H, s), 2.41–2.34 (2H, m), 2.16–2.09 (2H, m), 1.40–1.26 (6H, m); $^{13}$C NMR (400 MHz, CDCl₃) δ 143.3, 137.7, 134.2, 132.2, 129.6, 129.4, 128.2, 128.0, 127.7, 127.2, 126.6, 125.0, 64.2, 50.9, 49.6, 26.2, 24.3, 21.5. HRMS calcd for $C_{22}H_{26}N_2O_2S$ (M⁺): 382.1715. Found: 382.1713.

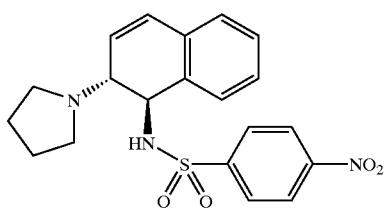

15

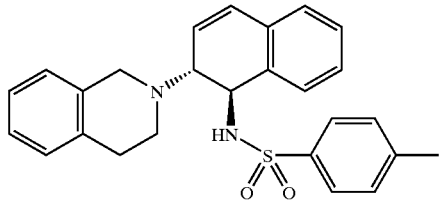

17

To a round bottomed flask was added 4 (66 mg, 0.2 mmol), [Rh(COD)Cl]₂ (2.5 mg, 0.005 mmol), and DPPF (5.5 mg, 0.01 mmol). THF (2 ml) was then added followed by triethylamine hydrochloride (138 mg, 1.0 mmol) and pyrrolidine (83 μl, 1.0 mmol). The resulting heterogeneous mixture was heated to reflux for 16 hours. Upon completion, the reaction mixture was concentrated and chromatographed to-give 15 (67 mg, 84%) a white solid. mp 142–145° C.; $^1$H NMR (400 MHz, CDCl₃) δ 8.30 (2H, d, J=8.8 Hz), 7.99 (2H, d, J=8.8 Hz), 7.24–7.18 (1H, m), 7.10–7.04 (2H, m), 6.95–6.90 (1H, m), 6.63 (1H, d, J=9.9 Hz), 5.93 (1H, dd, J=4.7, 9.7 Hz), 5.20–4.80 (1H, br s), 4.60 (1H, d, J=3.8 Hz), 3.40–3.35 (1H, m), 2.58–2.50 (2H, m), 2.43–2.34 (2H, m), 1.64–1.57 (4H, m); $^{13}$C NMR (400 MHz, CDCl₃) δ 149.8, 147.1, 132.8, 131.9, 129.7, 128.8, 128.2, 128.1, 128.0, 127.1, 125.0, 124.1, 61.4, 54.4, 50.0, 23.4. Anal. Calcd for $C_{20}H_{21}N_3O_4S$: C, 60.13; H, 5.30; N, 10.52. Found: C, 60.16; H, 5.33; N, 10.50.

To a round bottomed flask was added 3 (60 mg, 0.2 mmol), [Rh(COD)Cl]₂ (2.5 mg, 0.005 mmol), and DPPF (5.5 mg, 0.01 mmol). THF (2 ml) was then added followed by triethylamine hydrochloride (138 mg., 1.0 mmol) and tetrahydroisoquinoline (125 μl, 1.0 mmol). The resulting heterogeneous mixture was heated to reflux for 15 hours. Upon completion, the reaction mixture was concentrated and chromatographed to give 17 (70 mg, 81%) a white solid. mp 142–146° C.; $^1$H NMR (400 MHz, CDCl₃) δ 7.73 (2H, d, J=8.2 Hz), 7.26–7.18 (3H, m), 7.12–6.98 (5H, m), 6.90 (1H, d, J=8.1 Hz), 6.80 (1H, d, J=6.8 Hz), 6.67 (1H, d, J=9.7 Hz), 5.95 (1H, dd, J=4.7, 9.7 Hz), 4.80 (1H, s), 4.62 (1H, s), 3.68 (1H, AB, d, J=15.0 Hz), 3.63 (1H, dd, J=4.5, 4.5 Hz), 3.40 (1H, AB, d, J=15.0 Hz), 2.68–2.56 (4H, m), 2.40 (3H, s); $^{13}$C NMR (400 MHz, CDCl₃) δ 143.4, 137.7, 137.7, 134.1, 133.8, 132.2, 129.9, 129.6, 128.6, 128.5, 128.3, 127.9, 127.2, 126.8, 126.5, 125.9, 125.4, 124.6. Anal. Calcd for $C_{26}H_{26}N_2O_2S$: C, 72.53; H, 6.09; N, 6.51. Found: C, 72.56; H, 6.12; N, 6.50.

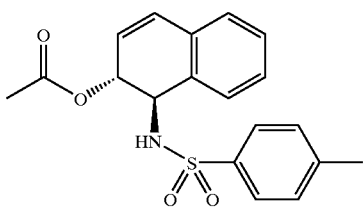

18

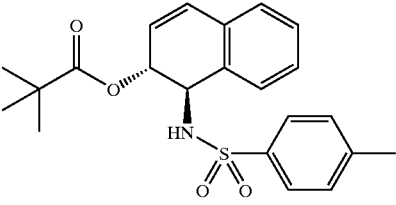

20

To a round bottomed flask was added 3 (60 mg, 0.2 mmol), [Rh(COD)Cl]$_2$ (2.5 mg, 0.005 mmol), and DPPF (5.5 mg, 0.01 mmol). THF (1 ml) was then added followed by triethylamine hydrochloride (138 mg, 1.0 mmol) and potassium acetate (98 mg, 1.0 mmol). The resulting heterogeneous mixture was heated to reflux for 15 hours. Upon completion, the reaction mixture was concentrated and chromatographed to give 18 (63 mg, 88%) a white solid. $^1$H NMR (400 MHz, CDCl$_3$) δ 7.77 (2H, d, J=8.3 Hz), 7.31(2H, d, J=8.2 Hz), 7.27–7.22 (1H, m), 7.19–7.07 (3H, m), 6.54 (1H, d, J=10.2 Hz), 5.88 (1H, dd, J=3.7, 10.2 Hz), 5.48–5.44 (1H, m), 4.90 (1H, d, J=8.4 Hz), 4.74–4.69 (1H, m), 2.44 (3H, s), 1.78 (3H, s); $^{13}$C NMR (400 MHz, CDCl$_3$) δ 170.6, 143.4, 138.2, 132.8, 131.9, 130.3, 129.7, 128.7, 128.5, 127.4, 127.1, 127.1, 125.0, 71.0, 55.7, 21.5, 20.7. Anal. Calcd for C$_{19}$H$_{19}$NO$_4$S: C, 63.85; H, 5.36; N, 3.92. Found: C, 63.88; H, 5.40; N, 3.81.

To a round bottomed flask was added 3 (60 mg, 0.2 mmol), [Rh(COD)Cl]$_2$ (2.5 mg, 0.005 mmol), and DPPF (5.5 mg, 0.01 mmol). THF (1 ml) was then added followed by triethylamine (140 μl, 1.0 mmol) and pivalic acid (102 mg, 1.0 mmol). The resulting homogeneous solution was heated to reflux for 15 hours. Upon completion, the reaction mixture was concentrated and chromatographed to give 20 (61 mg, 77%) a white solid. $^1$H NMR (400 MHz, CDCl$_3$) δ 7.75 (2H, d, J=8.0 Hz), 7.28 (2H, d, J=8.0 Hz), 7.16–7.00 (3H, m), 6.85 (1H, d, J=7.6 Hz), 6.55 (1H, d, J=9.7 Hz), 5.91 (1H, dd, J=4.1, 9.7 Hz), 5.34 (1H, dd, J=5.9, 5.9 Hz), 4.98 (1H, d, J=8.4 Hz), 4.70 (1H, dd, J=7.3, 7.3 Hz), 2.42 (3H, s), 1.07 (9H, s). HRMS calcd for C$_{22}$H$_{25}$NO$_4$S (M$^+$): 399.1504. Found: 399.1507.

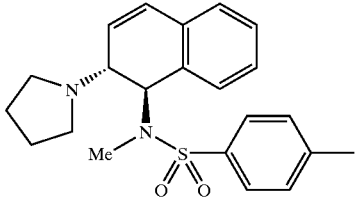

21

To a round bottomed flask was added 21 (100 mg, 0.27 mmol) and potassium carbonate (112 mg. 0.81 mmol). Acetone (3 ml) was then added followed by iodomethane (18 μl, 0.28 mmol). The mixture was stirred at room temperature for 4 hours then quenched with water. Extraction with ethylacetate, combining of the organic fractions and concentration gave a light yellow solid. Chromatography gave pure 21 (101 mg, 98%) a white crystalline solid. mp 109–111° C.; $^1$H NMR (400 MHz, CDCl$_3$) δ 7.86 (2H, d, J=8.0 Hz), 7.31 (2H, d, J=8.0 Hz), 7.26–7.12 (3H, m), 7.06 (1H, d, J=6.9 Hz), 6:58 (1H, d; J=9.7 Hz), 5.95 (1H, dd, J=4.6, 9.9 Hz), 5.35 (1H, d, J=4.5 Hz), 3.42 (1H, dd, J=4.5, 4.5 Hz), 2.62–2.48 (4H, m), 2.50 (3H, s), 2.45 (3H, s), 1.70–1.63 (4H, m); $^{13}$C NMR (400 MHz, CDCl$_3$) δ 143.0, 137.7, 133.6, 132.1, 129.5, 129.1, 128.9, 128.2, 128.1, 127.4, 126.5, 125.9, 58.2, 56.5, 48.6, 29.6, 23.5, 21.5. Anal. Calcd for C$_{22}$H$_{26}$N$_2$O$_2$S: C, 69.08; H, 6.85; N, 7.32. Found: C, 69.14; H, 6.91; N, 7.30.

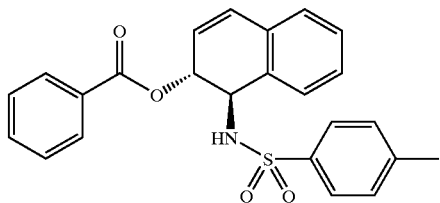

19

To a round bottomed flask was added 3 (60 mg, 0.2 mmol), [Rh(COD)Cl]$_2$ (2.5 mg, 0.005 mmol), and DPPF (5.5 mg, 0.01 mmol). THF (1 ml) was then added followed by triethylamine (140 μl, 1.0 mmol) and benzoic acid (122 mg, 1.0 mmol). The resulting homogeneous solution was heated to reflux for 15 hours. Upon completion, the reaction mixture was concentrated and chromatographed to give 19 (73 mg, 87%) a white solid. mp 158–162° C.; $^1$H NMR (400 MHz, CDCl$_3$) δ 7.77 (2H, d, J=7.1 Hz), 7.65 (2H, d, J=8.3 Hz), 7.56–7.50 (1H, m), 7.40–7.32 (3H, m), 7.30–7.22 (2H, m), 7.11 (1H, dd, J=1.3, 7.2 Hz), 6.98 (2H, d, J=8.1 Hz), 6.56 (1H, dd, J=1.3, 9.9 Hz), 5.93 (1H, dd, J=3.3, 9.7 Hz), 5.79 (1H, ddd, J=1.7, 3.3, 9.2 Hz), 5.12 (1H, d, J=8.4 Hz), 4.90 (1H, dd, J=8.8, 8.8 Hz), 2.19 (3H, s); $^{13}$C NMR (400 MHz, CDCl$_3$) δ 166.4, 143.3, 138.0, 133.4, 133.3, 132.3, 130.4, 130.0, 129.7, 128.8, 128.8, 128.3, 127.5, 127.2, 126.9, 125.7, 72.3, 56.8, 21.6. HRMS calcd for C$_{24}$H$_{21}$NO$_4$S (M$^+$): 419.1191. Found: 419.1997.

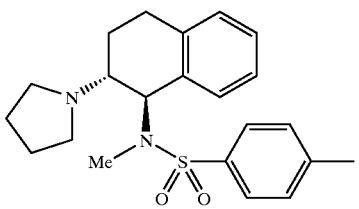

22

To a round bottomed flask was added 21 (100 mg, 0.26 mmol), ethylacetate (2 ml) and palladium on carbon (5 mg).

Hydrogen was added over this heterogeneous mixture via balloon for 15 hours. Upon completion, the mixture was filtred through celite and concentrated to give 22 a white solid. Crude $^1$H NMR showed that this crude product was >95% pure. Further purification could be obtained by chromatography giving pure 22 (98 mg, 98%). mp 109–110° C.; $^1$H NMR (400 MHz, CDCl$_3$) δ 7.99 (2H, d, J=S 8.1 Hz), 7.30 (2H, d, J=8.3 Hz), 7.15–7.02 (4H, m), 5.29 (1H, d, J=8.1 Hz), 3.03–2.67 (5H, m), 2.65–2.52 (2H, m), 2.44 (3H, s), 2.43 (3H, s), 2.05–1.96 (1H, m), 1.90–1.80 (1H, m), 1.72–1.64 (4H, m); $^{13}$C NMR (400 MHz, CDCl$_3$) δ 142.8, 138.5, 137.5, 133.9, 129.2, 128.5, 127.7, 127.1, 126.4, 60.0, 59.3, 48.7, 30.3, 27.9, 23.6, 21.5, 21.41 . Anal. Calcd for C$_{22}$H$_{28}$N$_2$O$_2$S: C, 68.72; H, 7.34; N, 7.29. Found: C, 68.79; H, 7.37; N, 7.22.

23

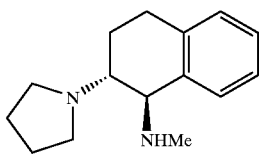

To a quartz tube was added 22 (80 mg, 0.2 mmol), 1,4-dimethoxybenzene (110 mg, 0.8 mmol) and sodium borohydride (76 mg, 2.0 mmol) followed by 90% aqueous ethanol solution (3 ml). The mixture was irradiated at 254 nm in a rayonet reactor for 2.5 hours. The crude mixture was concentrated azeotropically with ethanol and then chromatographed (90% acetone, 9% MeOH, 1% triethylamine) to give 23 (42 mg, 91%). Spectral data was identical to the literature data.

24

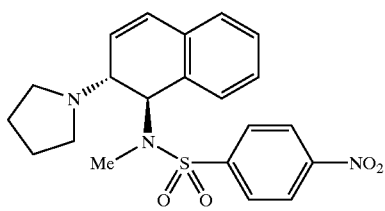

To a round bottomed flask was added 16 (100 mg, 0.25 mmol) and potassium carbonate (112 mg, 0.81 mmol). Acetone (3 ml) was then added followed by iodomethane (18 μl, 0.28 mmol). The mixture was stirred at room temperature for 4 hours then quenched with water. Extraction with ethylacetate, combining of the organic fractions and concentration gave a light yellow solid. Chromatography gave pure 24 (101 mg, 98%) a white crystalline solid. mp 139–141° C.; $^1$H NMR (400 MHz, CDCl$_3$) δ 8.35 (2H, d, J=8.8 Hz), 8.22 (2H, d, J=8.8 Hz), 7.28–7.22 (3H, m), 7.09 (1H, d, J=6.2 Hz), 6.60 (1H, d, J=9.9 Hz), 5.95 (1H, dd, J=4.0, 9.9 Hz), 5.43 (1H, d, J=6.6 Hz), 3.54–3.49 (1H, m), 2.62 (3H, s), 2.60–2.54 (4H, m), 1.72–1.66 (4H, m); $^{13}$C NMR (400 MHz, CDCl$_3$) δ 149.8, 146.6, 133.6, 131.6, 129.5, 128.6, 128.3, 128.0, 126.8, 125.3, 124.0, 58.4, 58.0, 48.5, 29.8, 23.7. Anal. Calcd for C$_{21}$H$_{23}$N$_3$O$_4$S: C, 61.00; H, 5.61; N, 10.16. Found: C, 61.11; H, 5.65; N, 10.12.

25

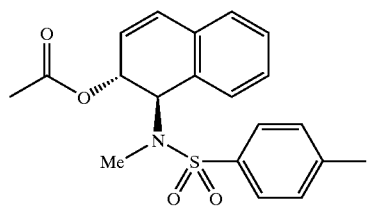

To a round bottomed flask was added 18 (70 mg, 0.20 mmol) and potassium carbonate (110 mg, 0.80 mmol). Acetone (2.5 ml) was then added followed by iodomethane (15 μl, 0.24 mmol). The mixture was stirred at room temperature for 4 hours then quenched with water. Extraction with ethylacetate, combining of the organic fractions and concentration gave a light yellow solid. Chromatography gave pure 25 (67 mg, 91%) a white crystalline solid. mp 113–116° C.; $^1$H NMR (400 MHz, CDCl$_3$) δ 7.78 (2H, d, J=8.2 Hz), 7.32 (2H, d, J=8.2 Hz), 7.25–7.17 (2H, m), 7.13–6.98 (2H, m),6.46 (1H, dd, J=1.8, 9.9 Hz), 5.85 (1H, dd, J=2.9, 9.9 Hz), 5.71 (1H, ddd, J=2.0, 2.6, 10.1 Hz), 5.60 (1H, d, J=10.1 Hz),2.69(3H, s),2.44(3H, s), 1.90(3H, s); $^{13}$C NMR (400 MHz, CDCl$_3$) δ 170.2, 143.4, 137.3, 133.2, 131.4, 129.6, 129.2, 128.4, 128.3, 127.1, 126.7, 126.4, 69.7, 60.0, 29.5, 21.4, 20.8. Anal. Calcd for C$_{20}$H$_{21}$NO$_4$S: C, 64.67; H, 5.70; N, 3.77. Found: C, 64.75; H, 5.77; N, 3.72.

Abbreviations

| | |
|---|---|
| ee | "enantiomerically enriched," or "enantiomeric enrichment" |
| THF | tetrahydrofuran |
| DPPE | 1,2-bis(diphenylphosphino)ethane |
| BINAP | 2,2'-bis(diphenylphosphino)-1,1'-binaphthyl |

What is claimed is:

1. A compound according to formula IV:

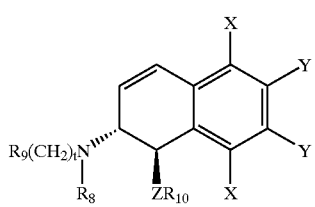

(IV)

wherein:

a) $R_8$ is H or $CH_3$;

b) t=0–3 c) $R_9$ is a $C_3$–$C_6$ aryl optionally substituted at one or more positions with a group selected from: a $C_1$–$C_3$ alkyl; a $C_1$–$C_3$ alkoxy; Cl; F; $NO_2$; and $CF_3$;

d) X and Y are independently selected from the group consisting of H; $NH_2$; F; Cl; Br; a $C_1$–$C_3$ alkyl; and a $C_1$–$C_3$ alkoxy; or wherein the combination XY or YY together form a $C_3$–$C_6$ carbocyclic ring or a $C_3$–$C_6$ heterocyclic ring containing one or more heteroatoms selected from the group consisting of O; N; and S;

e) Z is selected from O or $NR_a$, wherein $R_a$ is selected from:

(i) a straight or branched $C_1$–$C_6$ alkyl;
(ii) phenyl;
(iii) (O)C—O—$R_b$, wherein $R_b$ is a straight or branched $C_1$–$C_6$ alkyl;
(iv) —$SO_2$—$R_c$, wherein $R_c$ is an unsubstituted phenyl or a phenyl substituted with a $C_1$–$C_3$ alkyl or $NO_2$; and
(v) —$SO_2$—$(CH_2)_q$—$Si(CH_3)_3$ wherein q is 1–3;
and with the proviso that when Z is O, $R_{10}$ is H; when Z is $NR_a$, $R_{10}$ is either H or $CH_3$;
and with the further proviso that when Z is O and $R_{10}$ is H, t is 2 or 3 and either X or Y is not H.

2. The compound of claim 1, wherein $R_8$ is H.
3. The compound of claim 1, wherein X=H and Y=H.
4. A compound selected from the group consisting of:
(1S,2S)-N-(1-hydroxyl-1,2-dihydro-naphthalen-2-yl)-benzene sulfonamide;
(1R,2R)-2-(methyl-phenyl-amino)-1,2-dihydro-naphthalen-1-ol;
(1R*,2R*)-2-benzylamino-1,2-dihydro-naphthalen-1-ol;
(1R*,2R* )-2-(4-methoxy-benzylamino)-1,2-dihydro-naphthalen-1-ol;
(1R,2S)-2-methoxy-N-phenyl-1,2-dihydro-1-naphthalenamine;
tert-butyl(1R,2S)-2-methoxy-1,2-dihydro-1-naphthalenylcarbamate;
N-[(1R,2S)-2-methoxy-1,2-dihydro-1-naphthalenyl]-2-(trimethylsilyl) ethanesulfonamide;
N-[(1R,2S)-2-methoxy-1,2,3,4-tetrahydro-1-naphthalenyl]-4-methylbenzenesulfonamide;
N-[(1R,2S)-2-methoxy-1,2,3,4-tetrahydro-1-naphthalenyl]-4-methylbenzenesulfonamide;
4-methyl-N-[(1R,2S)-2-phenoxy-1,2,3,4-tetrahydro-1-naphthalenyl]benzenesulfonamide;
(1R,2S)-1-{[(4-methylphenyl)sulfonyl]amino}-1,2,3,4-tetrahydro-2-naphthalenyl acetate;
(1R,2S)-1-{[(4-methylphenyl)sulfonyl]amino}-1,2-dihydro-2-naphthalenyl benzoate;
(1R,2S)-1-{[(4-methylphenyl)sulfonyl]amino}-1,2-dihydro-2-naphthalenyl pivalate;
N-[(1R,2S)-2-methoxy-1,2-dihydro-1-naphthalenyl]-2-(trimethylsilyl) ethanesulfonamide, and
tert-butyl(1R,2S)-2-methoxy-1,2-dihydro-1-naphthalenylcarbamate.

5. A pharmaceutical composition comprising a compound according to formula IV:

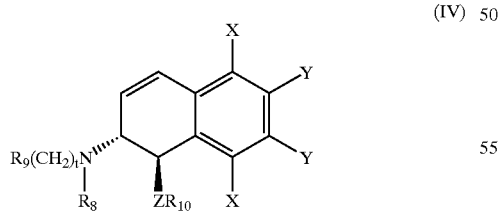

(IV)

wherein:
a) $R_8$ is H or $CH_3$;
b) t=0–3
c) $R_9$ is a $C_3$–$C_6$ aryl optionally substituted at one or more positions with a group selected from: a $C_1$—$C_3$ alkyl; a $C_1$–$C_3$ alkoxy; Cl; F; $NO_2$; and $CF_3$;
d) X and Y are independently selected from the group consisting of H; $NH_2$; F; Cl; Br; a $C_1$–$C_3$ alkyl; and a $C_1$–$C_3$ alkoxy; or wherein the combination XY or YY together form a $C_3$–$C_6$ carbocyclic ring or a $C_3$–$C_6$ heterocyclic ring containing one or more heteroatoms selected from the group consisting of O; N; and S;
e) Z is selected from O or $NR_a$, wherein $R_a$ is selected from:
(i) a straight or branched $C_1$–$C_6$ alkyl;
(ii) phenyl;
(iii) (O)C—O—$R_b$, wherein $R_b$ is a straight or branched $C_1$–$C_6$ alkyl;
(iv) —$SO_2$—$R_c$, wherein $R_c$ is an unsubstituted phenyl or a phenyl substituted with a $C_1$–$C_3$ alkyl or $NO_2$; and
(v) —SO—$(CH_2)_q$—$Si(CH_3)_3$ wherein q is 1–3; and
when Z is O, $R_{10}$ is H; when Z is $NR_a$; $R_{10}$ is either H or $CH_3$.

6. A pharmaceutical composition comprising a compound according to claim 4.
7. A method of treating a patient for pain, comprising administering to said patient an effective amount of the pharmaceutical compound of claim 5.
8. A method of treating a patient for Parkinson's disease, comprising administering an effective amount of the pharmaceutical composition of claim 5.
9. A method of treating a patient for cancer, comprising administering an effective amount of the pharmaceutical compound of claim 5.
10. A method of treating a patient for AIDS, comprising administering an effective amount of the pharmaceutical compound of claim 5.
11. A method of treating a patient for pain, comprising administering to said patient an effective amount of the pharmaceutical composition of claim 6.
12. A method of treating a patient for Parkinson's Disease, comprising administering to said patient an effective amount of the pharmaceutical composition of claim 6.
13. A method of treating a patient for cancer, comprising administering to said patient an effective amount of the pharmaceutical composition of claim 6.
14. A method of treating a patient for AIDS, comprising administering to said patient an effective amount of the pharmaceutical composition of claim 6.
15. A process for preparing a compound of formula IV:

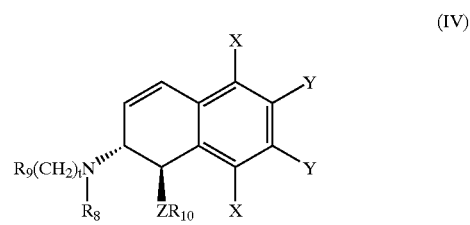

(IV)

wherein:
a) $R_8$ is H or $CH_3$;
b) t=0–3
c) $R_9$ is a $C_3$–$C_6$ aryl optionally substituted at one or more positions with a group selected from: a $C_1$–$C_3$ alkyl; a $C_1$–$C_3$ alkoxy; Cl; F; $NO_2$; and $CF_3$;

d) X and Y are independently selected from the group consisting of H; $NH_2$; F; Cl; Br; a $C_1$–$C_3$ alkyl; and a $C_1$–$C_3$ alkoxy; or wherein the combination XY or YY together form a $C_3$–$C_6$ carbocyclic ring or a $C_3$–$C_6$ heterocyclic ring containing one or more heteroatoms selected from the group consisting of O; N; and S;

e) Z is selected from O or $NR_a$ wherein $R_a$ is selected from:
  (i) a straight or branched $C_1$–$C_6$ alkyl;
  (ii) phenyl;
  (iii) (O)C—O—$R_b$ wherein $R_b$ is a straight or branched $C_1$–$C_6$ alkyl;
  (iv) —$SO_2$—$R_c$ wherein $R_c$ is an unsubstituted phenyl or a phenyl substituted with a $C_1$–$C_3$ alkyl or $NO_2$; and
  (v) —$SO_2$—$(CH_2)_q$—$Si(CH_3)_3$ wherein a is 1–3; and when Z is O, $R_{10}$ is H; when Z is $NR_a$, $R_{10}$ is either H or CH;

comprising reacting a compound of formula $R_9$—$(CH_2)_t$ $NHR_8$ with a compound of formula V

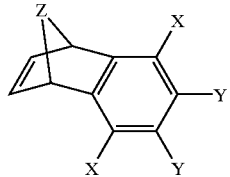

wherein $R_8$, $R_9$, t, X, Y, and Z are as defined above and wherein said reaction is catalyzed by $[Rh(COD)Cl]_2$ in the presence of a phosphine ligand.

16. The process of claim 15, wherein said phosphine ligand is selected from the group consisting of; DPPF; (R)-(S)-BPPFA; and (R)-(S)-PPF-P'$Bu_2$.

* * * * *